United States Patent [19]

De Vos et al.

[11] Patent Number: 5,969,128
[45] Date of Patent: Oct. 19, 1999

[54] NUCLEIC ACID PROBES CHEMICALLY MODIFIED AT 5'(OH) AND/OR AT 3'(OH) FOR THE PURPOSE OF INTRODUCING ONE OR MORE NON-RADIOACTIVE MARKING ELEMENTS AT THESE SITES, AND METHOD FOR PREPARING THE SAME

[75] Inventors: Marie-Joëlle De Vos, Feluy; Alex Bollen, Itterbeek, both of Belgium

[73] Assignee: La Region Wallone, Brussels, Belgium

[21] Appl. No.: 08/507,283

[22] PCT Filed: Feb. 18, 1994

[86] PCT No.: PCT/BE94/00013

§ 371 Date: Aug. 21, 1995

§ 102(e) Date: Aug. 21, 1995

[87] PCT Pub. No.: WO94/19364

PCT Pub. Date: Sep. 1, 1994

[30] Foreign Application Priority Data

Feb. 19, 1993 [BE] Belgium ............................... 09300160

[51] Int. Cl.$^6$ ..................................................... C07H 21/04
[52] U.S. Cl. ............................................................. 536/25.3
[58] Field of Search .................................... 536/25.3, 26.6

[56] References Cited

U.S. PATENT DOCUMENTS

| | | | |
|---|---|---|---|
| 4,743,535 | 5/1988 | Carico | 435/6 |
| 4,910,300 | 3/1990 | Urdea | 536/287 |
| 5,124,246 | 6/1992 | Urdea et al. | 435/6 |

FOREIGN PATENT DOCUMENTS

WO 92/05186  4/1992  WIPO .

OTHER PUBLICATIONS

N.D. Sinha et al., "Polymer support olgionucleotide systhesis XVIII$^{121}$", *Nucleic Acids Research*, vol. 12, No. 11, 1984.

*Primary Examiner*—Scott W. Houtteman
*Attorney, Agent, or Firm*—Sughrue, Mion, Zinn, Macpeak & Seas, PLLC

[57] ABSTRACT

The probe comprises: a) an oligonucleotide or oligodeoxyribonucleotide part constituted by a DNA or RNA nucleic acid sequence S, depending on the type of molecule to be detected, and b) a non-nucleotide part possessing chemical properties enabling direct or indirect atttachment of one or more detection units or marking elements M detectable non-isotopically by production of colour or light. The probe is characterized by the fact that part b) is constituted by a chain of phosphate units interspersed with alkyl groups, viz.: b1) certain alkyl groups uniting the different phosphate groups and presenting no special functionality b2) alkyl groups presenting primary amine groups which allow splicing with varied reagents to carry out direct or indirect detection, the b2) groups being bonded to part a) or sequence S by way of groups b1). Sequence S is bonded at its 5' and/or 3' extremity to one or more marking elements M. The probes of this type are used to detect and diagnose hereditary genetic diseases, oncogenes, viral, bacterial or parasitic diseases.

6 Claims, 8 Drawing Sheets

NUCLEIC ACID PROBES CHEMICALLY MODIFIED AT 5'(OH) AND/OR AT 3'(OH) FOR THE PURPOSE OF INTRODUCING ONE OR MORE NON-RADIOACTIVE MARKING ELEMENTS AT THESE SITES, AND METHOD FOR PREPARING THE SAME

This invention relates to non-radioactive nucleic acid probes, and to chemical compounds useful in the synthesis of the said probes. It is becoming increasingly common to use nucleic acid probes for the detection and diagnosis of hereditary genetic diseases, oncogenes, and diseases caused by viruses, bacteria or parasites, and they are being employed in clinical and veterinary fields and in the food-growing industry. The probes concerned are generally single-stranded DNA or RNA sequences which are capable, under certain experimental conditions, of regaining their complementary sequences and of forming hybrids with them so as to produce stable duplexes.

Originally, the method employed to detect DNA-DNA or DNA-RNA hybrids called for the use of radioactive marking: the probe is marked with a radioisotope, usually a $^{32}P$ radioisotope, and detection following hybridization entails counting or autoradiography.

In view of the drawbacks associated with the use of radioisotopes (period of decay, cost and security), there is a growing trend towards the use of "cold" probes (which do not contain a radioactive element). Cold probes employ detection techniques principally utilizing enzymatic systems which give rise to the production of a colour in the presence of a substrate, and, in the most recent systems, to the production of a light (fluorescence, chemiluminescence or bioluminescence).

As far as the marking of such probes is concerned, the techniques published to date may be broken down into two major categories:

1. The first consists in splicing the probe to a directly detectable element, for example by covalent splicing of an enzyme to the probe (alkaline phosphatase or peroxydase).

2. The second category consists in the indirect detection of the hybrid. This involves the use of intermediate substances which recognize the units attaching to the probe. These are chiefly systems based on very vigorous interaction between biotin and avidin or streptavidin, where avidin or streptavidin are paired with an enzyme. This approach requires one or more biotins to be incorporated in the nucleic probe.

Techniques based on the use of cold probes, whether involving direct or indirect detection, therefore necessitate chemical modifications to the oligonucleotide chain, at the said probes, in order to enable it to be marked.

Oligodeoxyribonucleotides bearing chemical groups such as primary amines or thiols which enable splicing with varied reagents have been described in the literature. The introduction of these groups may take place either on one or more of the bases, or at one of the 5' or 3' ends of the oligodeoxyribonucleotide. Chemical modifications at the bases of the chain have the disadvantage of interfering with the pairings of the bases when the oligonucleotide is made to form a hybrid with homologous sequences. To this end it is more judicious to introduce functional groups at 5' or at 3', provided that the technique proposed allows the detectable portion to be sufficiently removed from the oligonucleotide portion of the probe thus prepared.

It is therefore an object of this invention to obtain nucleic acid probes that:

i) offer good hybridization with the complementary target sequences;
ii) permit direct or indirect detection by non-radioactive methods and with the lowest possible detection threshold; and
iii) are easy to synthesize, in other words are suited to automatic or manual synthesis of nucleic acids, notably on a solid support.

Accordingly, the present invention concerns nucleic acid probes for detecting a DNA or RNA molecule, comprising
a) an oligonucleotide or oligodeoxynucleotide portion constituted by S: a DNA or RNA nucleic acid sequence, according to the type of molecule to be detected; and
b) a non-nucleotide portion possessing chemical properties that enable the direct or indirect attachment of one or more detection units or marking elements M detectable in a non-isotopic manner by producing colour or light, characterized in that portion b) is constituted by a chain of phosphate units interspersed with alkyl units, viz:
b1) certain alkyl units uniting the various phosphate groups and exhibiting no particular functionality;
b2) alkyl units exhibiting primary amine groups which permit splicing with varied reagents in order to achieve direct or indirect detection; units b2) are linked to portion a) or sequence S via units b1).

In accordance with the invention, sequence S is linked at its 5' and/or 3' end to one or more marking elements M.

The molecular structure having the X chemical groups enabling direct or indirect attachment of one or more detection units, may inter alia present two types of structure:

i) a "COMB" structure in which the X chemical groups are arranged in a linear chain.

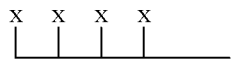

ii) a "CANDELABRA" structure in which the X chemical groups are arranged in a branching chain.

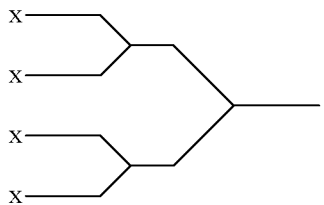

The present invention is concerned with both types of structure.

BRIEF DESCRIPTION OF THE DRAWINGS

FIGS. 1a–g, 2a–i, 3a–d, 4a–h, 5a–h, 6a–c, 7a–c and 8a–f display results of capillary electrophoresis analysis of products described in the specification.

Figure 1A:
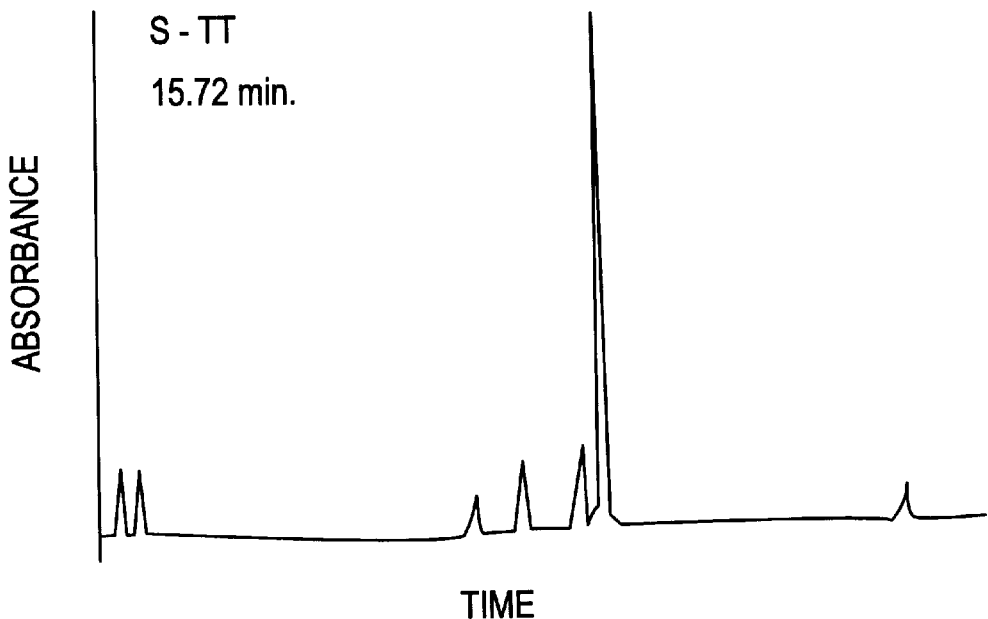
Figure 1B:
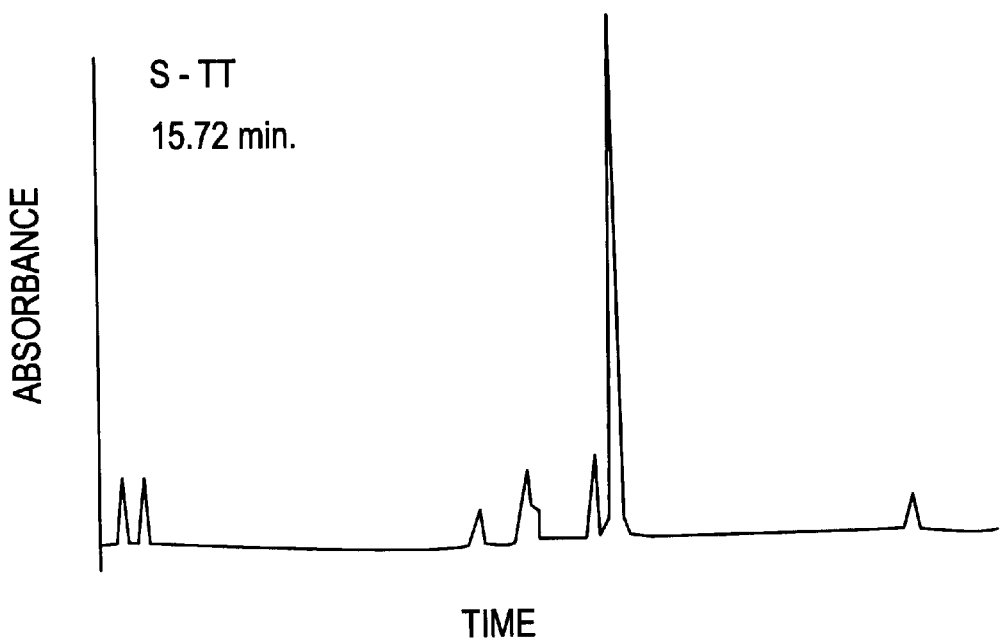
Figure 1C:
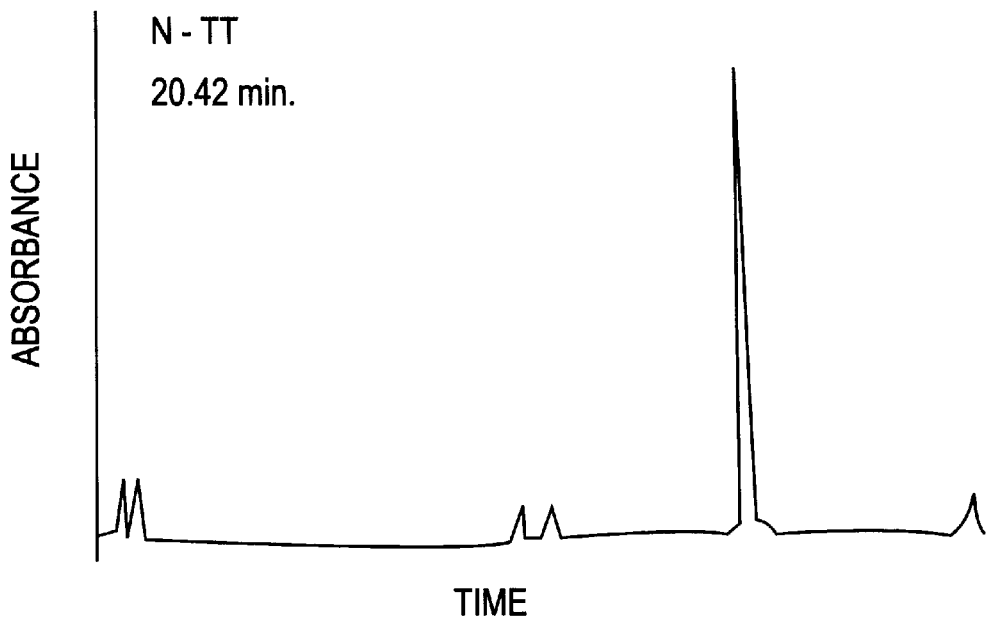
Figure 1D:
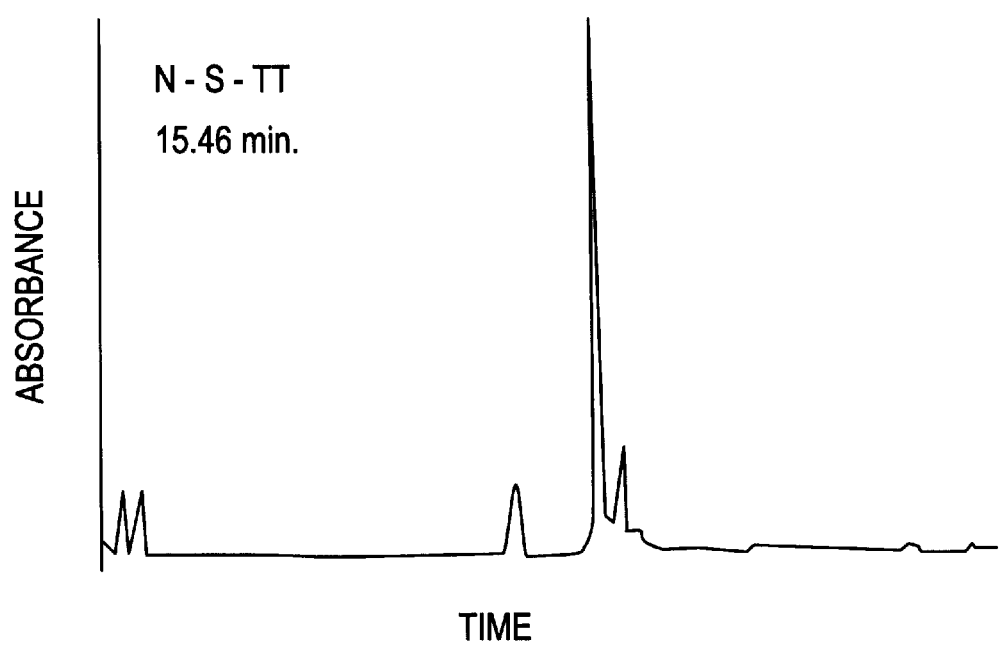
Figure 1E:
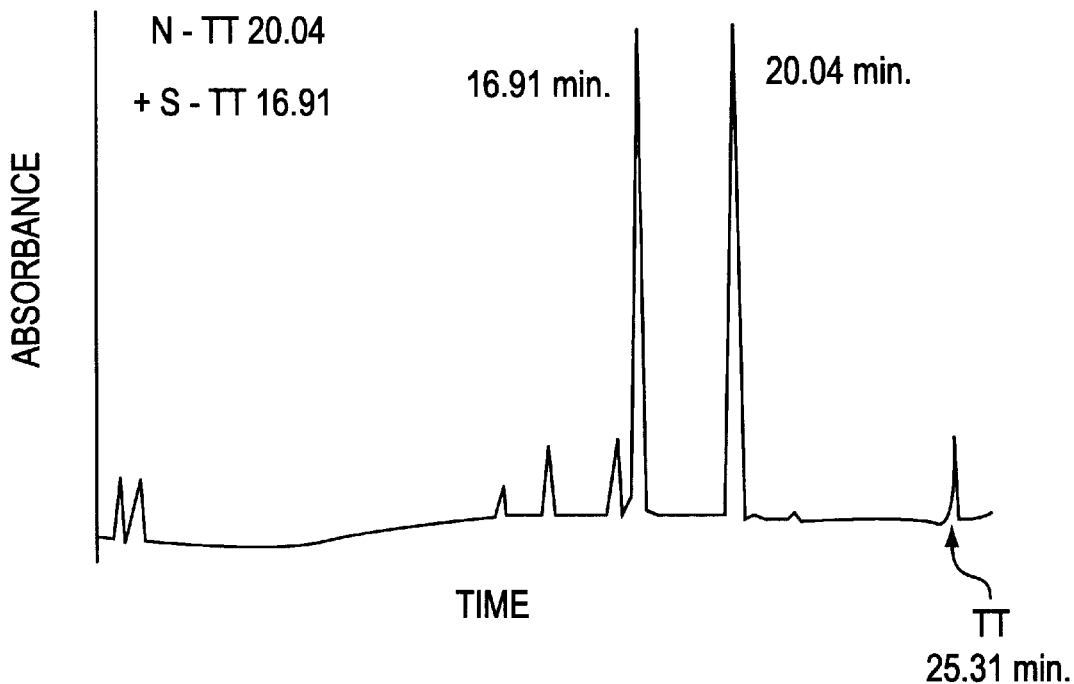
Figure 1F:
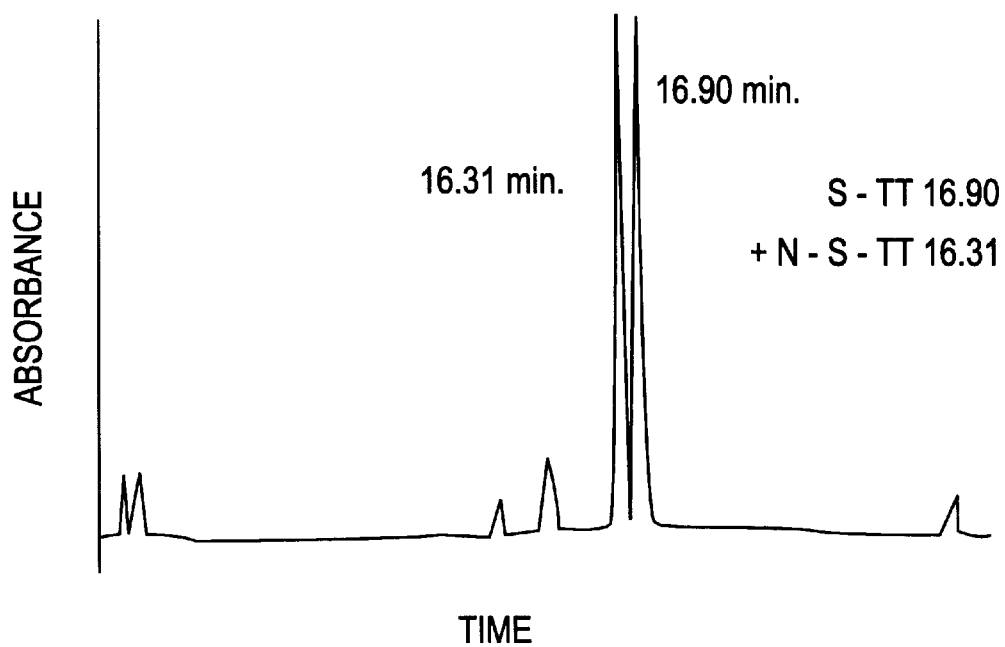
Figure 1G:
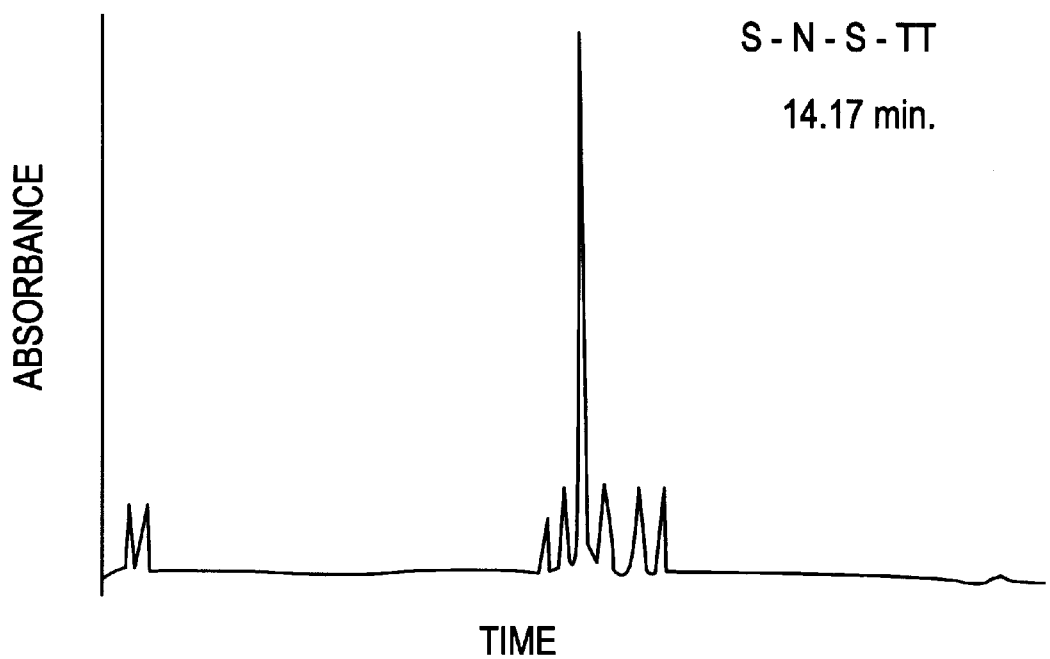

I. Nucleic Acid Probes Chemically Modified at 5'(OH) and (or) at 3'(OH) by a "COMB"-Type Molecular Structure In probes of this type, the nucleotide portion consists of a defined sequence of nucleic acids which is homologous with a target complementary fragment, it provides the stabilization energy and ensures hybridization with the DNA or RNA molecule that is to be detected. It is constituted by a chain of phosphate units interspersed with ribose units.

The non-nucleotide portion which provides the reactivity allowing either direct or indirect detection of the hybrid that is capable of being introduced into the 5'(OH) and/or 3'(OH) end of the nucleic acid sequence described above, is constituted by a linear chain of phosphate units interspersed with alkyl units, viz.:

L: certain alkyl units exhibit no particular chemical functionality; the order of appearance of such units, which are also known as a "chemical arm", consists in introducing spacings between the detection units;

M: certain alkyl units present primary amine groups which enable splicing with varied reagents leading to the formation of direct or indirect detection units.

The M units are separated from each other by a variable number of chemical arms L, and M includes a molecule, either synthetic or natural, that is detectable directly or indirectly in a non-isotopic manner. A probe thus constituted satisfies the general formula

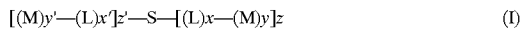
$$[(M)y'—(L)x']z'—S—[(L)x—(M)y]z \qquad (I)$$

wherein S, L and M have the meanings given above, x, x', z, z' are numbers equal to or higher than 0, with the restriction that z and z' are never simultaneously equal to 0, and y and y' are numbers higher than 0.

The chemical modification is therefore made at the 5' and/or 3' end of the sequence of nucleic acids, such that formula I may be specified as follows:

deoxyribonucleotides in the case of DNA. In the case of RNA the monomers, i.e. the nucleotides, are constituted by phosphoric acid, an ose of five carbon atoms, ribose (J=OH) and one of the four fundamental bases: adenine, guanine, cytosine and uridine. More seldom the so-called minor bases or nucleosides are encountered, such as methylated or hydroxylated bases, dihydrouracil and pseudo-uridine. In the case of DNA, the ose of the deoxyribonucleotides is D-2-deoxyribose (J=H) and the four principal bases are adenine, guanine, cytosine and thymine; in rare instances the cytosine is replaced by methylcytosine or hydroxymethylcytosine. One of the essential characteristics of the polynucleotides is the 3'–5' phosphodiester internucleotide bond.

L: the chemical arm
  x, x'=0 to 100
  n'=0 to 20

The chemical arm is a non-nucleotide polymer. One of the essential characteristics of this polymer, both in the case of DNA and RNA, is the phosphodiester bond which unites the monomers.

The monomer is constituted by phosphoric acid, one diol: propane 1–3 diol, substituted on carbon 1 by a lateral alkyl chain.

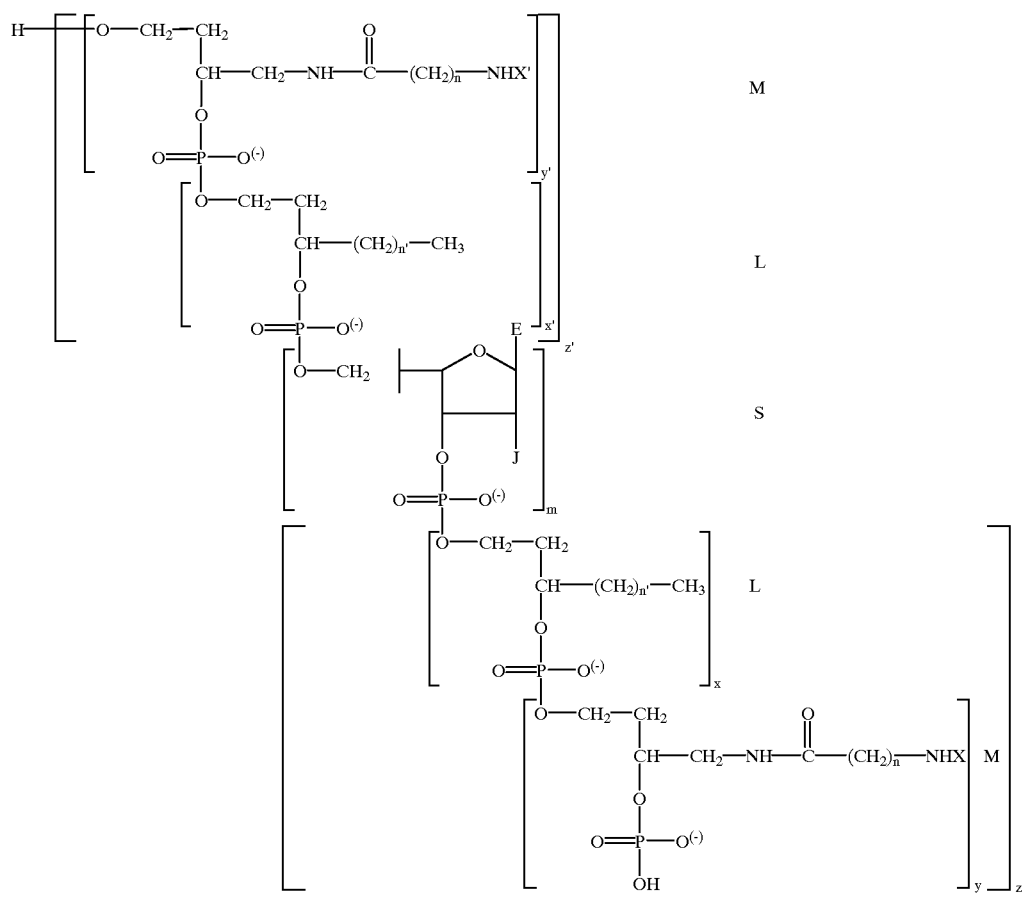

Units S, L and M may be described as follows:
S: the sequence of nucleic acids
  J=H or OH
  m represents the number of nucleotides from 1 to 1000
  B is the nucleic acid, purine or pyrimidine base, varying according to the nucleotides.

It will be recalled that nucleic acids are polymers of nucleotides, either ribonucleotides in the case of RNA, or M: marking element
  y, y'=1 to 100
  n=0 to 20
X: marker, either direct: alkaline phosphatase, peroxydase, fluorescein, any enzyme capable, in the presence of a substrate, of producing a colour or a light; or indirect: biotin, digoxigenin, any hapten capable of being recognized by antibodies marked in a non-isotopic manner.

The marking element is a non-nucleotide polymer. One of the essential characteristics of this polymer, both in the case of DNA and RNA, is the phosphodiester bond between the monomers.

The monomer is constituted by phosphoric acid, one diol: propane 1.3-diol substituted on carbon 1 by a methylene acetamido-alkane, the alkyl chain is functionalized at the terminal position by an amine bearing the marker.

Finally, the element LM responsible for detecting the probe may be introduced at 5'(OH) for $z' \neq 0$; $z=0$ or at 3'(OH) for $z'=0$; $z \neq 0$ or indeed simultaneously at 5'(OH) and at 3'(OH) for $z' \neq 0$; $z \neq 0$ with, generally speaking, z and $z'=0$ to 100.

The synthesis of compound Ia may thus be realised by classic internucleotide synthesis since the various elements of I, namely S, L and M, are polymers of which the monomers are interconnected to one another by phosphodiester bonds.

It is therefore the object of the present invention to provide a method for preparing probes of formula Ia comprising:

A1) the synthesis of a nucleic acid sequence S

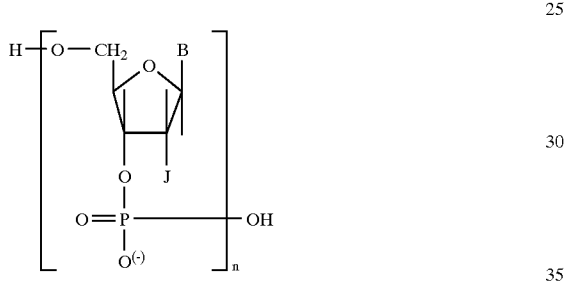

by any method of synthesis involving conventional manual or automatic internucleotide linkage, preferably on a solid support, and A2) the attachment of a marker, characterized in that said sequence is subjected, preferably using the same method of synthesis, viz. on a solid support, either to an extension at its 5'(OH) end by a series of M and L units or to an extension at its 3'(OH) end by a series of M and L units or to an extension at its 5'(OH) and 3'(OH) ends by two series of M and L units, B) said units L are obtained by synthesis of a non-nucleotide polymer L

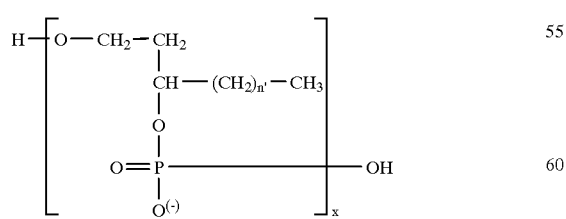

wherein n' and x have the meanings given above, and

C) the said units M are obtained by synthesis of a non-nucleotide polymer M

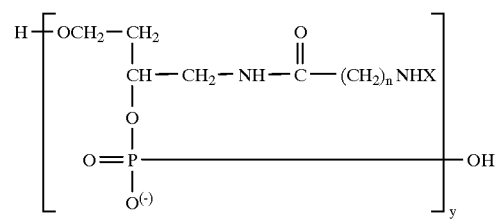

wherein n and y have the meanings given above, and X represents either a marker: alkaline phosphatase, peroxydase, fluorescein, biotin, digoxigenin, any hapten capable of being recognized by antibodies marked in a non-isotopic manner, or a transitory protecting group of the primary amine group which it is intended to remove after total synthesis of the nucleic acid probe I. By way of example only, in this synthesis approach x may denote an acetyl VI, a trifluoroacetyl VII, or a benzoyl VIII

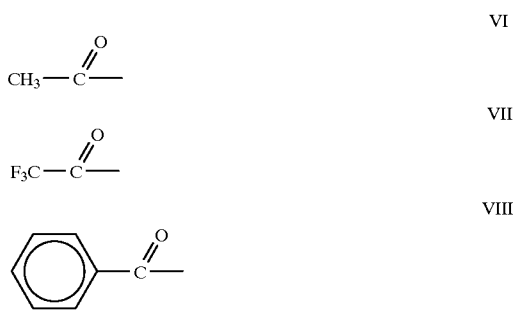

and syntheses B and C above are preferably also carried out using any conventional manual or automatic method of synthesizing an internucleotide linkage, particularly on a solid support.

More particularly, each element of chemical arm L is obtained starting from a 1,3 alkanediol having the formula

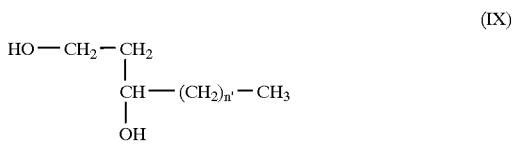

(IX)

by the following steps of a) protecting the primary alcohol group by means of a protecting group $R_1$, so as to obtain a compound of formula

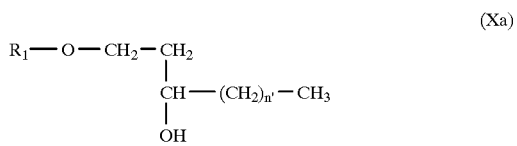

(Xa)

b) transformation of the secondary alcohol group into an $OR_2$ grouping so as to obtain a compound of formula

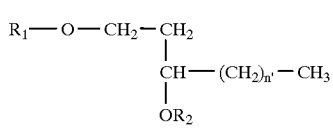
(II)

where $R_2$ represents a group suited to the introduction of compound II (synthon) at the end of a nucleotide or else at the end of an existing synthon.

According to another feature of the invention, each element or unit of detection M is obtained starting from butene-3ol-1 having the formula

(XXX)

by the steps of a) protecting the primary alcohol group by means of a protecting group $R_1$ so as to obtain a compound having the formula

(XXXI)

b) epoxidation of the double bond of compound (XXXI) so as to form a compound of formula

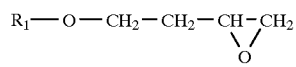
(XIIa)

c) opening of the epoxide by means of ammonia to form a compound of formula

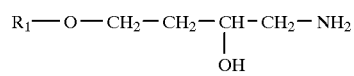
(XIIIa)

d) protecting the primary amino group of a compound of formula

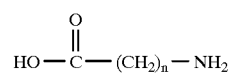
(XXXII)

so as to form a compound of formula

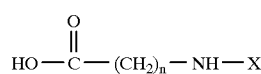
(XXXIII)

wherein X has the meanings given above e) activation of compound (XXXIII)
f) condensation of compounds (XIIIa) and (XXIII) between themselves to form a compound of formula

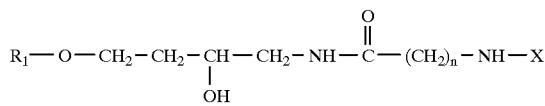
(XVa)

and g) phosphorylation of compound (Xva) so as to form a compound of formula

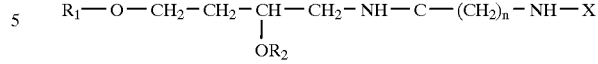
(III)

wherein $R_2$ represents a phosphorylated group suited to the introduction of compound IIIa (synthon) at the end of a nucleotide or alternatively at the end of a synthon already in existence.

In the foregoing formulas, $R_1$ is a protecting group of the primary alcohol group; by way of example only, in the case of synthesis to phosphoramidites on a solid support, $R_1$ may represent the group 4,4'-dimethoxytrityl of formula IV (DMT), which is labile in an acid medium.

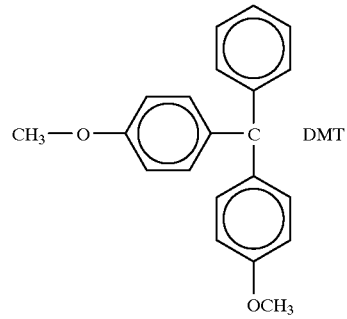
(IV)

and $R_2$ represents H or any possibly protected phosphorylated group suited to the introduction of synthon II or III at the 5' end of a nucleotide or of a synthon, already condensed on the solid support in respect of a given type of internucleotide linkage synthesis.

$R_2$ may represent, by way of example in the case of synthesis to phosphoramidites on a solid support, the group cyanoethoxydiisopropylaminophosphoramidite of formula V.

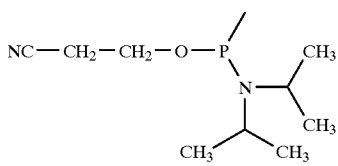
(V)

It is likewise an object of the present invention to provide two non-nucleotide synthetic compounds useful respectively as intermediates for the synthesis of the M and L fragments of compound Ia by any known method of manual or automatic internucleotide linkage synthesis, preferably on a solid support. The two synthetic compounds claimed are represented by formulas II and III,

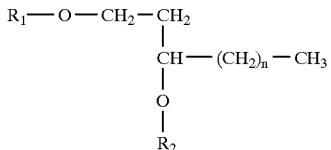
(II)

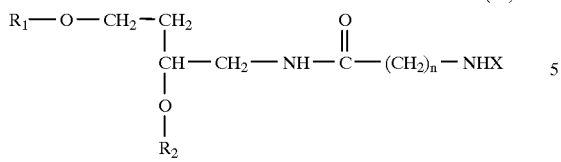

wherein $R_1$, $R_2$, n, n' and X have the meanings given already.

The invention also relates to the preparation of the intermediate compounds II and III by the processes outlined above.

In the case of synthesis to phosphoramidites, the synthesis of compounds II may be represented by the following scheme:

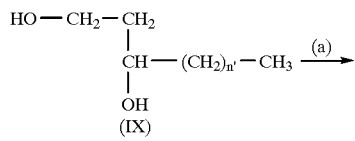

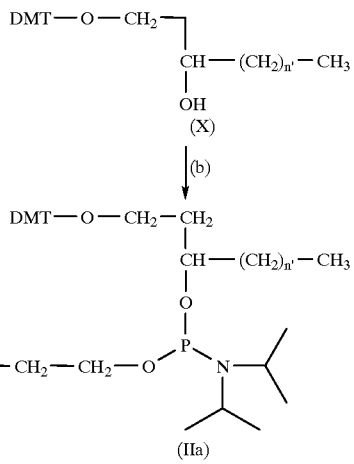

Likewise in the case of synthesis to phosphoramidites, the process for preparing compounds of formula III may be represented by the scheme given below:

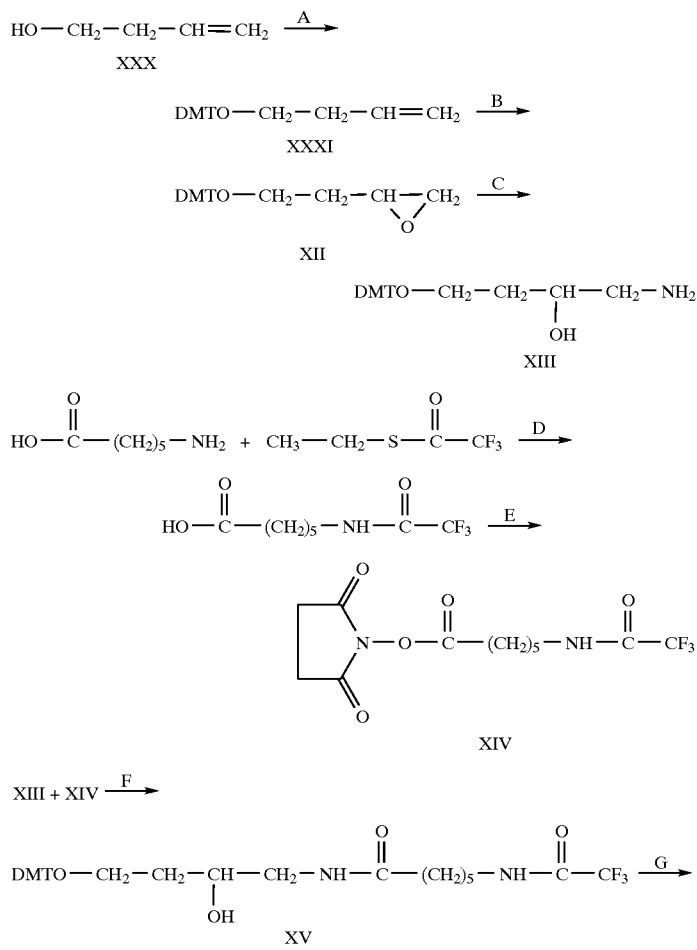

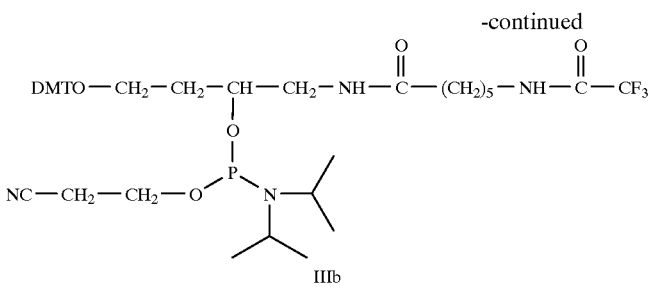

IIIb step A) protection of the butene-3-ol primary alcohol using 4,4'-dimethoxytrityl chloride step B) epoxidation of the double bond using meta-chloroperbenzoic acid step C) opening of the epoxide using ammonia, resulting in compound XIII step D) protection of the 6-aminocaproic acid primary amine by a trifluoroacetyl group step E) activation of 6-trifluoroacetylamidocaproic acid using N-hydroxy-succinimide, resulting in compound XIV step F) preparation of compound XV by condensation between XIII and XIV step G) phosphorylation of secondary alcohol XV with a reagent enabling subsequent splicing in solid phase of the derivative III accordingly obtained by a type of internucleotide linkage synthesis. Phosphorylation, in the case of synthesis to the phosphoramidites, can take place with diisopropylaminocyano-ethoxychlorophosphine M.

A further object of the present invention is a process for functionalizing a CPG (controlled porous glass) solid support by the compound of formula X. The solid support thereby functionalized will make it possible to prepare type I nucleic acid probes in which z is not zero, in other words in which a marker is introduced into the probe at the 3' site. In actual fact, any known method of manual or automatic internucleotide linkage synthesis, preferably on a solid support, works by elongating the chain being formed from the 3' end towards the 5' end.

In the case of type I nucleic acid probes in which z is not zero, it is therefore necessary to begin the synthesis on a solid support functionalized by a compound of formula X or XV. However, given the ease with which derivative X is obtained as compared to compound XV, we have opted to functionalize the support with X.

The claimed method for functionalizing the solid support—the support is initially covered by primary amine groups—comprises the following steps:

acylation of the secondary alcohol of X by succinic anhydride to produce the compound of formula XVII

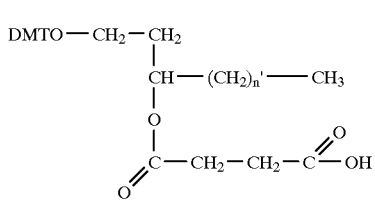

XVII activation of the carboxylic acid group of compound XVII by pentachlorophenol in the presence of carbodiimide to produce the ester XVIII

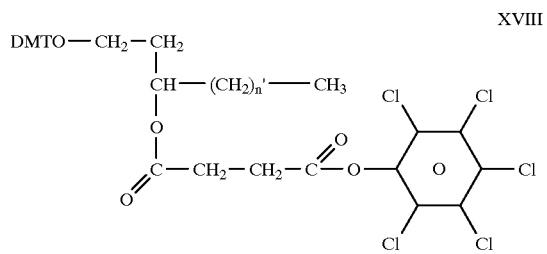

XVIII attachment of the derivative XVIII to an aminated solid support. The functionalized solid support XX is accordingly obtained.

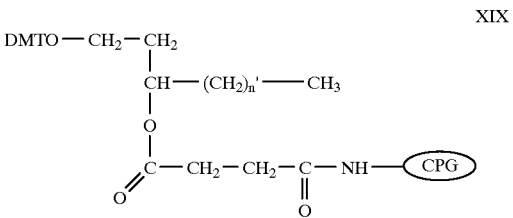

XIX

II. Nucleic Acid Probes Chemically Modified at 5'(OH) by a "CANDELABRA"-Type Molecular Structure In probes of this type, the nucleotide portion consists of a defined sequence of nucleic acids which is homologous with a target complementary fragment, it provides the stabilization energy and ensures hybridization with the DNA or RNA molecule that is to be detected. It is constituted by a chain of phosphate units interspersed with ribose units.

The portion providing the reactivity which enables the hybrid to be detected, either directly or indirectly, is introduced at the 5'(OH) end of the nucleic acid sequence described above. It is constituted by a branching chain of phosphate units interspersed with alkyl groups:

the alkyl groups on the inside of the branch, i.e. uniting the various phosphate groups, exhibit no particular chemical functionality;

the alkyl groups on the outside of the branching, i.e. terminating the various arms of the branch, have a primary amine group at the end of the chain.

The object of the present invention is therefore a nucleic acid probe XX comprising a DNA or RNA nucleic acid sequence S, characterized in that said sequence S is linked at its 5' end to a marking element M.

The chemical modification therefore takes place at 5'(OH) of the nucleic acid sequence, with the result that formula XX can, for example, be specified as follows:

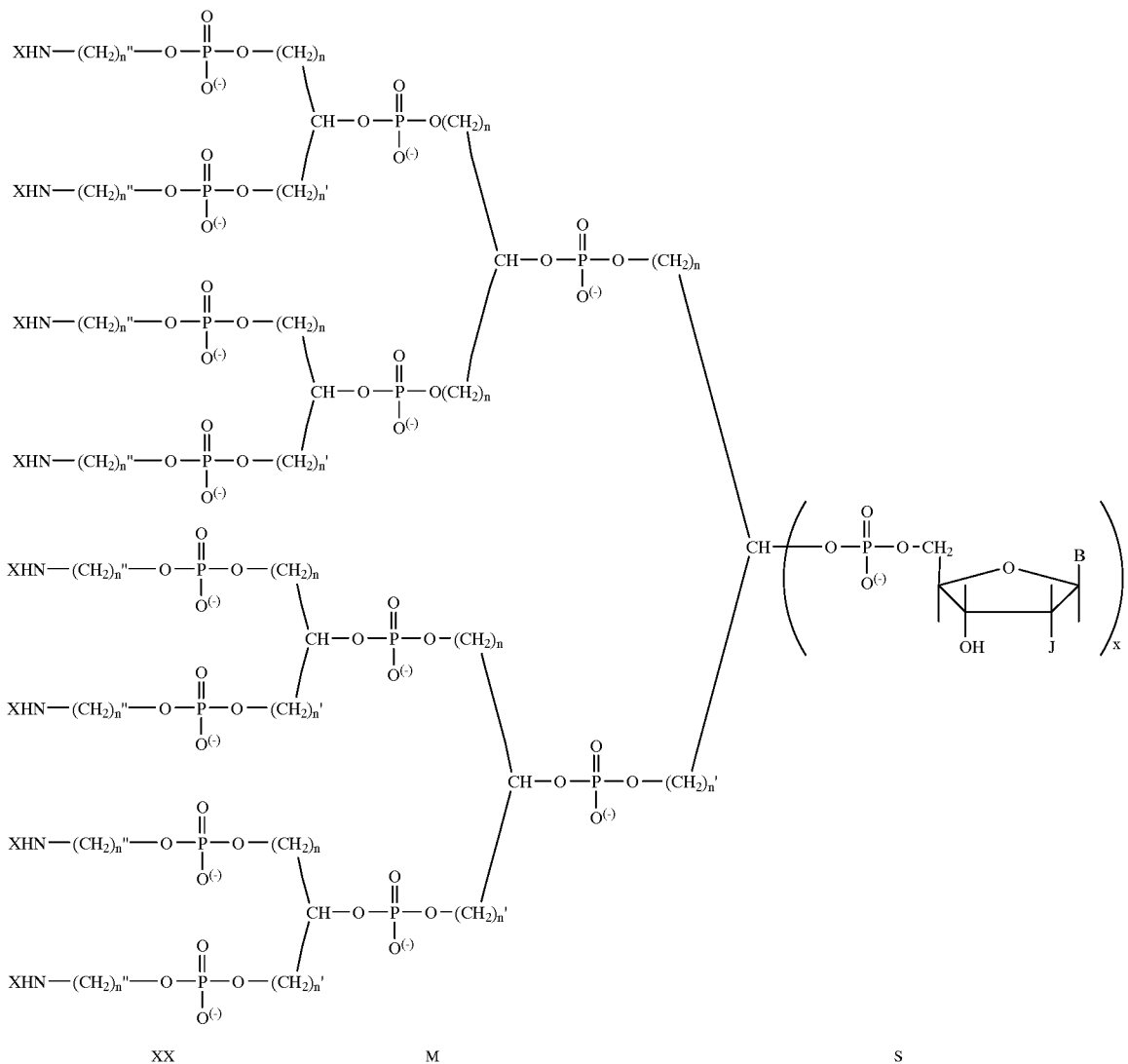

Units S and M may be described as follows:

S: the sequence of nucleic acids
   J—H or OH
   x represents the number of nucleotides from 1 to 1000
   B is the nucleic, purine or pyrimidine base, varying according to the nucleotides.

It will be recalled that nucleic acids are polymers of nucleotides, either ribonucleotides in the case of RNA or deoxyribonucleotides in the case of DNA.

In the case of RNA, the monomers, i.e. the nucleotides, are constituted by phosphoric acid, an ose of carbon atoms, the ribose (J=OH) and one of the four fundamental bases: adenine, guanine, cytosine and uridine. In the case of DNA, the deoxyribonucleotide ose is D-2-deoxyribose (J=H) and the four principal bases are adenine, guanine, cytosine and thymine. One of the essential characteristics of the polynucleotides is the phosphodiester 3'–5' internucleotide bond.

M: marker element, in the example described above terminating in eight aminated arms. From that point it will be referred to as eighth order. The branching order may nevertheless assume values from 2 to 128 (the higher order always being double the preceding one). n, n' and n"=0 to 20

X: marker, either direct: alkaline phosphatase, peroxydase, fluorescein, any enzyme capable in the presence of a substrate of producing a colour or a light; or indirect: biotin, digoxigenin, any hapten capable of being recognized by antibodies marked non-isotopically.

The marker element is a non-nucleotide branched polymer. One of the essential characteristics of this polymer is, with both DNA and RNA, the phosphodiester link between the monomers.

The branched polymer M is constituted from two distinct types of monomers:
   the monomer responsible for constructing the branching structure. This is constituted by phosphoric acid and a triol: UN 1,n, ω alcane triol.
   the monomer responsible for introducing primary amine groups at the branch end. This is constituted by phosphoric acid and an amino alcohol, 1-amino hexane 6-ol.

The synthesis of compound XX may therefore be carried out using conventional internucleotide synthesis, since the different elements of XX are polymers whose monomers are interconnected to each other by phosphodiester bonds.

Another object of the present invention is therefore a method for preparing probes of formulas XX which comprises the synthesis of a nucleic acid sequence S:

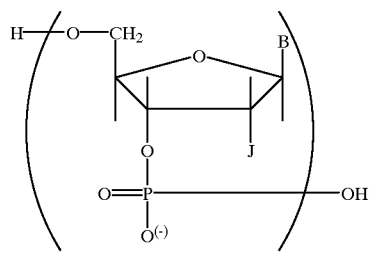

in which B and J have the meanings given above, by any known method of manual or automatic internucleotide linkage synthesis, preferably on a solid support, characterized in that the said sequence is subjected, preferably by the same method of synthesis, viz. on a solid support, to an extension at its 5'(OH) end by a branching molecular structure M whose terminal arms each bear a primary amine group.

The branching molecular structure may satisfy the following formula:

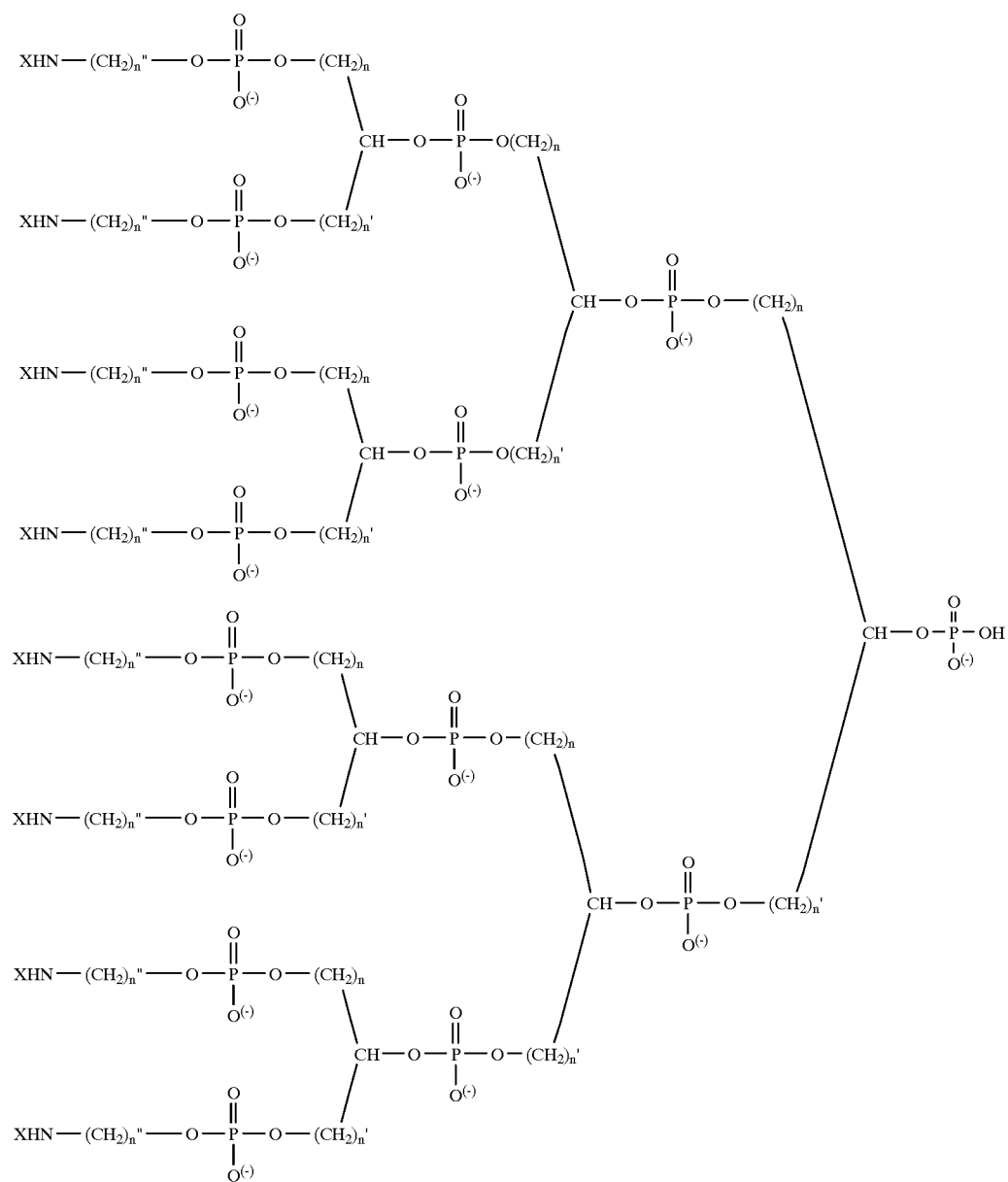

and more particularly may be synthesized by any known method of manual or automatic internucleotide linkage synthesis, preferably on a solid support.

More particularly, the synthesis of the oligonucleotide chain S whose phosphate groups and bases are protected is followed by condensation, at the 5'(OH) end of said chain, of a series of compounds of formula

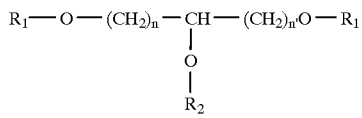  XXI in which $R_1$ and $R_2$ have the meanings already given.

Apart from compound XXI, synthesizing M further requires the use of compound XXII for the introduction of the aminated arms at the branch end.

  XXII

This compound is known in the literature.
In formula XXII,

X represents: either a marker: alkaline phosphatase, peroxydase, fluorescein, biotin, digoxigenin, any hapten capable of being recognized by antibodies labelled non-isotopically;

or a transitory protecting group of the primary amine group which it is intended to remove following the total synthesis of nucleic acid probe XX. By way of example, in this synthesis method X may represent trifluoroacetyl VII, a fluorenylmethoxycarbonyl XXIII.

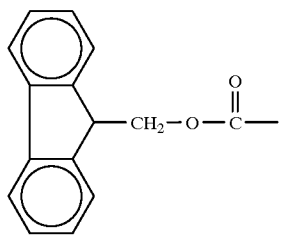  XXIII and $R_2$ has the meanings already given.

In accordance with the invention, the compound of formula XXI is obtained based on an alcanetriol having the formula

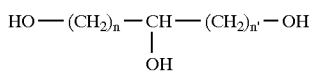  XXIV by the following steps of a) protecting the primary alcohol group by means of an $R_1$ protector group so as to obtain a compound of formula

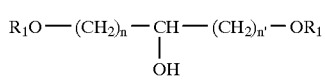  (XXVa)

b) transforming the secondary alcohol group into an $OR_2$ grouping so as to obtain a compound of formula

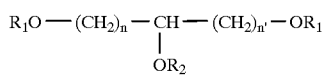  (XXI)

wherein $R_2$ has the meanings already given.

More particularly, in step a) protection is by means of 4,4'-dimethoxytrityl chloride, and in step b) phosphorylation of the secondary alcohol group takes place using diisopropylarinocyanoethoxychlorophosphine (XI).

The invention also relates to compounds of formula XN as intermediates in the synthesis of probes of formula XX, as well as to a method, as described above, for the preparation of the intermediate compounds of formula XXI.

Further features and advantages of the present invention will become apparent from the examples which follow.

EXAMPLE I

Preparation of 1-0-(4,4'-dimethoxytrityl) 3-0-[N,N' diisopropylamino-2cyanoethoxyphosphino]1,3-butanediol The derivative 1-0-(4,4'-dimethoxytrityl) 3-0-[N,N' diisopropylamino, 2cyanoethoxyphos-phino] 1,3-butanediol 1 satisfies the formula:

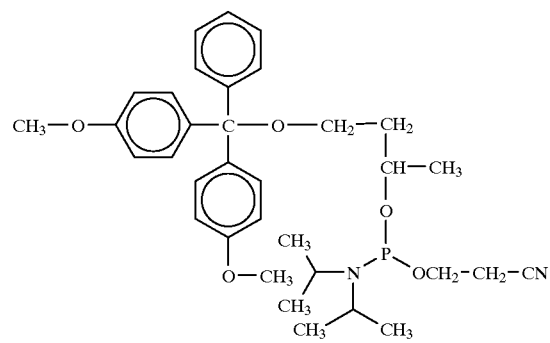

1

The objective of the approach adopted is to prepare a non-nucleotide synthon which does however bear the chemical groups allowing it to be introduced into an oligonucleotide chain or into a non-nucleotide polymer of which the monomers are united by a phosphodiester bond in standard automatic RNA or DNA synthesis conditions. This synthon has the advantage of providing the user with a tool enabling "chemical arms" to be introduced at the 3'(OH) and (or) 5'(OH) sites of a nucleic acid sequence without leaving the automatic or manual synthesis routine. The part played by the chemical arm in this linkage is to introduce spacings between the different marking elements, on the one hand, and between the marking elements and the nucleic acid sequence on the other hand, with a view to achieving greater efficacy of the two parts in their respective hybridization and detection roles.

The 4,4'-dimethoxytrityl and 2-cyanoethoxydiisopropylamino phosphoramidite groups are suited to synthesis with phosphoramidites, and in particular on a solid support.

The chain of reaction in order to obtain compound 1 presented in scheme I below comprises the following stages:

1. Selective protection of the primary alcohol of 1,3-butanediol 2 by the 4,4'-dimethoxytrityl (DMT) group which is labile in an acid pH.

2. Phosphorylation of the secondary alcohol 3. The example of the phosphoramidite shown in the scheme is not limitative; it would equally be feasible to synthesize a phosphate triester or diester or a phosphonate.

two-necked flask. An argon atmosphere is adjusted and then 52 cc of anhydrous tetrahydroftirane and 9 cc (51.9 mmoles) of diisopropylethylamine are added. This is followed by adding to the reaction mixture, drop by drop using a syringe, Scheme I

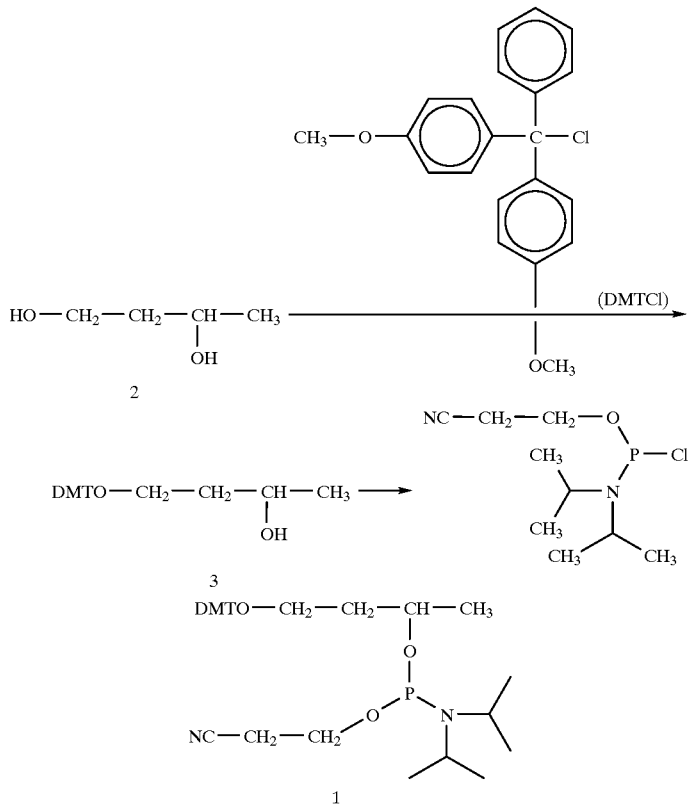

Method for Preparing 1-0-(4,4'-dimethoxytrityl) 1,3-butanediol 3

2.25 g (25 mmoles) of 1,3 butanediol 2 is put into a 100 cc two-necked flask under an argon atmosphere. 40 cc of anhydrous pyridine is added, and then 11 g (32.5 mmoles) of 4,4'-dimethoxytrityl chloride is added to the solution in small portions. This is followed by magnetic stirring for 90 minutes at room temperature and in an argon atmosphere. Next 10 cc of methanol is added to the reaction mixture. The purpose of this operation is to neutralize the excess 4,4'-dimethoxytrityl chloride. The reaction mixture is now hydrolyzed (100 cc of 5% NaHCO$_3$), extracted twice with dichloromethane (CH$_2$Cl$_2$—two times 75 cc). The resulting organic phase is washed three times with a 5% sodium bicarbonate solution (5% NaHCO$_3$). The organic phase is then dried over magnesium sulphate (MgSO$_4$), filtered and then evaporated (rotary evaporator p=20 mm Hg).

The residue is purified on a Merck 9385 silica column using CH$_2$Cl$_2$ as the eluant. The silica is previously neutralized by suspending it in a solution of CH$_2$Cl$_2$ containing 1% diisopropylethylamine (DIEA). After purification 6.79 g of compound 3 (17.32 mmoles) is recovered—yield 69%.

Thin layer chromatography on a Merck 5735 plate (silica gel 60F$_{254}$), eluant CH$_2$Cl$_2$: final ratio=0.3.
Method for Preparing 1-0-(4,4'-dimethoxytrityl) 3-0-[N,N' diisopropylamino)-2-cyanoethoxyphosphino]1,3-butanediol 1

6.7 g of compound 3 (17.3 mmoles) is placed in a 100 cc 5.52 g (23.35 mmoles, 5 cc) of 2-cyanoethoxydiisopropylmino chlorophosphine.

After ten minutes reaction time, a substantial precipitate appears within the reaction mixture (diisopropylethylamine hydrochloride). This precipitate is filtered, 100 cc of ethyl acetate is added to the filtrate, the organic phase thereby obtained is washed three times with a solution of 5% NaHCO$_3$. The organic phase is then dried over MgSO$_4$, filtered and evaporated (rotary evaporator, p=20 mm Hg). The residue is purified on a Merck 9385 silica column—using 4-hexane 6 ethyl acetate as eluant. The silica has previously been neutralized by suspending it in eluant containing 1% DIEA. Following purification 9.24 g of compound 1 is recovered. Yield 90%.

Thin layer chromatography on a Merck 5735 plate (silica gel 60F$_{254}$), eluant 5-hexane 5 ethyl acetate. Final ratio: 0.8 (the starting substance of this reaction 3 a, in these conditions, a final ratio of 0.5).

EXAMPLE II

Preparation of 1-0-(4,4'-dimethoxytrityl)3-0-(N,N'-diisopropylamino 2-cyanoethoxyphosphino) 4-amido-(6-trifluoroacetvlamido) caproate 4-amino 1.3-butanediol 4

The derivative 1-0-(4,4'-dimethoxytrityl)3-0-(N,N'-diisopropylamino 2-cyanoethoxyphos-phino) 4-amido-(6-trifluoroacetylamido) caproate 4-amino 1.3-butanediol 4 satisfies the formula:

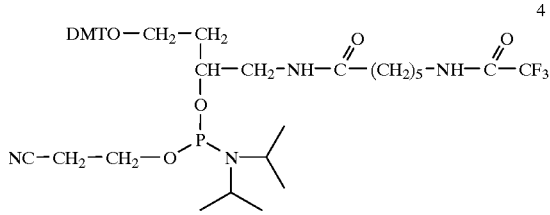

The objective of the approach adopted is to prepare a non-nucleotide synthon which does however bear the chemical groups allowing it to be introduced into an oligonucleotide chain or into a non-nucleotide polymer of which the monomers are united by a phosphodiester bond in standard automatic or manual RNA or DNA synthesis conditions.

This system has the advantage of providing the user with a tool enabling one or more non-isotopic marking elements to be introduced at the 3'(OH) and (or) at 5'(OH) site of a nucleic acid sequence, without leaving the automatic or manual synthesis routine. The marking elements are separated by "chemical arms" from the oligonucleotide chain on the one hand, and from one another on the other hand. The direct role of the marking element as described in this example is to introduce "primary amine" arms separated from one another by "chemical arms" at the 5'(OH) and (or) 3'(OH) sites of an oligonucleotide chain. Their nucleophilic nature renders these aminated arms capable of subsequently attaching a direct or indirect detection element (enzyme, fluorescein, biotin, digoxigenin, etc.).

The 4,4'-dimethoxytrityl and N,N' diisopropylamino 2-cyanoethoxy phosphoramidite groups are suited to synthesis with phosphoramidites.

The reaction path to obtain compound 4 presented in scheme II-below comprises the following stages:

1. Protection of the alcohol of 3-butene 1-ol 5 with 4,4'-dimethoxytrityl (DMT) labile in an acid pH.

2. Epoxidation of terminal olefin 6 using metachloroperbenzoic acid.

3. Opening of epoxide 7 using ammonia.

4. Protection of the primary amine of 6-aminocaproic acid using the trifluoroacetyl group.

5. Activation of the carboxylic acid of derivative 9 in N-hydroxysuccinimic ester 10.

6. Condensation between compound 8 and compound 10.

7. Phosphorylation of secondary alcohol 11. The example of the phosphoramidite shown in the scheme is not limitative. Equally feasible would be the synthesis of a phosphate triester or diester or of a phosphonate.

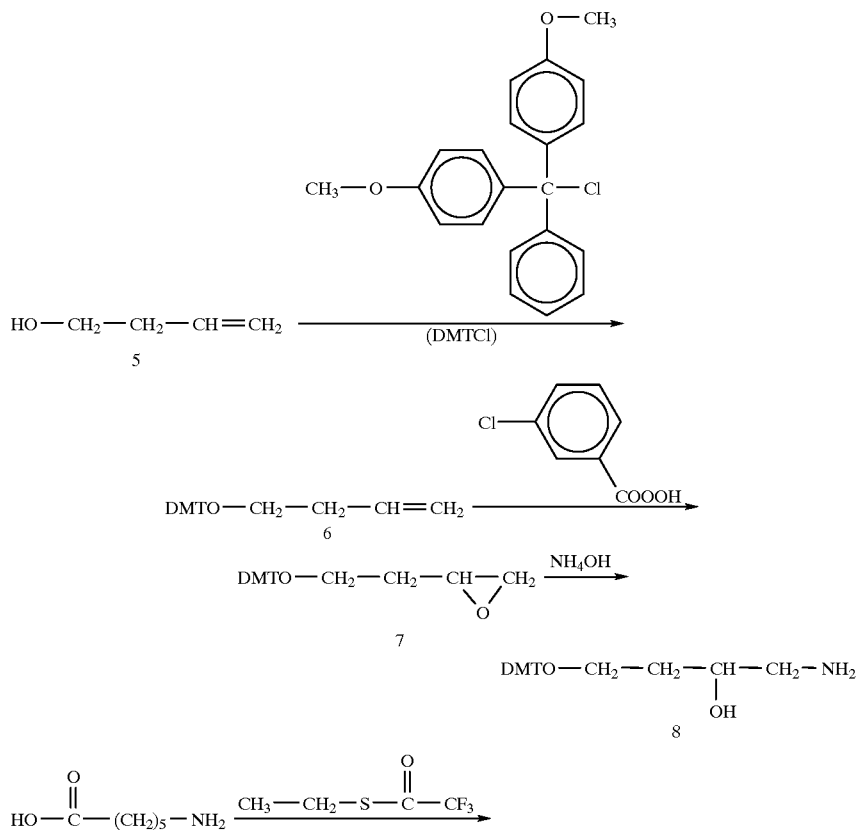

Scheme II

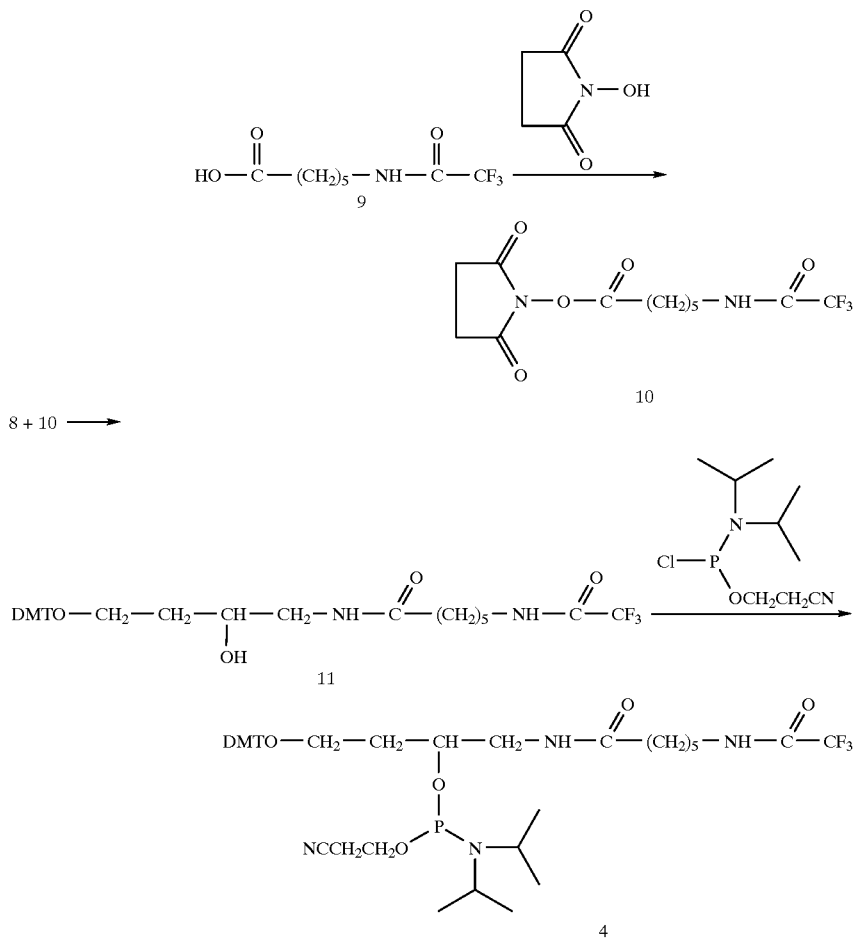

Method for Preparing 1-0-(4,4'-dimethoxytnityl) 3-butene 1-ol 6

Into a 250 ml two-necked flask is placed 3.6 g (50 mmoles) of 3-butene 1-ol under argon, in solution in 80 cc of anhydrous pyridine. 22 g (65 mmoles) of 4,4'-dimethoxytrityl chloride is introduced in small portions (the reaction is slightly exothermic).

This is kept at room temperature for 4 hours and stirred magnetically throughout. 10 cc of methanol is then added to the reaction mixture in order to neutralize the excess 4,4'-dimethoxytrityl chloride. The reaction mixture is then hydrolyzed with 100 cc of 5% NaHCO3. The mixture is extracted twice with 150 cc of dichloromethane. The resulting organic phase is washed three times with 5% $NaHCO_3$, three times with water and once with an aqueous solution saturated in NaCl. The resulting organic phase is dried over $MgSO_4$, filtered and evaporated (rotary evaporator p=20 mm Hg).

The residue obtained is then coevaporated with toluene in order to azeotropically strip away the residual pyridine, then coevaporated with dichloromethane in order to azeotropically strip away the residual toluene. The residue is then purified on a Merck 9385 silica column, eluant:hexane 1-dichloromethane-9. The silica is previously neutralized by suspending it in the eluant containing 1% DIEA. Compound 6 is obtained with a yield of 90%.

Thin layer chromatography on a Merck 5735 plate (silica gel $60F_{254}$), eluant dichloromethane, Final ratio: 0.85.

Method for Preparing 1-0-(4,4'-dimethoxytrityl) 3,4-butene oxide 7

Commercial m-chloroperbenzoic acid contains 50% water; in order to remove this water, it is placed in solution in dichloromethane and the water is removed by decanting. Into a 100 cc Erlenmeyer flask is introduced 8.5 g of 50% m-chloroperbenzoic acid (24.6 mmoles), and this is placed in solution in 64 cc of dichloromethane. The supernatant aqueous phase is decanted. Into a 250 cc flask is put 6.35 g of compound 6 (17 mmoles) under an argon atmosphere. This is placed in solution in 40 cc of dichloromethane. Next the peracid solution prepared as described above is slowly added. The reaction mixture is stirred magnetically for 8 hours. The precipitate which has formed is then filtered (m-chlorobenzoic acid). 150 cc of dichoromethane is added to the filtrate and this is hydrolyzed with 75 cc of 5% $NaHCO_3$. The organic phase is washed four times with 75 cc of 5% $NaHCO_3$, then dried over $MgSO_4$, filtered and evaporated (rotary evaporator p=20 mm Hg). The residue is purified on a Merck 9385 silica column—eluant hexane 2—dichloromethane 8. The silica is previously neutralized by suspending it in the eluant containing 1% DIEA. After purification, 5.32 g of epoxide 7 is obtained, yield 80%.

Method for Preparing 1-0-(4,4'-dimethoxytrityl) 4- amino 1,3-butanediol 8

Into a 25 cc pyrex flask fitted with a screwed stopper and capable of withstanding high pressures are introduced 3 g (7.6 mmoles) of epoxide 7, 10 cc of acetonitrile and 25 cc of 32% ammona. The mixture is heated for 8 hours at 60° C. and then the water and acetonitrile are evaporated. The residue obtained is purified on a Merck 9385 silica column, eluant $CH_2Cl_2$—$CH_3OH$, the proportion of methanol is progressively brought from 2% to 10%. The silica is previously neutralized by suspending it in the starting eluant containing 1% DIEA. After purification, derivative 8 is obtained with a 75% yield. Thin layer chromatography on a Merck 5735 plate, silica gel 60$F_{254}$—eluant 20% $CH_3OH$—80% $CH_2Cl_2$. Final ratio: 0.2.

Method for Preparing 6-4trifluoroacetymidocaproic acid 9

Into a 50 cc Rotavapor flask is introduced 2.62 g ($2\times10^{-2}$ moles) of 6-amnoinocaproic acid. This is suspended in 4 cc of anhydrous dimethylformarnde, and then 3 cc ($2.35\times10^{-2}$ moles) of S-ethyl trifluoro thioacetate is added to the suspension. An argon atmosphere is adjusted and the mixture is stirred for 4 hours, after which time the solution is clear. The dimethylformamide is evaporated at reduced pressure (P=20 mm Hg). The residue is crystallized in dichloromethane. Compound 9 is obtained with an 84% yield. Thin layer chromatography (TLC) on a Merck 5735 plate, silica gel 60$F_{254}$—eluant 20% $CH_3OH$—80% $CH_2Cl_2$. Final ratio: 0.5.

Method for Preparing 6-trifluoroacetamido caproate of N-hydroxysuccinimide 10

Into a 100 ml flask are introduced 2.27 g ($10^{-2}$ mole) of compound 9, 2.04 g ($10^{-2}$ mole) of dicyclohexylcarbodiimide and 1.15 g ($10^{-2}$ mole) of N-hydroxysuccinimide. 40 cc of $CH_2Cl_2$ is added and the mixture is stirred for 5 hours in an argon atmosphere. A white precipitate forms, and this is filtered. The filtrate is evaporated. The residue obtained exhibits only a single spot in thin layer chromatography, it is not purified, and the yield is quantitative. Thin layer chromatography—Merck 5735 plate, silica gel 60$F_{254}$—eluant 5% $CH_3OH$—95% $CH_2Cl_2$. Final ratio: 0.7.

Method for Preparing 1-0-(4,4'-dimethoxytrityl) 4-amido (6-trifluoroacetylamido) caproate 4-amino 1.3-butanediol 11

In an argon atmosphere 2.44 g (6 mmoles) of compound 8 and 3.44 g of compound 10 (9.45 mmoles) are put into a 50 cc two-necked flask. A solution is produced using 25 cc of anhydrous dimethylformamide and this is stirred for 16 hours. The dimethylformamide is then evaporated at reduced pressure (P=20 mm Hg) in the Rotavapor. The residue is purified on a Merck 9385 silica column, eluant 5 hexane—95 $CH_2Cl_2$, and then $CH_3OH$ $2\rightarrow10$—$CH_2Cl_2 98\rightarrow90$. The silica is previously neutralized by suspending it in the initial eluant containing 1% DIEA. After purification, compound 11 is obtained with a yield of 84%. Thin layer chromatography (TLC)—Merck 5735 plate, silica gel 60$F_{254}$—eluant 10% $CH_3OH$—90% $CH_2Cl_2$. Final ratio: 0.8.

Method for Preparing 1-0-(4,4'-dimethoxtrityl) 3-0-(N,N' diisopropylamino 2-cyanoethoxyphosphino) 4-amido-(6-trifluoroacetylamido) caproate 4-amino 1.3-butanediol 4

In an argon atmosphere 2 g (3 mmoles) of derivative 11 is put into a 50 cc two-necked flask. To this are added 17 ml of anhydrous tetrahydrofurane, 1.6 cc of diisopropylethylamine and 0.88 cc (4.1 mmoles) of N,N' diisopropylamino 2-cyanoethoxychlorophosphine. The solution is stirred for 1 hour at room temperature, and then 25 cc of ethyl acetate and 20 cc of 5% $NaHCO_3$ is added. The resulting organic phase is now washed three times with 5% $NaHCO_3$, it is dried over $MgSO_4$, filtered and then evaporated under vacuum (P=20 mm Hg). The residue is purified on a Merck 9385 silica column; eluant hexane 15—ethyl acetate 85. The silica is previously neutralized by suspending it in the eluant containing 1% DIEA. After purification, derivative 4 is obtained with a yield of 62%. Thin layer chromatography (TLC)—eluant hexane 10—ethyl acetate 90. Final ratio: 0.75.

EXAMPLE III

Investigation into the Reactivity of Derivatives 1 and 4

The non-nucleotide phosphoramidites 1 and 4 can be used to introduce at 5'(OH) and (or) at 3'(OH) of an oligonucleotide, respectively:

chemical arms (derivative 1)
"primary amine" arms (derivative 4).

The "primary amine" arms are separated from one another and separated from the oligonucleotide chain by chemical arms.

With the objective of realising such biopolymeric structures, the reactivity of compounds 1 and 4 was tested in standard automatic DNA or RNA synthesis conditions.

To this end, derivatives 1 and 4 were condensed in the automatic synthesis apparatus for oligonucleides; they were condensed at 5'(OH) of a thymidine-thymidine (T-T) dimer attached to a solid support (CPG support-controlled porous glass, the conventional support in automatic synthesis).

If the aminated arm originating from the condensation of a unit 4 is designated N, and the chemical arm originating from the condensation of a unit 1 is designated S, the modified T-T dimers at 5'(OH) which have been synthesized are as follows:

| NTT | 12 |
|------|----|
| STT | 13 |
| NSTT | 14 |
| SNSTT | 15 |

Derivatives 1 and 4 successfully attach at 5'(OH) on an elongated oligonucleotide (cf. NTT, STT). Compound 4 successfully attaches after a chemical arm (cf. NSTT) and compound 1 safely attaches after an aminated arm (cf. SNSTT).

All the conditions (splicing time, concentration of reagents and solvents) routinely used in the course of an olignonucleotide elongation cycle proved suitable as far as the condensation of 1 is concerned.

Nonetheless, for the condensation of 4 it did prove necessary to optimize the conditions routinely used (phosphoramidite concentration 0.1M and condensation time 25 sec). This is because derivative 4 condenses with a quasi-quantitative yield if a 0.1M concentration of phosphoramidite and a condensation time of 10 minutes are used.

In each of the four condensation trials carried out, the product obtained was, to all intents and purposes, pure, as can be seen from the results of capillary electrophoresis analysis (FIG. 1). These results show that the reactions of condensation, oxidation, capping and cleavage of the solid support after synthesis are efficient and do not degrade the trimers (NTT, STT), tetramers (NSTT) and pentamers (SNSTT) formed. Furthermore, in oligonucleotide synthesis it is possible to recover the solution deprotecting the dimethoxytrityl group and to measure the intensity of the orange coloration of the cation in order to be able to assess the yield of each condensation. These measurements were done for the S and N condensations, and they indicate quasi-quantitative yields.

The instability of the amine protecting group (trifluoroacetyl group) was likewise investigated. In actual fact, the conventional conditions for cleavage of an oligonucleotide chain from the solid support ($NH_4OH$ 32%, 1 hr, RT) and the conventional conditions for deprotecting the base phosphates and amines of the oligonucleotide chain (32% $NH_4OH$, 8 hrs, 55° C.) proved to be sufficient for deprotecting the primary amine introduced into polymers 12, 14 and 15 by condensation of a monomer 4.

Solid Phase Splicing of Derivative 1 or Derivative 4 to a Thymidine-Thymidine Dimer Attaching to an Insoluble Solid Support Derivative 1, or derivative 4, solubilized in anhydrous acetonitrile at a concentration of 0.1M is activated with 0.5M tetrazole in the same solvent and condensed with the hydroxyl group at the 5' site of a thymidine-thymidine dimer attaching to an insoluble solid support routinely used in oligonucleotide synthesis in an ABI 394 synthesizer. As far as the condensation of compound 1 is concerned, all the conditions are identical to those employed in an oligonucleotide elongation cycle (N. D. Sinha, J. Biernat, J. McManus and H. Koester, Nucleic Acids Research (1984), 12(11), 4539).

As to the condensation of compound 4, all the conditions are identical to those employed in an oligonucleotide elongation cycle, with the exception of the splicing time which is extended to 10 minutes whereas it is 25 seconds under conventional splicing conditions.

Cleavage of the solid support is performed in standard conditions (32% $NH_4OH$) and the end product is obtained with a yield comparable to those currently being achieved in oligonucleotide synthesis.

The synthesized trimers, tetramers and pentamers 12, 13, 14 and 15 were analyzed by capillary electrophoresis (cf. FIG. 1) ABI 270A, MICRO-GEL 100 capillary column, internal diameter 50 μm, length 50 cm, voltage 15 kV, 75 mM Tris-phosphate 10% methanol buffer, pH 7.6.

EXAMPLE IV

Preparation of Oligodeoxyribonucleotide Mixed Molecules Bearing at 5'(OH) a Linear Tangle of Chemical Arms Interspersed with Aminated Arms Useful in the Detection of DNA Sequences by Non-Radioactive Methods The synthesis and utilisation of mixed molecules composed of an oligonucleotide part and another part possessing characteristic chemical properties allows easy and rapid detection of target deoxyribonucleic acids by non-radioactive methods. The oligodeoxyribonucleotide part of defined sequence homologous with a target DNA fragment provides the stabilization energy and ensures its hybridization with the DNA molecule that is to be detected. The part that provides the reactivity allowing direct or indirect detection of the hybrid can be introduced at the 5'(OH) and (or) 3'(OH) end of the nucleic acid sequence. In this specific example, the part responsible for the detection will essentially be introduced at 5'(OH) of the nucleic acid sequence.

The part responsible for detection will be introduced at 5'(OH) of the oligonucleotide chain still attaching to the solid support and protected over its bases and its phosphates by preceding to a series of condensations of derivatives 1 and 4 using the same reaction cycles in the automatic DNA synthesizer as those employed for synthesis of the nucleic acid sequence. However, in respect of derivative 4 the condensation time will be extended to 10 minutes instead of the 25 seconds employed in the conventional cycle.

After cleavage of the 5' modified oligonucleotide chain from its solid support, and deprotection of the bases and phosphates, the part that provides the reactivity responsible for detection will be introduced via a covalent chemical bond. Out of the various molecules possessing the requisite properties for detection, those preferred are biotin, digoxigenin, fluoreescein, peroxydase and alkaline phosphatase. These molecules, judiciously activated, are attached to the oligonucleotide chain at the primary amines introduced for that purpose because of their nucleophilic nature.

If the aminated arm originating from the condensation of a unit 4 is designated N, and the chemical arm originating from the condensation of a unit 1 is designated S, the modified oligomers at 5'(OH) which have been synthesized are as follows:

| | |
|---|---|
| NSSTTTTCAAAGAAGATGGCAAAACA | 16 |
| NSSNSSTTTTCAAAGAAGATGGCAAAACA | 17 |
| NSSNSSNSSTTTTCAAAGAAGATGGCAAAACA | 18 |
| NSSNSSNSSNSSTTTTCAAAGAAGATGGCAAAACA | 19 |

Figure 2A:
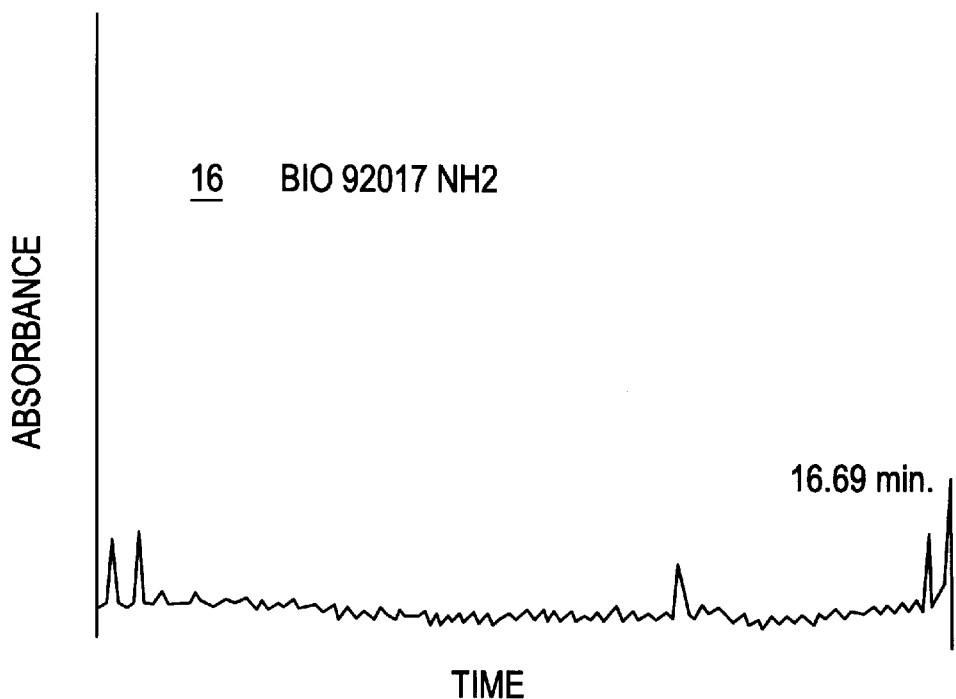
Figure 2B:
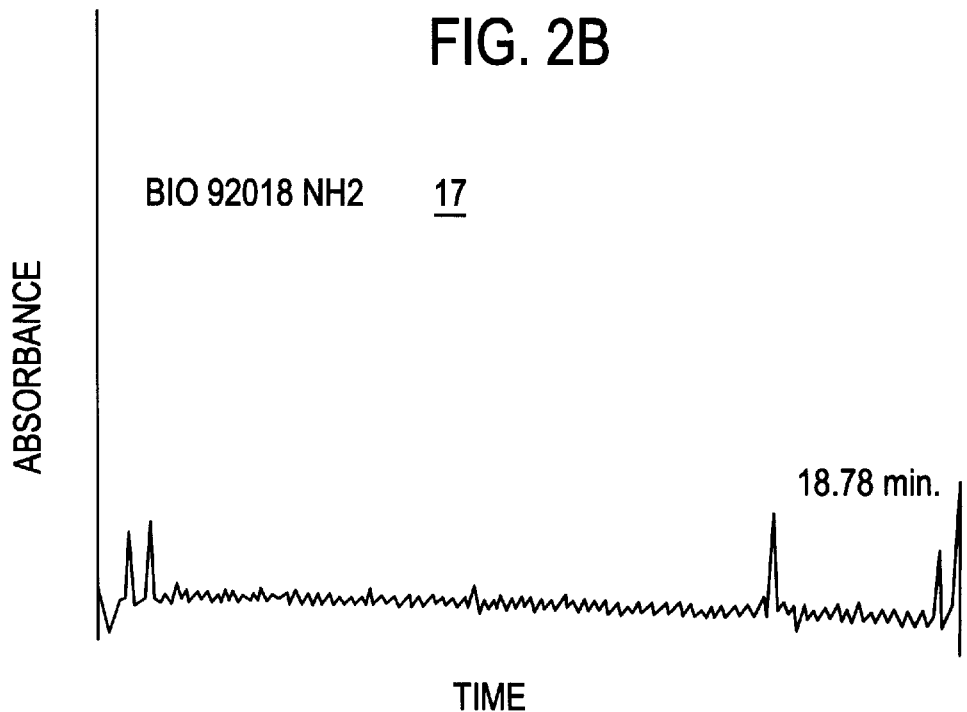
Figure 2C:
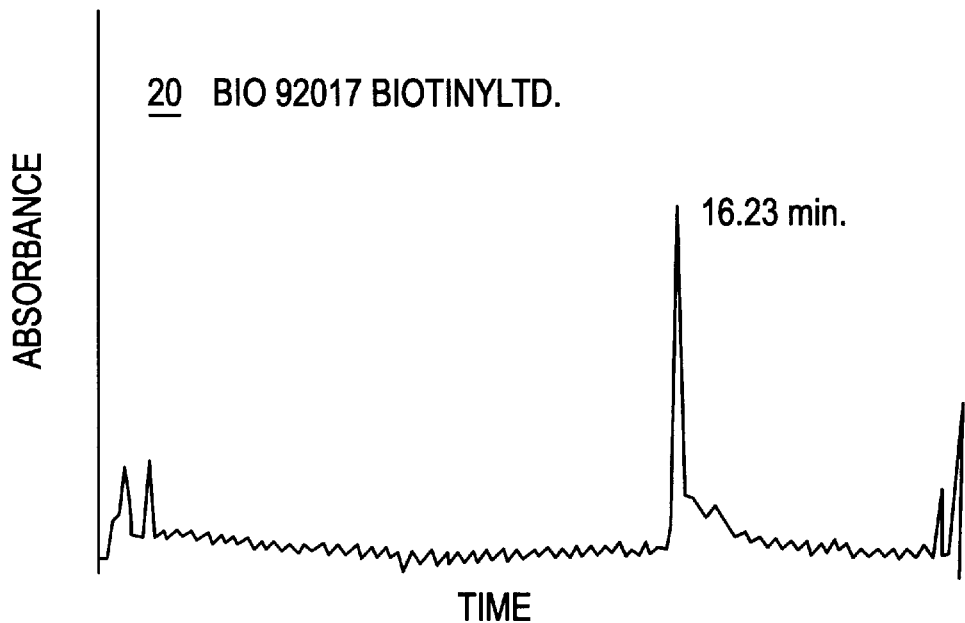
Figure 2D:
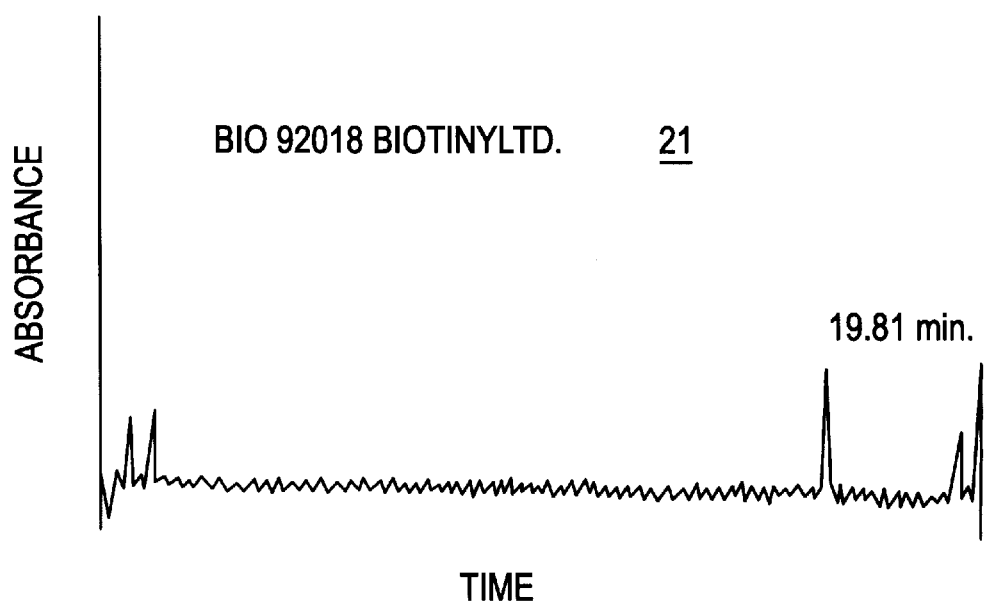
Figure 2E:
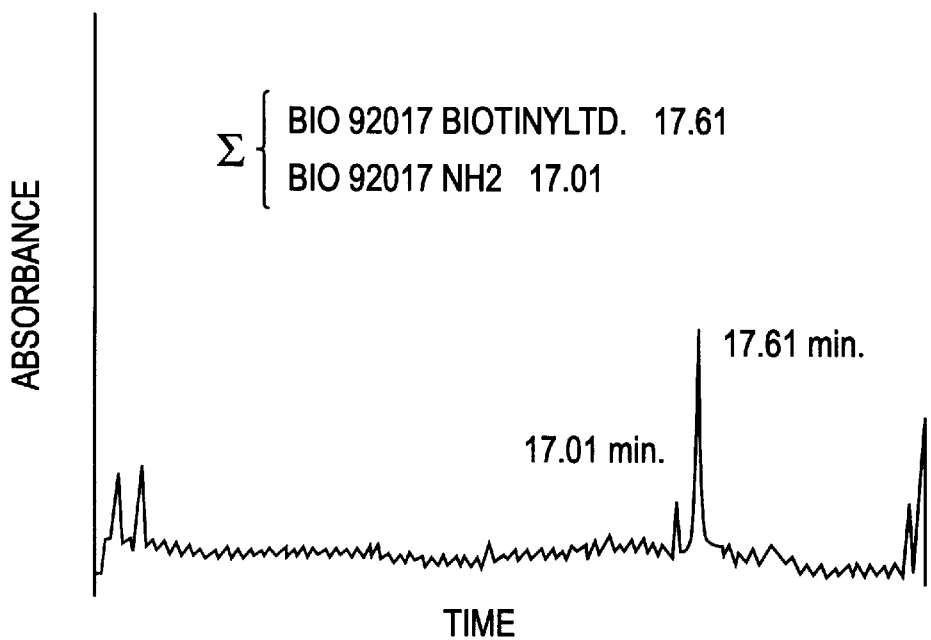
Figure 2F:
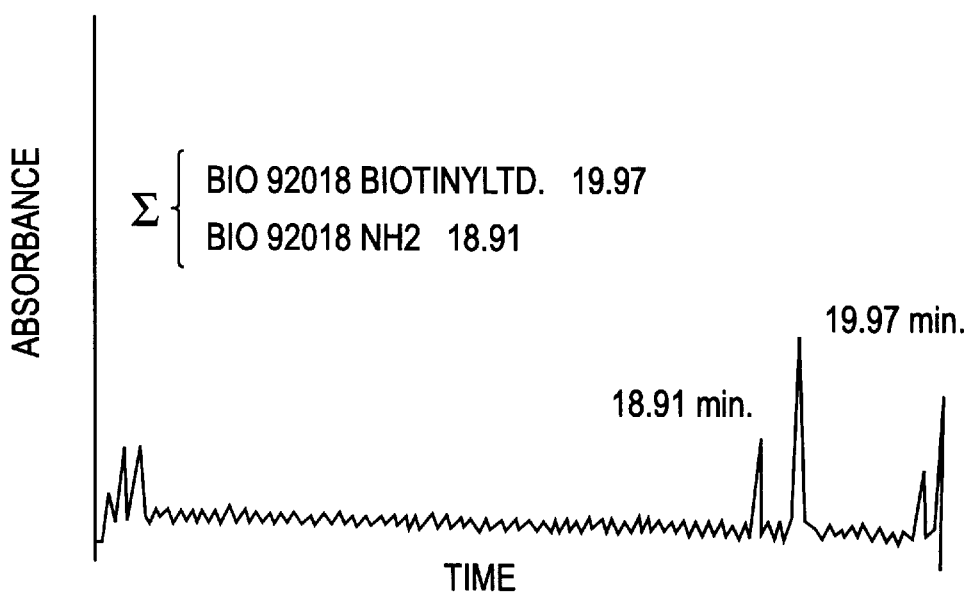
Figure 2G:
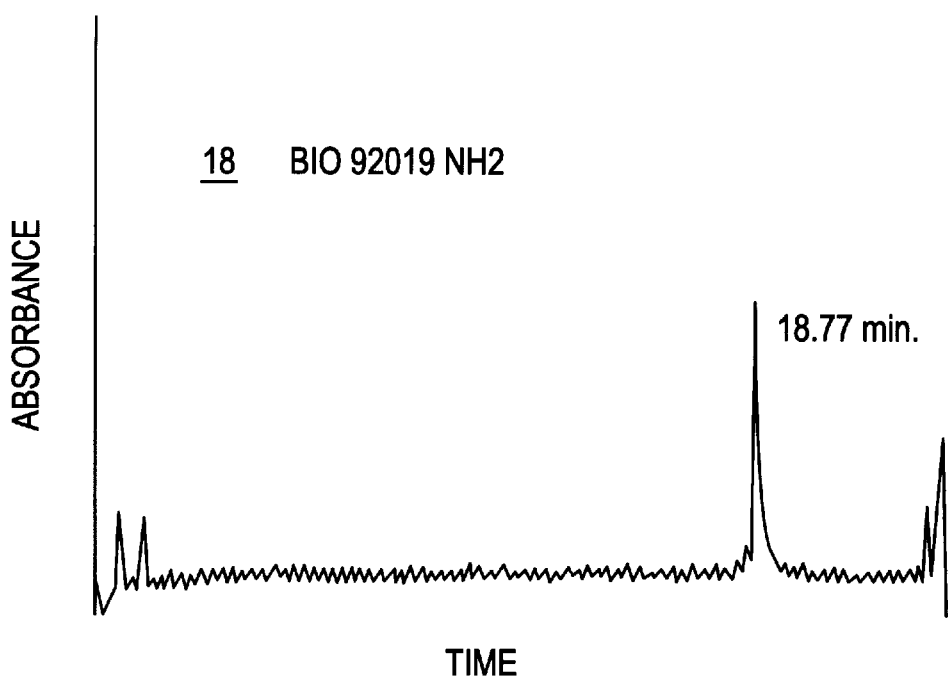
Figure 2H:
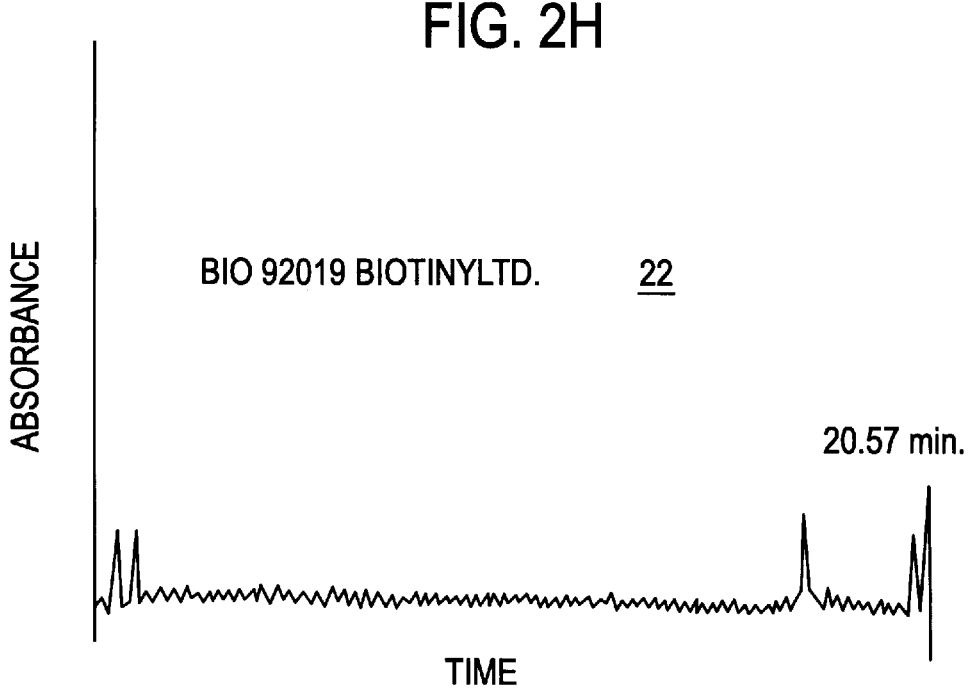
Figure 21:
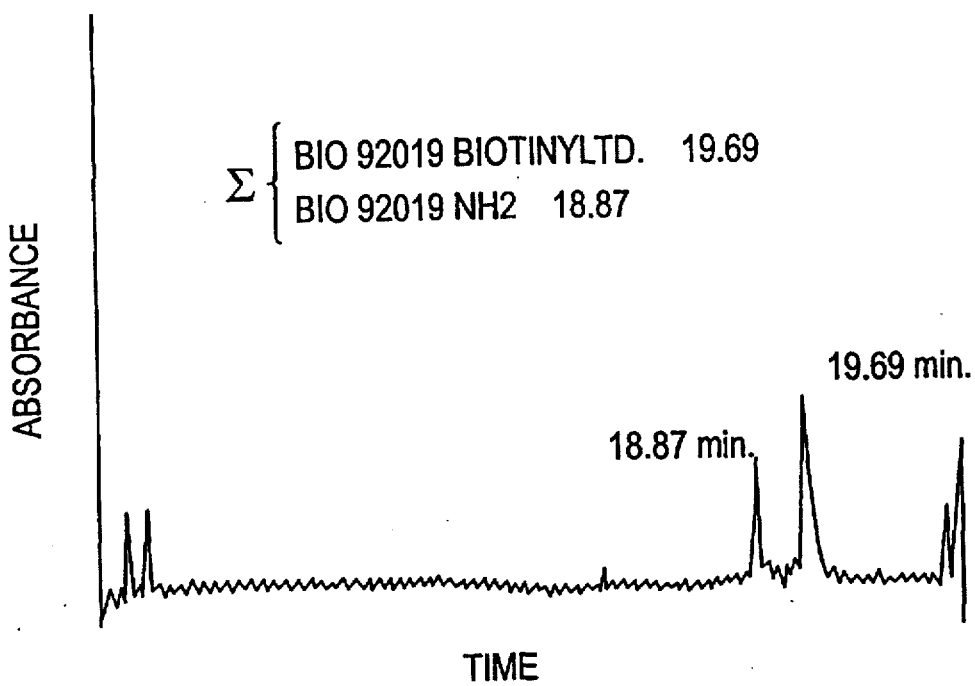

After cleavage of the accordingly modified oligonucleotide chain from its solid support and deprotection of the bases and phosphates, probes 16, 17, 18 and 19 are biotinylated so as to produce biotinylated probes 20, 21, 22 and 23 which are analyzed by capillary electrophoresis (see FIGS. 2a and 2b).

If the aminated arm originating from the condensation of a unit 4 followed by biotinylation is designated B, and the chemical arm originating from condensation of a unit 1 is designated S, the monobiotinylated or polybiotinylated probes at 5'(OH) which are obtained are as follows:

| | |
|---|---|
| BSSTTTTCAAAGAAGATGGCAAAACA | 20 |
| BSSBSSTTTTCAAAGAAGATGGCAAAACA | 21 |
| BSSBSSBSSTTTTCAAAGAAGATGGCAAAACA | 22 |
| BSSBSSBSSBSSTTTTCAAAGAAGATGGCAAAACA | 23 |

See FIGS. 2a and 2b.
Method for Preparing Oligodeoxyribonucleotide Mixed Molecules Bearing at 5'(OH) a Linear Tangle of Chemical Arms Interspersed with Aminated Arms 16. 17, 18 and 19

A DNA probe was synthesized with a complementary oligodeoxynucleotide sequence of a target sequence. In solid phase, in an ABI 394 automatic DNA synthesizer, four identical probes having the sequence 5' TTTTCAAAGAA-GATGGCAAAACA 3' are simultaneously prepared (in four reactors).

The synthesizer is programmed to continue cycles of attachment at 5' of units 1 and 4 to respectively obtain the biopolymers 16, 17, 18 and 19. This involved the use of 6 mg of CPG support functionalized with dimethoxytrityl isobutyl guanosine at 34 μmoles/g, which corresponds to 0.2 μmole. Derivative 1 and derivative 4 are solubilized in anhydrous acetonitrile at a 0.1M concentration and introduced into the synthesizer at the locations provided for non-conventional phosphoramidites.

After automatic synthesis of biopolymers 16, 17, 18 and 19, the oligonucleotide chains accordingly modified are cleaved from the CPG supports by four successive 15-minute treatments with 500 μl of 32% $NH_4OH$. The ammonia solutions obtained are maintained at 55° C. for 5 hrs. The object of this second treatment is to deprotect the bases and phosphates of the oligonucleotide chains. The ammonia solutions are lyophilized, the four residues are subjected to molecular filtration chromatography (G50 Sephadex gel), followed by electrophoresis on 20% polyacrylamide gel.
Method for Biotinylation of Oligodeoxyribonucleotide Mixed Molecules Bearing at 5'(OH) a Linear Tangle of Chemical Arms Interspersed with Aminated Arms. Preparation of Biotinylated Probes 20, 21, 22 and 23

20DO of aminated probe 16, 17, 18 or 19 is dissolved in 120 μl of 0.01M phosphate buffer pH 7.5 in an Eppendorf tube, A solution of 20 mg of sulfosuccinimidyl 6-biotinamidocaproate in 240 μl of dimethylformamide is added. This is incubated at room temperature for 16 hrs. Each solution is subjected to molecular filtration chromatography (G50 Sephadex gel), and then to electrophoresis on 20% polyacrylamide gel. The biotinylated probes 20, 21, 22 and 23 were analyzed by capillary electrophoresis on a Micro-Gel$_{100}$, internal diameter 50 μm, length 50 cm, voltage 15 kV, buffer 75 mM Tris-phosphate—10% methanol pH 7.6.

EXAMPLE V

Preparation of a CPG Solid Support Functionalized by 1-0-(4,4' Dimethoxytrityl) 1.3-butanediol The CPG support functionalized by 1-0-(4,4' dimethoxytrityl) 1.3-butane-diol 3 is represented by the formula 24

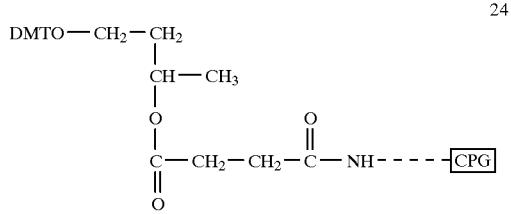

The objective of the approach followed is to prepare a judiciously functionalized solid support with a view to preparing nucleic acid probes in which one or more marking elements interspersed with chemical arms are introduced at 3'(OH) position of the probe using any method of manual or automatic internucleotide linkage synthesis on a solid support.

The method adopted to functionalize the CPG support comprises the following steps (scheme III).

the acid generated 25 is activated in the form of pentachlorophenolic ester 26. The CPG support has at its surface "primary amine" functions which will attach the derivative 26 by forming an amide bond from the activated ester.

Method for Preparing 1-0-(4,4' Dimethoxytrityl) 3-Succinate 1.3-Butanediol 25

2.35 g (6 mmoles) of compound 3 is put into a 50 cc two-necked flask in an argon atmosphere. To this are added 22 cc of anhydrous pyridine, 0.74 g (6.1 mmoles) of 4-dimethylamino pyridine and 0.64 g (6.4 mmoles) of succinic anhydride. The reaction mixture is stirred magnetically for 3 hours at room temperature. Toluene is then added to the reaction mixture and this is followed by azeotropically stripping away the pyridine using toluene (rotary evaporator, p=20 mm Hg). The residue obtained is dissolved in 75 cc of dichloromethane.

The resulting organic phase obtained is washed twice with a solution of citric acid 4×10$^{-2}$M. the organic phase is then dried over MgSO$_4$, filtered and evaporated (rotary evaporator P=20 mm Hg). The residue is purified on a Merck 9385 silica column—eluant: gradient Hexane 15—CH$_2$Cl$_2$ 85 ⇒ CH$_2$Cl$_2$ 100 ⇒ MeOH$_3$—CH$_2$Cl$_2$ 97. The silica has previously been neutralized by suspending it in the starting eluant containing 1% DIEA. After purification 1 g of compound 25 is obtained. Yield: 34%.

Method for Preparing 1-0-(4,4' Dimethoxytrityl) 3-(Pentachlorophenoxy Succinate) 1.3—Butanediol 26

1 g of compound 25 (2 mmoles) is introduced into a 25 cc two-necked flask, an argon atmosphere is adjusted and a solution of 14 cc of anhydrous dimethylformamide containing 0.58 g of pentachlorophenol (2.2 mmoles) and 0.62 g of dicyclohexylcarbodiimide (3 mmoles) is added. The reaction mixture is stirred magnetically for 24 hrs at room temprature. The dicyclohexylurea precipitate is filtered off and the precipitate is then washed with 50 cc of benzene. The benzene is evaporated.

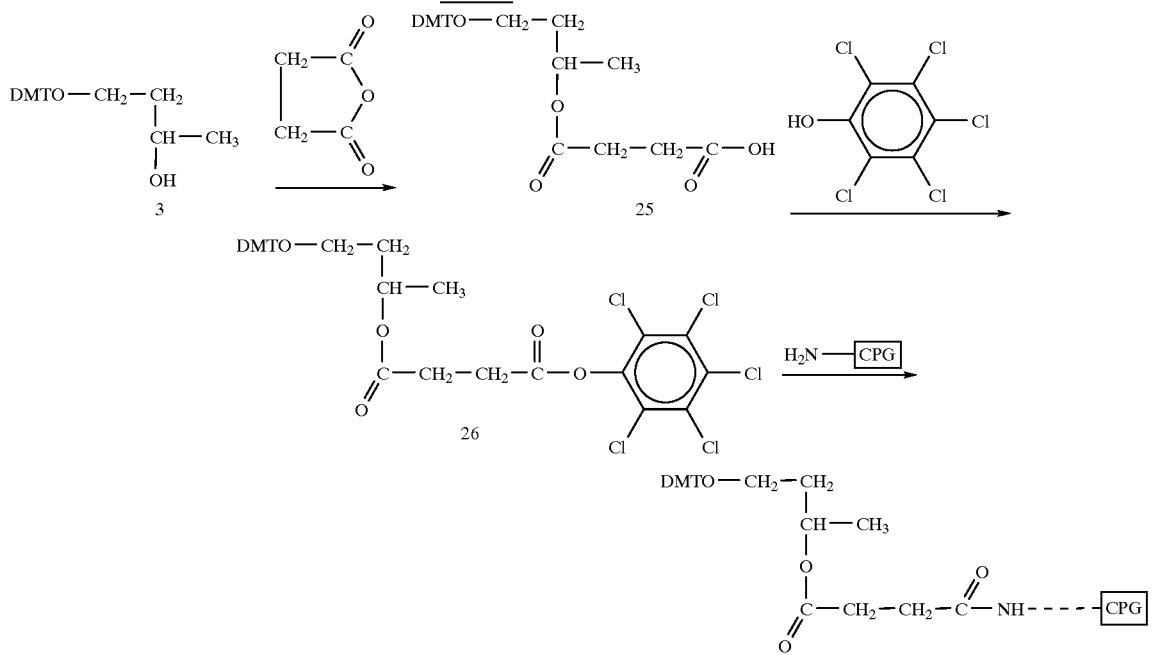

1-0-(4,4' dimethoxytrityl)1,3-butanediol 3 is acylated on the free secondary alcohol using succinic anhydride and then The residue is purified on a Merck 9385 silica column—eluant hexane 15—dichloromethane 85. The silica is previously neutralized by suspending it in the eluant containing 1% DIEA After purification 1.7 g of compound 26 is obtained. Yield=±100%.

Method for Preparing a CPG (Controlled Porous Glass) Solid Support Functionalized by 1-0-(4.4' Dimethoxytrityl) 1.3-Butanediol Groupings 24

The solid support used (Pierce Ref. 24875) has a porosity of 500 Å and it is functionalized at the surface by "primary amine" groups. Into a 10 cc flask are introduced 0.5 g of aminated CPG support, 0.2 cc of freshly distilled triethylamine, 0.385 g of pentachlorophenolic ester 26 (0.26 mmole) and 1.3 cc of anhydrous dimethylformamide. The flask is sealed and the contents are stirred for 24 hrs at 37° C. At this point it is checked on a small aliquot of the solid support to see that it actually has been functionalized by 26. The aliquot is washed several times in ethanol and then in ether, after which it is treated with a 0.1M sulfonic p toluene acid solution in anhydrous acetonitrile. The object of this operation is to deprotect the primary alcohol and make the orange coloration of the dimethoxytrityl cation formed in this anhydrous medium appear. If, therefore, the orange coloration does appear, treatment of the support thus functionalized can then go ahead.

The next stage is to neutralize the primary amine groups of the support that have not reacted. This entails adding to the reaction mixture 70 µl of acetic anhydride and leaving it to work for 10 minutes at 37° C. The solid support is then filtered. Next the support is washed in succession with 20 cc of dimethylformamide, 20 cc of ethyl alcohol, 20 cc of dioxane and 20 cc of ethyl ether. It is then dried under vacuum in a drier (p=20 mm Hg) in the presence of phosphorous pentoxide. This is followed by determining the number of molecules 26 attaching to the support by spectroscopic (visible) quantitative analysis of the number of 4,4'-dimethoxytrityl groups liberated in acid medium per gram of support.

Into a 10 cc graduated flask is introduced 8.1 g of functionalized CPG support, and to this is added 10 ml of 0.1 M sulfonic p toluene acid in anhydrous acetonitrile. The solution turns orange, and the reading is taken at 497 mm. $\epsilon=7.10^4$. An absorbance of 1.72 is measured.

$$C = \frac{A}{\epsilon 1} = \frac{1.72}{7.10^4 \times 1} = 0.245 \; 10^4 \; mole/l$$

The functionalization of the support is therefore 30.3 µmol/g.

EXAMPLE VI

Investigation into the Reactivity of a CPG Support Functionalized by 1-0-(4,4' Dimethoxytrityl) 1,3-Butanediol Units The CPG support 24 functionalized by 1-0-(4,4' dimethoxytrityl) 1,3 butanediol units can be used to introduce at 3'(OH) of an oligonucleotide chemical arms (condensation of derivative 1)
"primary amine" arms (condensation of derivative 4).

The "primary amine" arms are separated from one another and separated from the oligonucleotide chain by chemical arms.

With the object of realising biopolymeric structures of this sort, the reactivity of the CPG support 24 was tested in automatic oligonucleotide synthesis conditions. To this end, the CPG support 24, introduced into a reactor of the automatic oligonucleotide synthesis apparatus, was subjected to a series of condensations respectively of phosphoramidites 1 and 4 and that of the thymidine (T).

If the aminated arm originating from the condensation of a unit 4 is designated N, and the chemical arm originating from the condensation of a unit 1 is designated S, the polymers synthesized are as follows:

| | |
|---|---|
| TTSS | 27 |
| TTNS | 28 |
| SSTT | 29 |
| NSTTSNS | 30 |

The tetramer SSTT was only synthesized to provide a comparison with TTSS in capillary electrophoresis. The phosphoramidites 1 and 4 then successfully attach to the CPG support 24 in conventional condensation conditions (splicing time, solvent, reagents) in an automatic oligonucleotide synthesizer. However, with respect to the condensation of compound 4, the splicing time had to be extended to 10 minutes instead of the 25 seconds employed in the conventional cycle. Moreover, the conventional conditions employed to cleave the oligonucleotides from their solid support (32% $NH_4OH$—4×(500 µl—15 minutes) revealed themselves to be adequate since compounds 27, 28 and 30 were obtained with good yields.

Figure 3A:
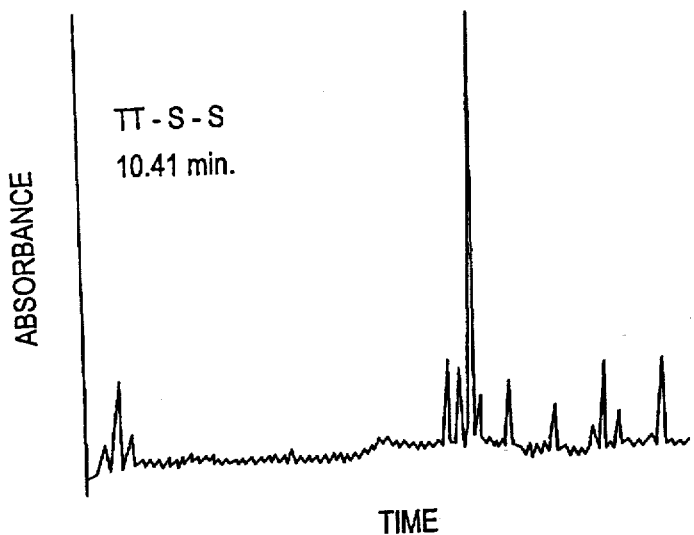
Figure 3B:
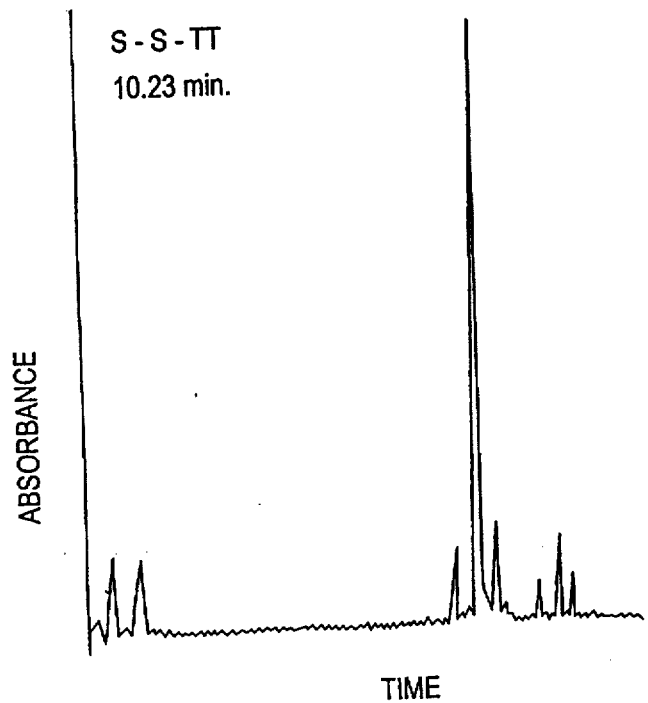
Figure 4A:
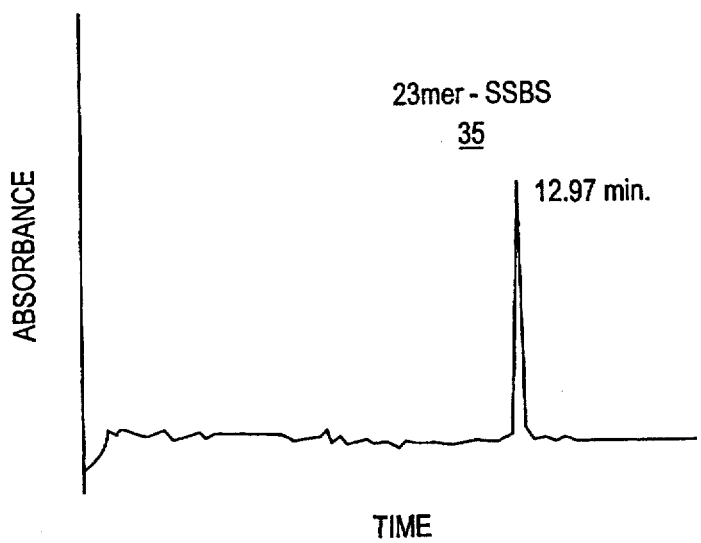
Figure 4B:
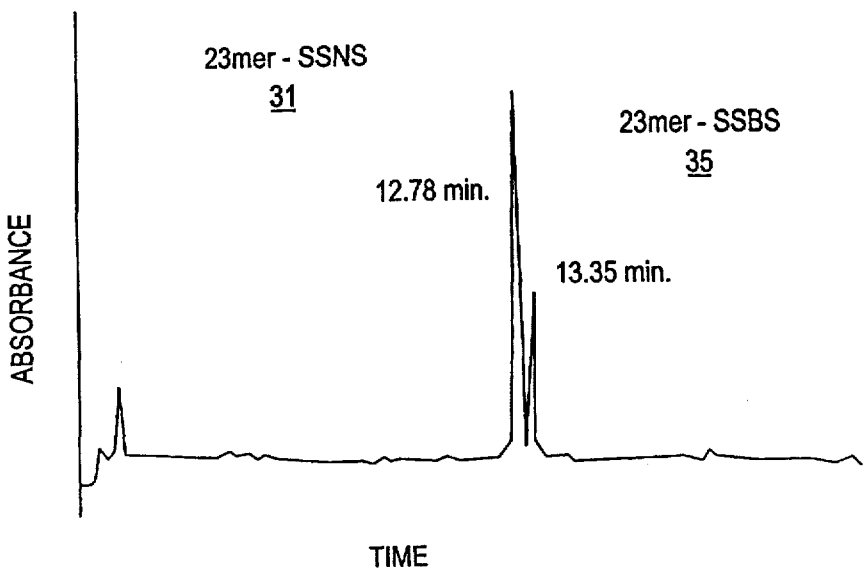
Figure 4C:
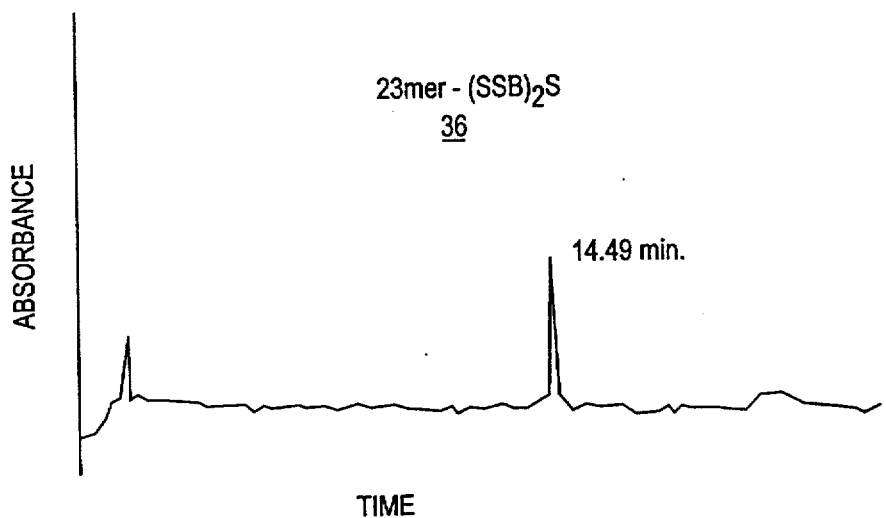
Figure 4D:
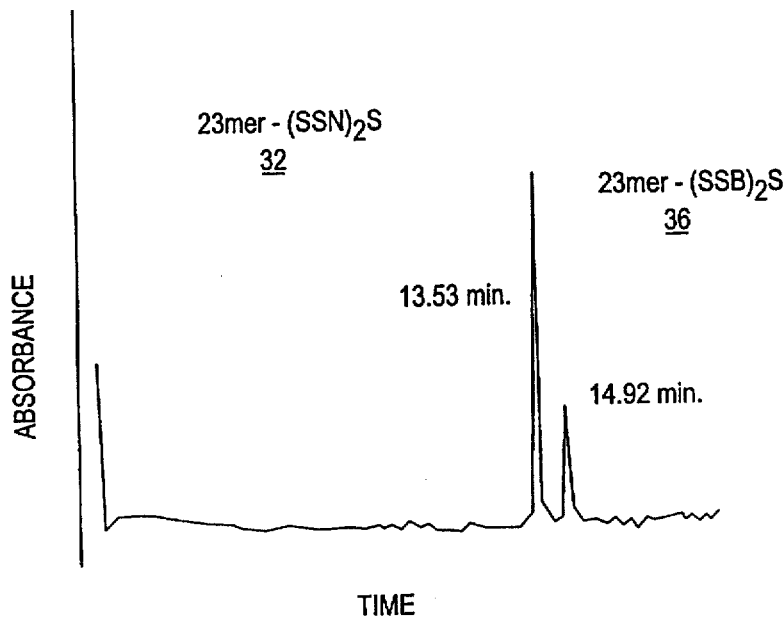
Figure 4E:
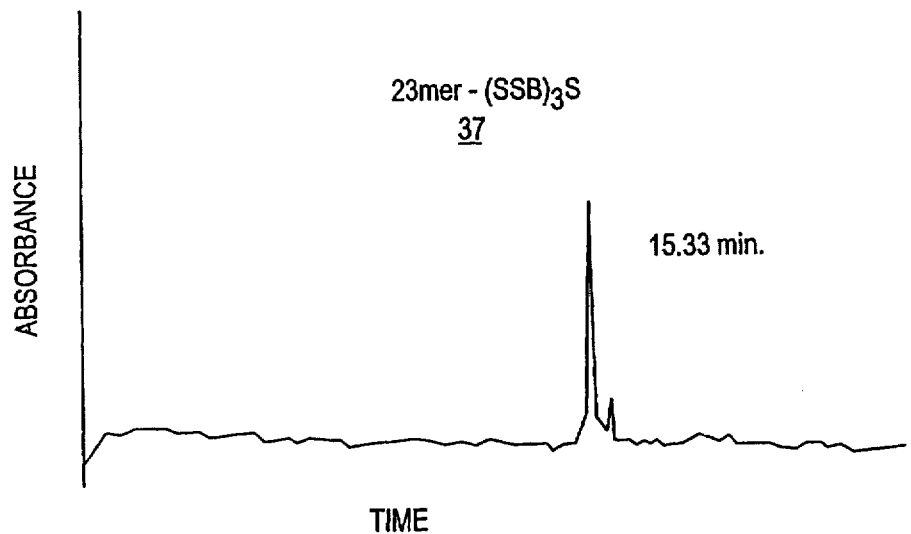
Figure 4F:
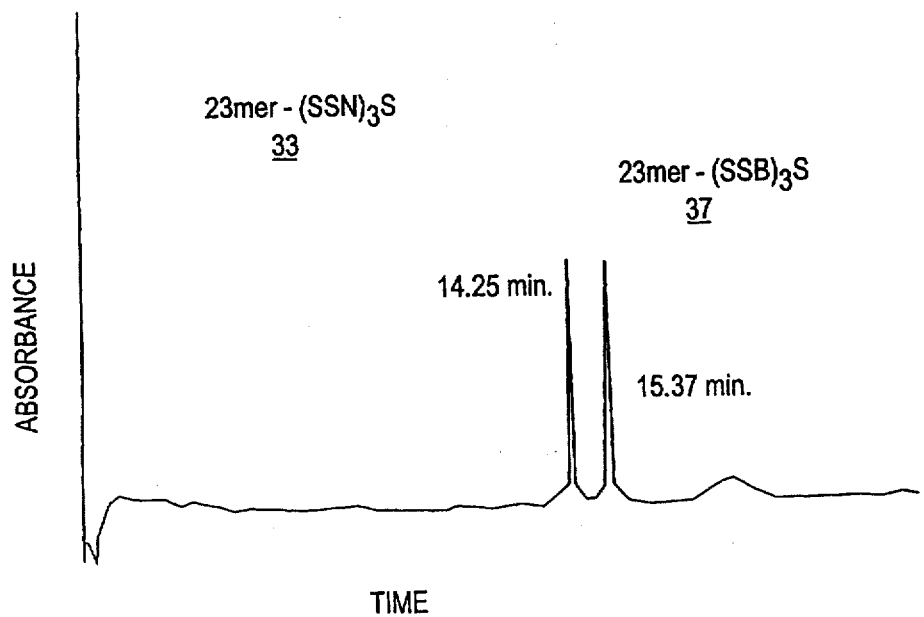
Figure 4G:
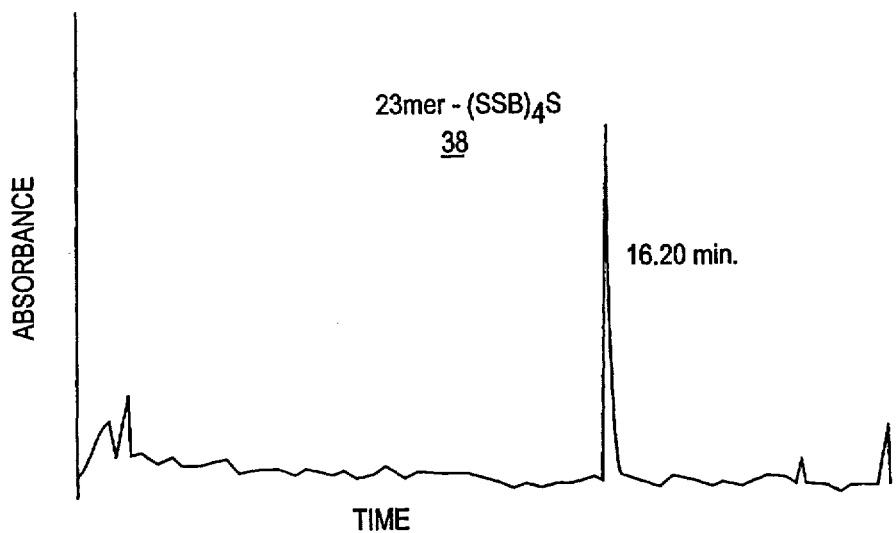
Figure 4H:
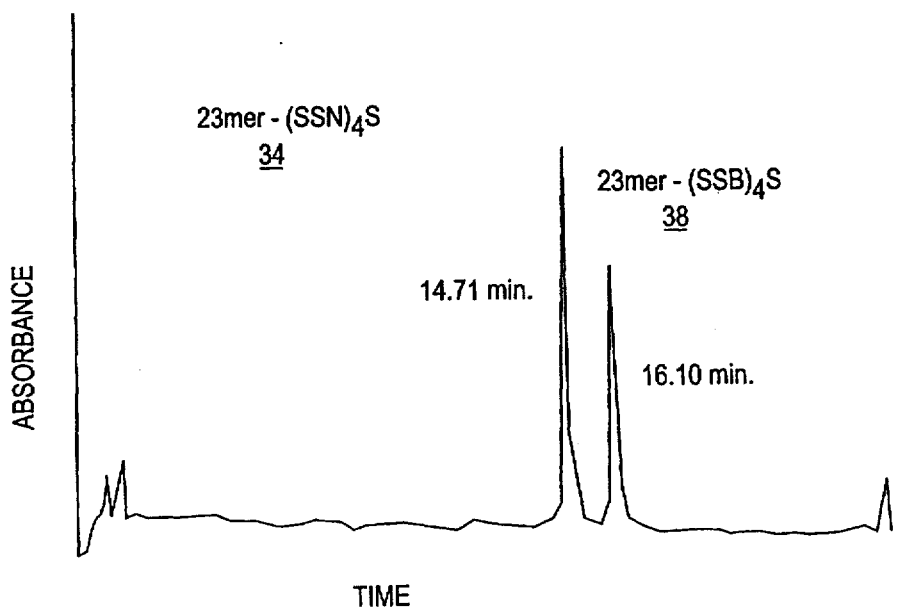

In each of these condensation trials carried out, a relatively pure product is obtained, as shown by the results of capillary electrophoresis analysis (FIG. 3).

Furthermore, in oligonucleotide synthesis it is possible to recover the solution deprotecting the dimethoxytrityl group and to measure the intensity of the orange coloration of the cation in order to assess the yield of each condensation. These measurements were taken in respect of each condensation on the support 24, and they indicate quasi-quantitative yields.

Condensation of Phosphoramidites 1 and 4 on CPG Support 24. Synthesis of Polymers 27, 28 and 30

The three polymers 27, 28 and 30 are simultaneously produced in an ABI 394 automatic oligonucleotide synthesizer. To do this, 6.6 mg (0.2 µmole) of CPG support 24 functionalized at 30.3 µmole/g is introduced into three reactors. Derivative 1 and derivative 4 are solubilized in anhydrous acetonitrile at a 0.1M concentration and introduced into the synthesizer at the locations provided for non-conventional phosphoramidites. The synthesizer is programmed to perform condensation cycles 1, 4 and T in accordance with the sequences of 27, 28 and 30. After automatic synthesis of 27, 28 and 30, the polymers are cleaved from the CPG supports by four successive 15-minute treatments with 500 µl of 32% $NH_4OH$. The ammonia solutions are lyophilized and the residues are analyzed by capillary electrophoresis (ABI 270A), Micro-Gel$_{100}$ column of 50 µm internal diameter, 50 cm length, voltage 15kV, buffer 75mM Tris-phosphate—10% methanol pH 7.6.

EXAMPLE VII

Preparation of Oligodeoxyribonucleotide Mixed Molecules Bearing at 3'(OH) a Linear Tangle of Chemical Arms Interspersed with Aminated Arms Useful in Detecting DNA Sequences by Non-Radioactive Methods The mixed molecules composed of an oligodeoxyribonucleotide part and another part possessing characteristic chemical properties allow easy and rapid detection of target deoxyribonucleic acids by non-radioactive methods. The oligodeoxyribonucleotide part of defined sequence homologous with a target DNA fragment provides the stabilization energy and ensures its hybridization with the DNA molecule that is to be detected. The part that provides the reactivity allowing direct or indirect detection of the hybrid can be introduced at the 5'(OH) and (or) 3'(OH) end of the nucleic acid sequence. In this specific example, the part responsible for the detection will essentially be introduced at 3'(OH) of the nucleic acid sequence. The part responsible for detection will be introduced at 3'(OH) of the oligonucleotide chain by preceding first to a series of condensations of derivatives 1 and 4 on a solid CPG support 24 in the automatic oligonucleotide synthesizer. Once the desired sequence of chemical arms and primary amine has been built up in the automatic synthesizer, the construction of the oligonucleotide chain then follows, building upon the said structure. The condensations of phosphoramidites 1 and 4 in the automatic oligonucleotide synthesizer are carried out using the same reaction cycles as those employed for synthesis of the nucleic acid sequence. However, in respect of derivative 4 the condensation time is extended to 10 minutes instead of the 25 seconds employed in the conventional cycle. After cleavage of the 3' modified oligonucleotide chain from its solid support, and deprotection of the phosphates and bases of the oligonucleotide chain, the part that provides the reactivity responsible for detection will be introduced via a covalent chemical bond. Out of the various molecules possessing the requisite properties for detection, biotin, digoxigenin, fluoroescein, peroxydase and alkaline phosphatase are preferably utilised. These molecules, activated judiciously, are attached to the oligonucleotide chain at the primary amines introduced for that purpose by virtue of their nucleophilic nature.

If the aminated arm originating from the condensation of a unit 4 is designated N, and the chemical arm originating from the condensation of a unit 1 is designated S, the modified oligomers at 3'(OH) which have been synthesized are as follows:

| | |
|---|---|
| TTTTCAAAGAAGATGGCAAAACASSNS | 31 |
| TTTTCAAAGAAGATGGCAAAACASSNSSNS | 32 |
| TTTTCAAAGAAGATGGCAAAACASSNSSNSSNS | 33 |
| TTTTCAAAGAAGATGGCAAAACASSNSSNSSNSNS | 34 |

After cleavage of the modified oligonucleotide chain from-its solid support and deprotection of the bases and phosphates, the four oligonucleotides are analyzed by capillary electrophoresis (FIG. 4).

After deprotection of the primary amnines, probes 31, 32, 33 and 34 are biotinylated. The resulting biotinylated probes 35, 36, 37 and 38 are analyzed by capillary electrophoresis (FIG. 4).

If the aminated arm originating from the condensation of a unit 4 followed by biotinylation is designated B, and the chemical arm originating from the condensation of a unit 1 is designated S, the resulting monobiotinylated or polybiotinylated probes at 3'(OH) are as follows:

| | |
|---|---|
| TTTTCAAAGAAGATGGCAAAACASSBS | 35 |
| TTTTCAAAGAAGATGGCAAAACASSBSSBS | 36 |
| TTTTCAAAGAAGATGGCAAAACASSBSSBSSBS | 37 |
| TTTTCAAAGAAGATGGCAAAACASSBSSBSSBSSBS | 38 |

Method for Preparing Oligodeoxyribonucleotide Mixed Molecules Bearing at 3'(OH) a Linear Tangle of Chemical Arms Interspersed with Aminated Arms. Synthesis of Probes 31, 32, 33 and 34

The four probes 31, 32, 33 and 34 are simultaneously produced in an ABI 394 automatic synthesizer. To do this, 6.6 mg (0.2 μmole) of CPG support 24 functionalized at 30.3 μmole/g is introduced into four reactors. Derivative 1 and derivative 4 are solubilized in anhydrous acetonitrile at a 0.1M concentration and introduced into the synthesizer at the locations provided for non-conventional phosphoramidites. The synthesizer is programmed to begin with cycles for attaching the phosphoramidites 1 and 4 in accordance with the respective sequences 31, 32, 33 and 34, and then to proceed with the nucleotide phosphoramidites to the synthesis of a complementary nucleic acid sequence of a target sequence:

5' TTTTCAAAGAAGATGGCAAAACA 3'

Following automatic synthesis of biopolymers 31, 32, 33 and 34, the oligonucleotide chains accordingly modified are cleaved from the CPG supports by four successive 15-minute treatments with 500 μl of 32% NH$_4$OH.

The ammonia solutions obtained are maintained at 55° C. for 5 hours. The object of this second treatment is to deprotect the bases and phosphates of the oligonucleotide chains. The ammonia solutions are lyophilized, the four residues are subjected to molecular filtration chromatography (G50 Sephadex gel), and then to electrophoresis on 20% polyacrylamide gel.

Method for Biotinylation of Oligodeoxyribonucleotide Mixed Molecules Bearing at 3'(OH) a Linear Tangle of Chemical Arms Interspersed with Aminated Arms. Preparation of Biotinylated Probes 35, 36, 37 and 38 20 DO of aminated probe 31, 32, 33 or 34 is dissolved in 120 μl of 0.01M phosphate buffer pH 7.5 in an Eppendorf tube. A solution of 20 mg of sulfosuccinimidyl 6-biotinamidocaproate in 240 μl of dimethylformamide is added. This is incubated at room temperature for 16 hrs. Next each solution is subjected to molecular filtration chromatography (G50 Sephadex gel), and then to electrophoresis on 20% polyacrylamide gel. The biotinylated probes 35, 36, 37 and 38, as well as the corresponding aminated probes 31, 32, 33 and 34 are analyzed by capillary electrophoresis on a Micro-Gel$_{100}$, internal diameter 50 μm, length 50 cm, voltage 15 kV, buffer 75 mM Tris-phosphate—10% methanol pH 7.6.

EXAMPLE VIII

Preparation of Oligodeoxyribonucleotide Mixed Molecules Bearing at 3'(OH) and at 5'(OH) a Linear Tangle of Chemical Arms Interspersed with Aminated Arms Useful in Detecting DNA Sequences by Non-Radioactive Methods The mixed molecules composed of an oligodeoxyribonucleotide part and another part possessing characteristic chemical properties allow easy and rapid detection of target deoxyribonucleic acids by non-radioactive methods. The oligodeoxyribonucleotide part of defined sequence homologous with a target DNA fragment provides the stabilization energy and ensures its hybridization with the DNA molecule that is to be detected. The part that provides the reactivity allowing direct or indirect detection of the hybrid can be introduced at the 5'(OH) and (or) 3'(OH) end of the nucleic acid sequence. In this specific example, the part responsible for the detection will be introduced to either side of the oligonucleotide sequence simultaneously at 5'(OH) and at 3'(OH).

The part responsible for detection will be introduced at 3'(OH) of the oligonucleotide chain by proceeding first to a series of condensations of derivatives 1 and 4 on a solid CPG support 24 in the automatic oligonucleotide synthesizer. Once the desired sequence of chemical arms and primary amine has been built up in the automatic synthesizer, the construction of the oligonucleotide chain then follows, building upon the structure already in place.

Following the oligonucleotide chain, the synthesizer is programmed to continue cycles of attachment at 5' of units 1 and 4. The condensations of phosphoramidites 1 and 4 in the automatic oligonucleotide synthesizer are carried out using the same reaction cycles as those employed for synthesis of the nucleic acid sequence. However, in respect of compound 4 the condensation time is extended to 10 minutes instead of the 25 seconds employed in the conventional cycle.

After cleavage of the 3'(OH) and 5'(OH) modified oligonucleotide chain from its solid support, and deprotection of the phosphates and bases of the oligonucleotide chain, the part that provides the reactivity responsible for detection will be introduced via a covalent chemical bond. Out of the various molecules possessing the requisite properties for detection, biotin, digonigenin, fluoroescein, peroxydase and alkaline phosphatase are preferably utilised.

These molecules, activated judiciously, attach to the oligonucleotide chain at the primary amines introduced for that purpose by virtue of their nucleophilic nature.

If the aminated arm originating from the condensation of a unit 4 is designated N, and the chemical arm originating from the condensation of a unit 1 is designated S, the modified oligomers at 3'(OH) and 5'(OH) which have been synthesized are as follows:

| | |
|---|---|
| NSSTTTTCAAAGAAGATGGCAAAACASSNS | 39 |
| NSSNSSTTTTCAAAGAAGATGGCAAAACASSNSSNS | 40 |
| NSSNSSNSSTTTTCAAAGAAGATGGCAAAACASSNSSNSSNS | 41 |
| NSSNSSNSSNSSTTTTCAAAGAAGATGGCAAAACASSNSSNSSNSSNS | 42 |

After cleavage of the modified oligonucleotide chain from its solid support, and deprotection of the bases and phosphates, the four oligonucleotides are analyzed by capillary electrophoresis (FIG. 5).

Probes 39, 40, 41 and 42 are then biotinylated; the resulting biotinylated probes 43, 44, 45 and 46 are analyzed by capillary electrophoresis (FIG. 5).

If the aminated arm originating from the condensation of a unit 4 followed by biotinylation is designated B, and the chemical arm originating from the condensation of a unit 1 is designated S, the resulting biotinylated probes at 3'(OH) and at 5'(OH) are as follows:

| | |
|---|---|
| BSSTTTTCAAAGAAGATGGCAAAACASSBS | 43 |
| BSSBSSTTTTCAAAGAAGATGGCAAAACASSBSSBS | 44 |
| BSSBSSBSSTTTTCAAAGAAGATGGCAAAACASSBSSBSSBS | 45 |
| BSSBSSBSSBSSTTTTCAAAGAAGATGGCAAAACASSBSSBSSBSSBS | 46 |

Method for Preparing Oligodeoxyribonucleotide Mixed Molecules Bearing at 3'(OH) and at 5'(OH) a Linear Tangle of Chemical Arms Interspersed with Aminated Arms. Synthesis of Probes 39, 40, 41 and 42

The four probes 39, 40, 41 and 42 are simultaneously produced in an ABI 394 automatic DNA synthesizer. To do this, 6.6 mg (0.2 µmole) of CPG support 24 functionalized at 30.3 µmole/g is introduced into four reactors. Derivative 1 and derivative 4 are solubilized in anhydrous acetonitrile at a 0.1M concentration and introduced into the synthesizer at the locations provided for non-conventional phosphoramidites.

The synthesizer is programmed to begin with cycles for attaching the phosphoramidites 1 and 4 in accordance with the respective sequences 39, 40, 41 and 42, and then to proceed with the nucleotide phosphoramidites to the synthesis of a complementary nucleic acid sequence of a target sequence:

5' TTTTCAAAGAAGATGGCAAAACA 3' and finally to continue condensation cycles in respect of units 1 and 4 at 5' of the chain of nucleic acids.

Following automatic synthesis of biopolymers 39, 40, 41 and 42, the oligonucleotide chains accordingly modified are cleaved from the CPG supports by four successive 15-minute treatments with 500 µl of 32% $NH_4OH$.

The ammonia solutions obtained are maintained at 55° C. for 5 hours. The object of this second treatment is to deprotect the bases and phosphates of the oligonucleotide chains. The ammonia solutions are lyophilized, the four residues are subjected to molecular filtration chromatography (G50 Sephadex gel), and then to electrophoresis on 20% polyacrylamide gel.

Method for Biotinylation of Oligodeoxyribonucleotide Mixed Molecules Bearing at 3'(OH) and at 5'(OH) a Linear Tangle of Chemical Arms Interspersed with Aminated Arms. Preparation of Biotinylated Probes 43, 44, 45 and 46

20 DO of probe 39, 40, 41 or 42 is dissolved in 120 µl of 0.1M phosphate buffer pH 7.5 in an Eppendorf tube. A solution of 30 mg of sulfosuccinimidyl 6-biotinamidocaproate in 360 µl of dimethylformamide is added. This is incubated at room temperature for 16 hrs. Next each solution is subjected to molecular filtration chromatography (G50 Sephadex gel), and then to electrophoresis on 20% polyacrylamide gel. The biotinylated probes 43, 44, 45 and 46, as well as the corresponding aminated probes 39, 40, 41 and 42 are analyzed by capillary electrophoresis on a Micro-Gel$_{100}$ column, internal diameter 50 µm length 50 cm, voltage 15 kV, buffer 75 mM Tris-phosphate—10% methanol pH 7.6.

EXAMPLE IX

Use of the Biotinylated Probes Described in Examples IV, VII and VIII in Hybridization on a Solid Support—Limits of Detection In order to show the advantages of the present invention, the probes polybiotinylated at 5'(OH) 20, 21, 22 and 23, the probes polybiotinylated at 3'(OH) 35, 36, 37 and 38, as well as the probes polybiotinylated at 3'(OH) and at 5'(OH) 43, 44, 45 and 46 were tested in hybridization in order to investigate their potential for diagnostic use.

Generally speaking, hybridization takes place between an oligonucleotide (30 mer) attaching to a plastics solid support by its 5'(OH) extremity and complementary to the probes to be tested (23 mer) by its 3'(OH) extremity. Each solid support (tube) is coated with in the order of 10 ng of oligonucleotide (30 mer) complementary to the probes to be tested, representing approximately $10^{12}$ copies. Each biotinylated oligonucleotide mentioned above is subjected to 8 different hybridizations, starting off with 1 pg labelled oligonucleotide (~$10^8$ copies) and going as far as 300 atg ($3 \times 10^4$ copies) in 1/3 dilutions, from one bowl to the next. After hybridization, chemiluminescence (CSPD—Tropix) is used for disclosure; the reading is taken on a luminometer.

The results summarized in Scheme IV relate to the hybridization of the polybiotinylated probes at 5'(OH) 20, 21, 22 and 23 with the complementary 30 mer attaching to the plastics tube.

Scheme IV

| OLIGO | Number of biotins | | Limit of detection | |
|---|---|---|---|---|
| | | | fg | number of copies |
| 20 | 1 | 5'(OH) | 30 | $3 \times 10^6$ |
| 21 | 2 | 5'(OH) | 30 | $3 \times 10^6$ |
| 22 | 3 | 5'(OH) | 30 | $3 \times 10^6$ |
| 23 | 4 | 5'(OH) | 3 | $3 \times 10^5$ |

The results of hybridization in respect of the probes polybiotinylated at 3'(OH) 35, 36, 37 and 38 are summarized in Scheme V.

Scheme V

| OLIGO | Number of biotins | | Limit of detection | |
|---|---|---|---|---|
| | | | fg | number of copies |
| 35 | 1 | 3'(OH) | 30 | $3 \times 10^6$ |
| 36 | 2 | 3'(OH) | 10 | $10^6$ |
| 37 | 3 | 3'(OH) | 3 | $3 \times 10^5$ |
| 38 | 4 | 3'(OH) | 3 | $3 \times 10^5$ |

The results in respect of the probes polybiotinylated at 5'(OH) and at 3'(OH) 43, 44, 45 and 46 are summarized in Scheme VI.

Scheme VI

| OLIGO | Number of biotins | | Limit of detection | |
|---|---|---|---|---|
| | | | fg | number of copies |
| 43 | 2 | 3' + 5'(OH) | 30 | $3 \times 10^6$ |
| 44 | 4 | 3' + 5'(OH) | 10 | $10^6$ |
| 45 | 6 | 3' + 5'(OH) | 3 | $3 \times 10^5$ |
| 46 | 8 | 3' + 5'(OH) | 1 | $10^5$ |

Method for Hybridization of a Monobiotinylated or Polybiotinylated Probe (23 mer) with a Complementary Oligomer (30 mer) Attaching to a Plastics Tube The tubes, covered with complementary oligonucleotide (30 mer) are first saturated for one hour at 37° C. with 200 µl of a 5% solution of skimmed milk lyophilized in TBS 1× containing a trace of azide. The tubes are then prehybridized for 2 hours at 50° C. with the hybridization buffer (100 µl): 5× Denhardt's, 6×SSC, 0.1% SDS, 100 µg/ml of salmon sperm DNA.

For each oligonucleotide to be tested, 8 trials are undertaken with the following quantities (in 100 µl of hybridization buffer): 1 pg ($10^8$ copies), 300 fg, 100 fg ($10^7$ copies), 30 fg, 10 fg, ($10^6$ copies), 3 fg, 1 fg ($10^5$ copies), 0.3 fg. A series of eight tubes are also produced with an unbiotinylated, non-complementary oligomer, and eight tubes without oligonucleotide.

All the tubes are hybridized for 2 hrs at 50° C., then each tube is washed three times for ten minutes at 50° C. with an SSC 6× solution. They are then washed once for five minutes with buffer I.

Buffer 1:0.1 M Tris, 2 mM $MgCl_2$, 0.05 % triton, 1 M NaCl.

A solution of alkaline streptavidin-phosphatase is now prepared (supplied with the Tropix kit): 1 µl of the solution from the kit in 5,500 µl of buffer I. 100 µl of this solution is put into each tube, left to incubate for thirty minutes at room temperature, and then each tube is washed six times with buffer I. The solution of chemiluminescent agent CSPD is prepared: (3-(4-methoxyspiro[1,2-dioxetane-3,2'-tricyclo [3.3.1.1.]chlorodecane]-4-yl) phenyl phosphate.

The solution is prepared as follows: 80 µl of CSPD (Tropix), 500 µl of "emerald" (Tropix) and 4,420 µl of disclosing buffer.

Disclosing buffer: 0.1 M diethanolamine, 1 MM $MgCl_2$, 0.02 % sodium azide. 100 µl of this solution is placed in each tube, left to incubate for 45 min and then read on the luminometer.

EXAMPLE X

Preparation of 1,6-0-(4,4' dimethoxtrityl) 2-0-(N,N' diisopropylamino 2-cyanoethoxyphosphino) 1.2,6-hexane triol The derivative 1,6-0-(4,4' dimethoxytrityl) 2-0-(N,N' diisopropylamino 2-cyanoethoxy-phosphino) 1,2,6-hexane triol 47 satisfies the formula:

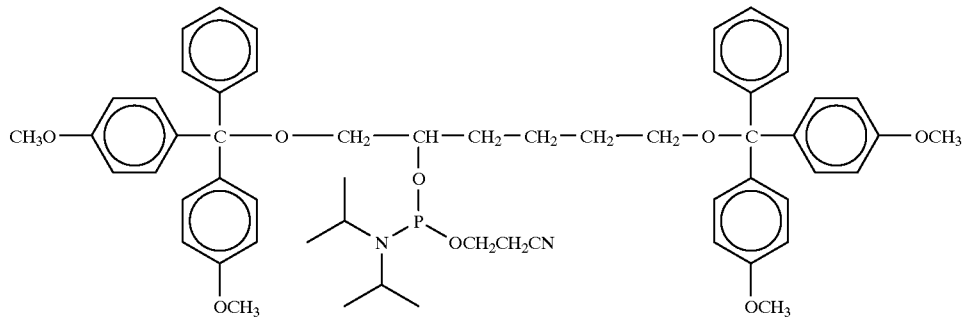

47

The objective of the procedure adopted is to prepare a non-nucleotide synthon which nevertheless bears chemical groups enabling it to be introduced at 5'(OH) of an oligonucleotide chain or in a non-nucleotide polymer the monomers of which are united by a phosphodiester bond in standard automatic RNA or DNA synthesis conditions.

This synthon has the advantage of providing the user with a tool enabling branching chains to be introduced at 5'(OH) position in a nucleic acid sequence without leaving the automatic or manual synthesis routine.

This is because it possesses two primary alcohol functions protected by a dimethoxytrityl group and, therefore, with each condensation cycle it doubles the number of sites for the following condensation.

The attraction of multiplying the number of condensation sites lies in the option of being able to introduce alkyl chains bearing a primary amine at the said sites at the end of synthesis. This introduction is possible through condensation, at the end of synthesis, of derivative 48 at the n primary alcohol sites created.

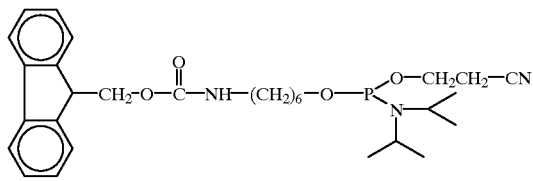

48

Derivative 48 is known in the literature and is therefore neither claimed nor described here.

As far as compound 47 is concerned, the 4,4'-dimethoxytrityl and 2-cyanoethoxydiisopropylaminophosphoramidite groups are suited to synthesis with the phosphoramidites, notably on a solid support.

The reaction path for obtaining compound 47 presented in scheme VII comprises the following steps:

1) selective protection of the two primary alcohols of 1,2,6-hexane triol 49 using dimethoxytrityl chloride (DMT) labile in an acid pH.

2) phosphorylation of secondary alcohol 50. The example of the phosphoramidite shown in Scheme VII is not limititative; synthesis of a triester or diester phosphate or of a phosphonate would equally be feasible.

Method for Preparing 1,6-0-(4,4-Dimethoxntrityly 1,2,6,- Hexane Triol 50

1.34 g of 1,2,6-hexane triol 49 ($10^2$ mole) is put into a 50 cc two-necked flask. This is placed in an argon atmosphere and then 20 cc of anhydrous pyridine is added. Next 8.45 g ($2.5 \times 10^{-2}$ moles) of dimethoxytrityl chloride is added to the solution, which is now stirred for 2 hours at room temperature. The reaction mixture (25 cc of 5% $NaHCO_3$) is hydrolyzed and extraction in dichloromethane (2×50 cc) is carried out. The resulting organic phase is washed three times in water and then once with a saturated aqueous solution of sodium chloride, it is dried over $MgSO_4$ and then filtered and evaporated at reduced pressure (rotary evaporator p=20 mm Hg). Next the residual pyridine is removed by stripping it away azeotropically at reduced pressure with toluene. The residual toluene is then removed by azeotropically stripping it away at reduced pressure with dichloromethane. The residue obtained is purified on a Merck 9385 silica column—eluant ether $0 \rightarrow 40$—hexane $100 \rightarrow 60$. The silica is previously neutralized by suspending it in the starting eluant containing 1% DIEA. After purification, 4.5 g ($6.1 \times 10^{-3}$ moles) is recovered; yield 61%. Thin layer chromatography—Merck 5735 plate ($60F_{254}$ silica gel), eluant ether 4—hexane 6; Final ratio: 0.3.

Method for Preparing 1,6-0-(4,4' Dimethoxytrityl 2-0—(N, N'-Diisopropylamino-2-Cyanoethoxvphosphino) 2.2.6 Hexane Triol 47

1.1 g of compound 50 ($1.5 \times 10^{-3}$ moles) of compound 50 is introduced into a 25 cc two-necked flask. An argon atmosphere is adjusted and then 6 cc of anhydrous tetrahydrofurane and 0.84 cc of diisopropylethylamine are added. Next 0.45 cc ($2 \times 10^{-3}$ moles) of 2-cyanoethoxy diisopropylamino chlorophosphine is added to the reaction mixture, one drop at a time using a syringe. After reacting for ten minutes a substantial precipitate appears inside the reaction mixture (diisopropylethylamine hydrochloride). The reaction mixture is hydrolyzed (15 cc 5% $NaHCO_3$), and extracted with dichloromethane (2×30 cc). The resulting

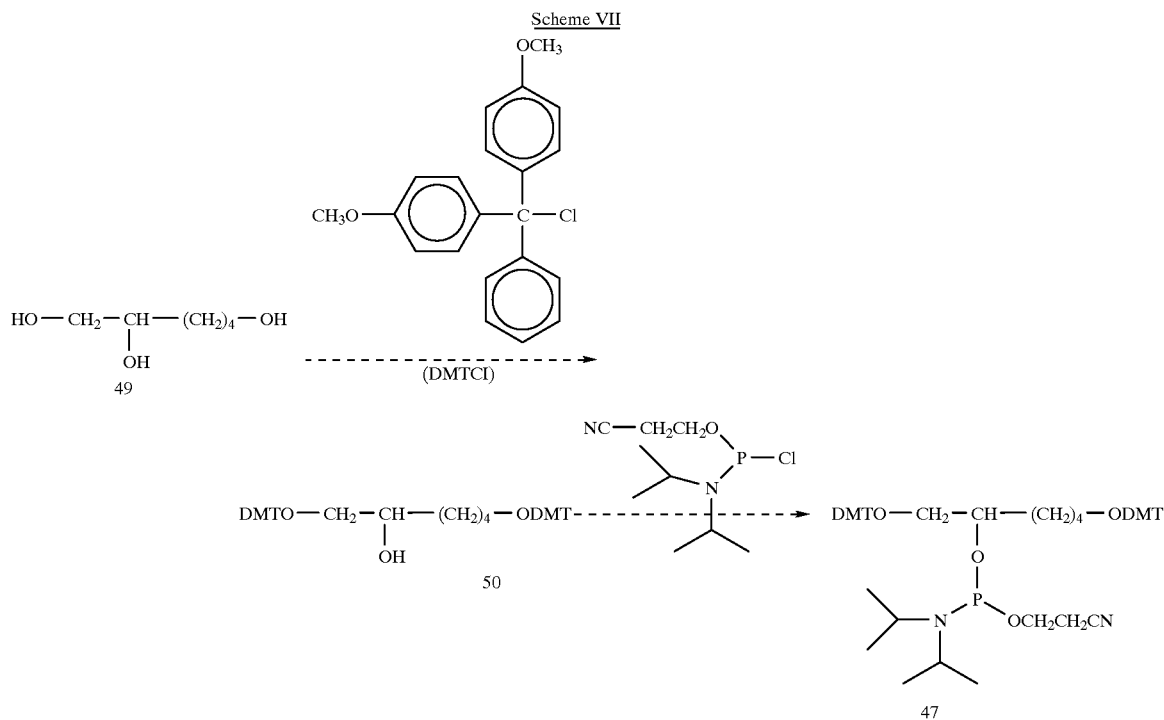

Scheme VII organic phase is washed in water (3×20 cc), then with an aqueous solution saturated in sodium chloride (1×20 cc), it is dried over MgSO₄, filtered and evaporated under reduced pressure (rotary evaporator p=20 mm Hg). The residue is purified on a Merck 9385 silica column—eluant ethyl acetate 3—hexane 7. The silica is previously neutralized by suspending it in eluant containing 1% DIEA. After purification 1.2 g of 47 is obtained. Yield 84%.

Thin layer chromatography using Merck 5735 plate (60F$_{254}$ silica gel)—eluant ethyl acetate 3—hexane 7. Final ratio: 0.6.

EXAMPLE XI

Investigation into the Reactivity of Compound 47

The non-nucleotide phosphoramidite 47 can be used to introduce a branched chain at the 5'(OH) site of a nucleic acid sequence: the attraction of 47 is in multiplying the number of condensation sites by two with each condensation. By the end of synthesis it is therefore possible to introduce alkyl chains bearing a primary amine onto the condensation sites thus created. The introduction of the primary amines is realised by final condensation of derivative 48 on the n primary alcohol sites created.

At an earlier stage, derivative 47 was condensed in the automatic oligonucleotide synthesis apparatus at 5'(OH) of a T-T thymidine-thymidine dimer fixed on a solid support (CPG support: controlled porous glass) conventionally used in automatic synthesis.

If

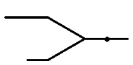

represents the group originating from condensation of a unit 47 in which • represents a phosphate, the TT dimers modified at 5'(OH) which have been synthesized can be represented in the following manner:

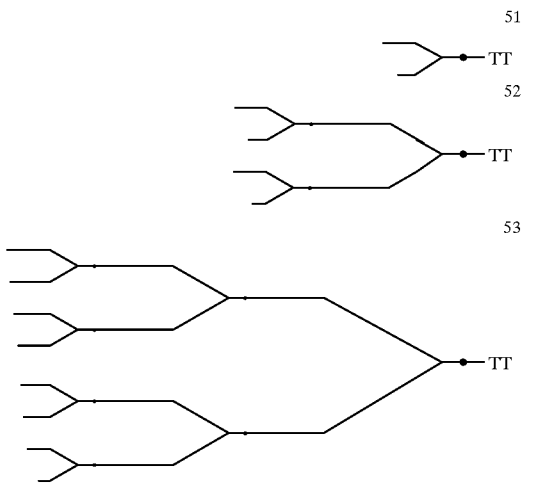

Figure 6A:
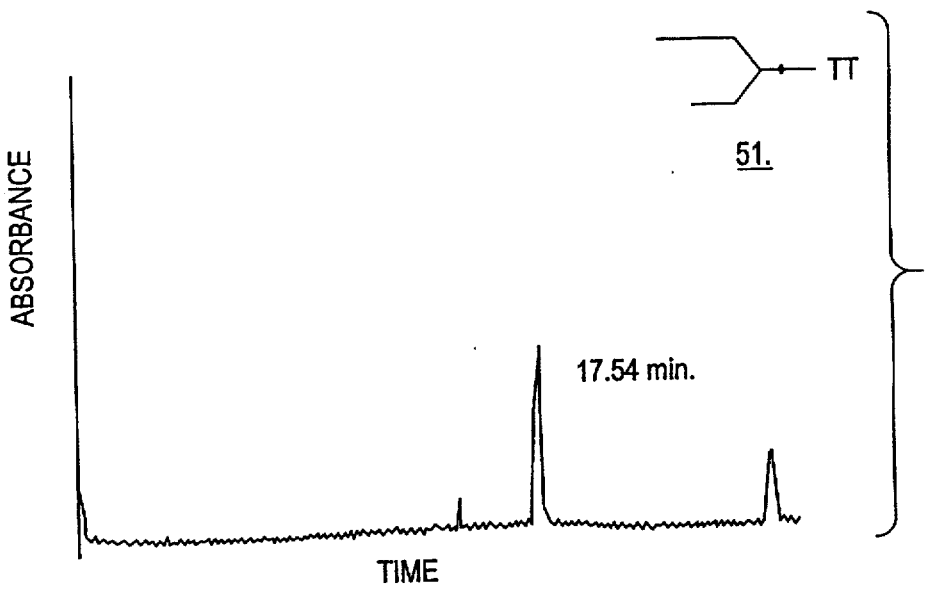
Figure 6B:
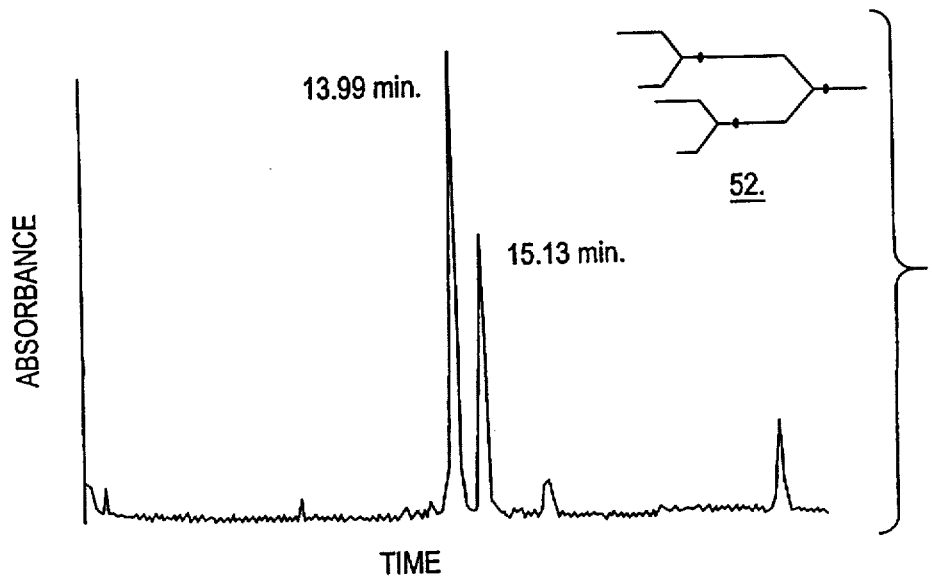
Figure 6C:
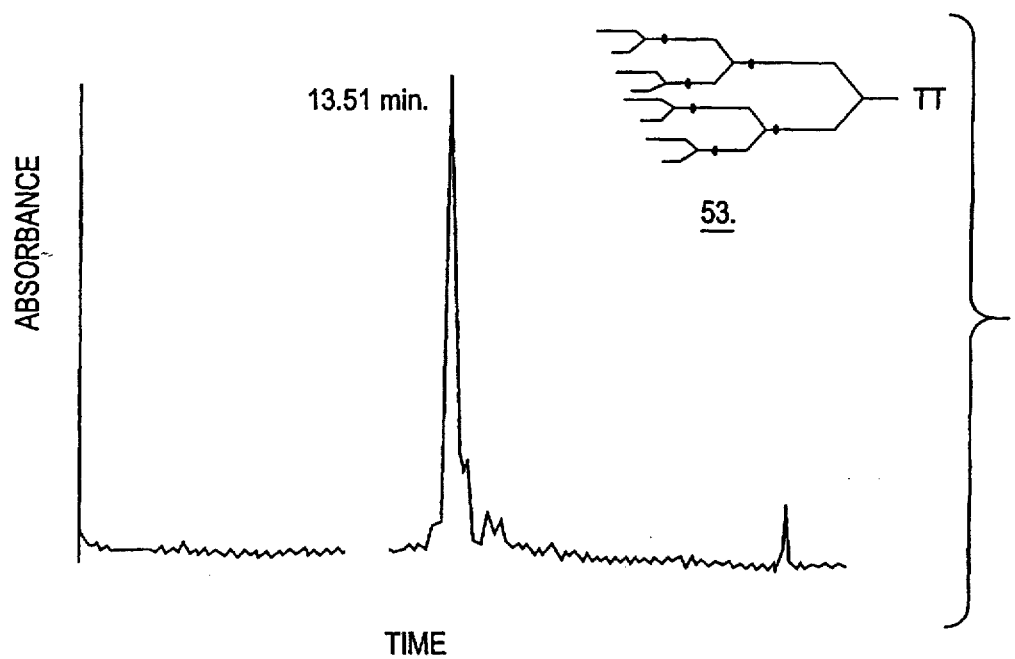

As shown by the capillary electrophoresis analyses (FIG. 6), derivative 47 attaches successfully at 5'(OH) position on an elongated oligonucleotide (cf. 51), it attaches successfully on two condensation sites created after a first condensation of 47 on TT (cf. 52) and it attaches well on the four condensation sites created after two successive condensations of 47 on TT (cf. 53).

Given that the number of condensation sites is multiplied by two at each cycle, the solution of 47 which was used to simultaneously prepare derivatives 51, 52 and 53 in the automatic oligonucleotide synthesizer is 0.4 M (0.1 M under conventional conditions); moreover, the splicing time is extended to 10 minutes (25 seconds under conventional conditions).

These results also show that the reactions of condensation, oxidation, capping and cleavage from the solid support following synthesis are effective and do not degrade polymers 51, 52 and 53.

Furthermore, in oligonucleotide synthesis it is possible to recover the solution deprotecting the dimethoxytrityl group and to measure the intensity of the orange coloration of the cation for the purpose of assessing the yield from each condensation. These measurements were carried out for the synthesis of 53 at each cycle; they indicate good yields, as shown by the results below (Scheme VIII).

| Scheme VIII | | |
|---|---|---|
| 1st condensation (T) | 1 DMT A$_{497}$: 0.93 | Yield: 100% (imposed) |
| 2nd condensation | 2 DMT A$_{497}$: 1.78 | Yield: 95% |
| 3rd condensation | 4 DMT A$_{497}$: 3.4 | Yield: 95% |
| 4th condensation | 8 DMT A$_{497}$: 5.3 | Yield: 77% |

On a second occasion, we carried out x number of condensations of 47 (x=1 ⇒ 3) on a TT thymidine-thymidine dimer attaching to a solid support (CPG support) conventional in automatic synthesis, then we finished by condensation of 48 on the n condensation sites created for the purpose of introducing n primary amine sites for subsequent attachment of n marking elements.

If

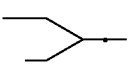

represents the group originating from condensation of a unit 47 where:

• represents a phosphate, and

represents the group resulting from condensation of a unit 48 where:

• represents a phosphate, the modified TT dimers which have been synthesized are as follows:

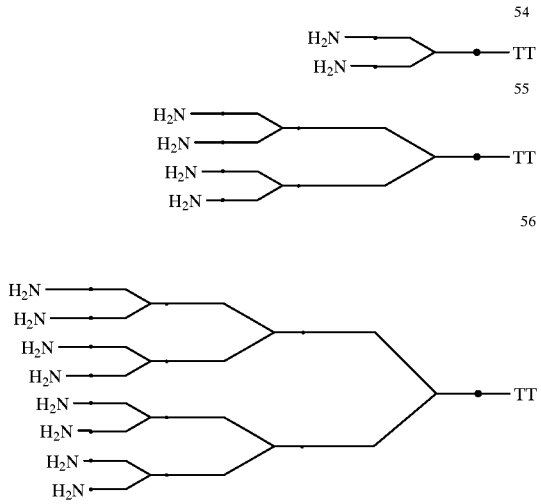

Figure 7A:
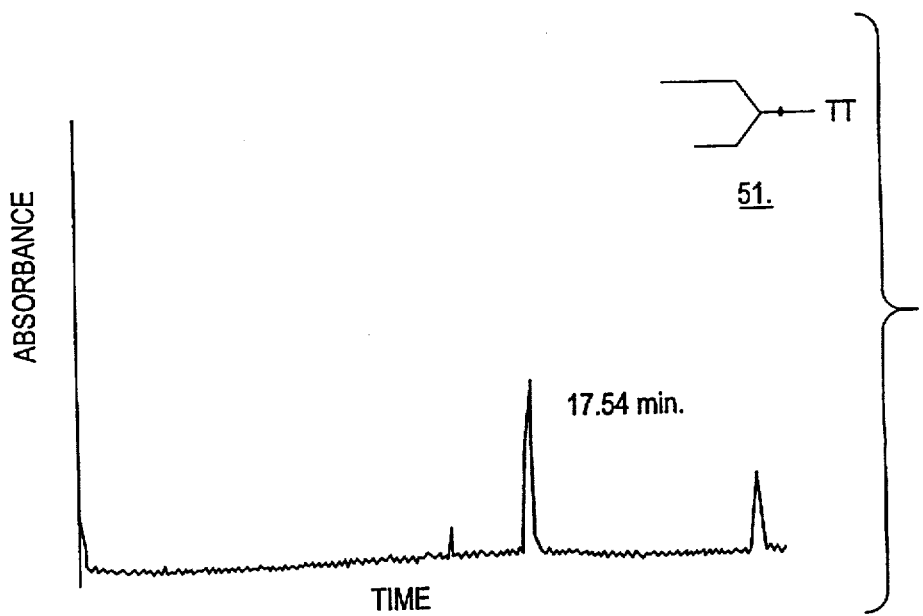
Figure 7B:
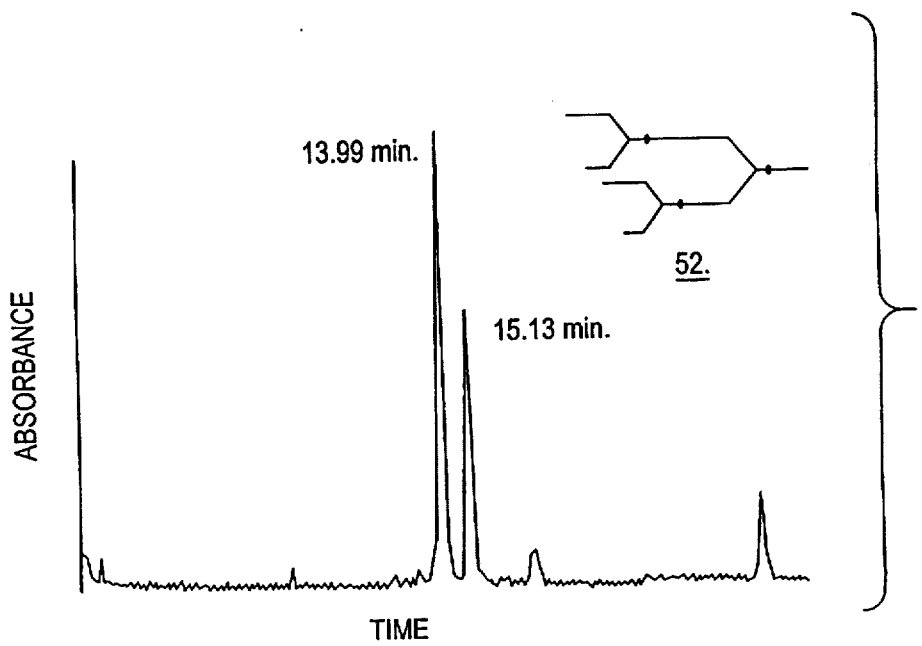
Figure 7C:
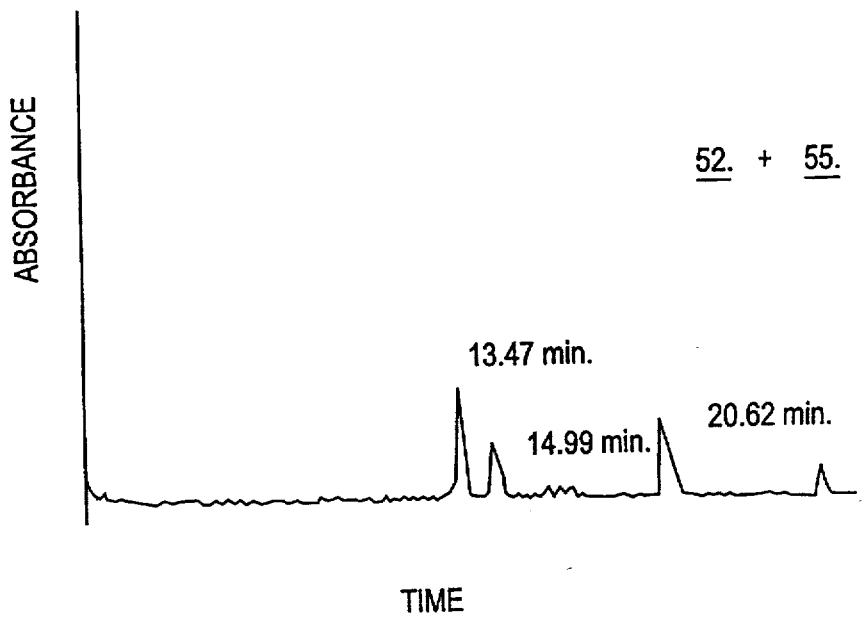
Figure 8A:
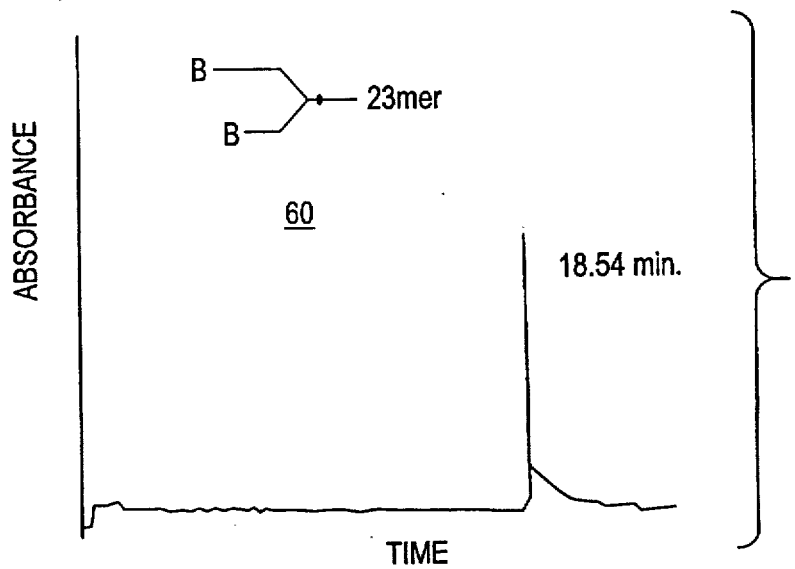
Figure 8B:
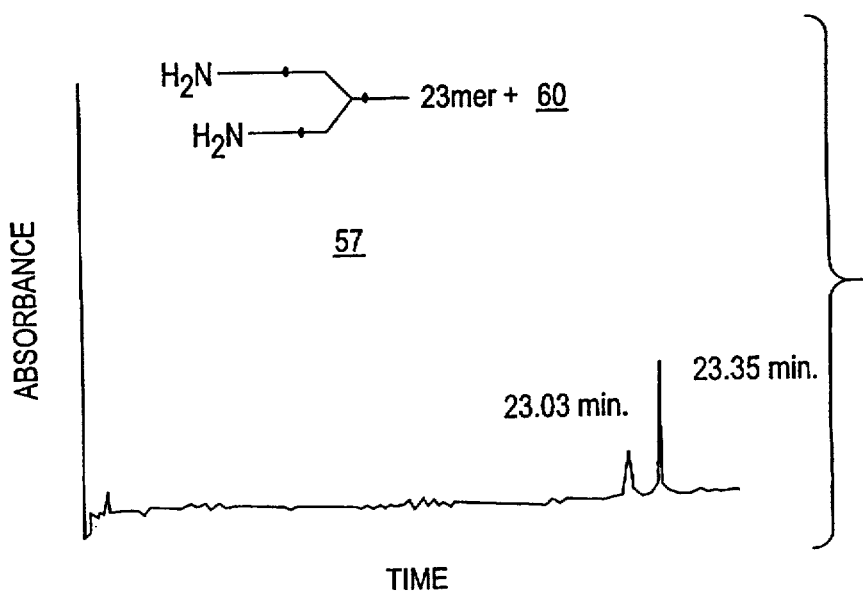
Figure 8C:
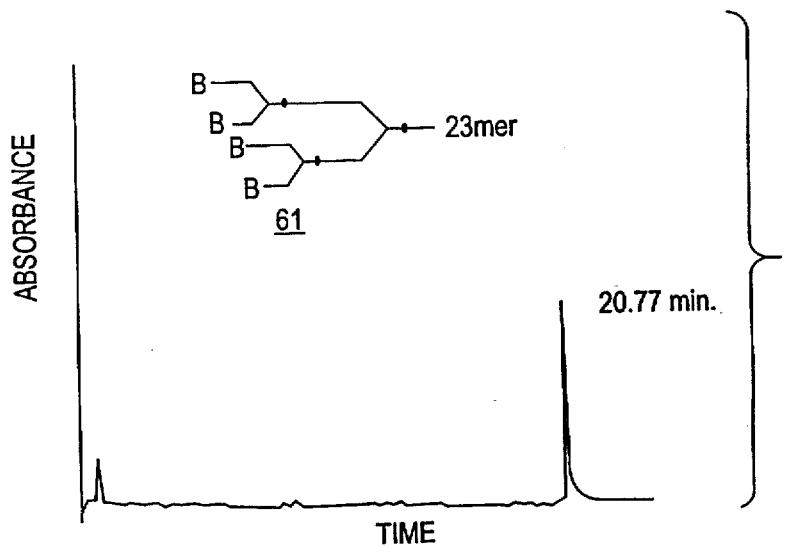
Figure 8D:
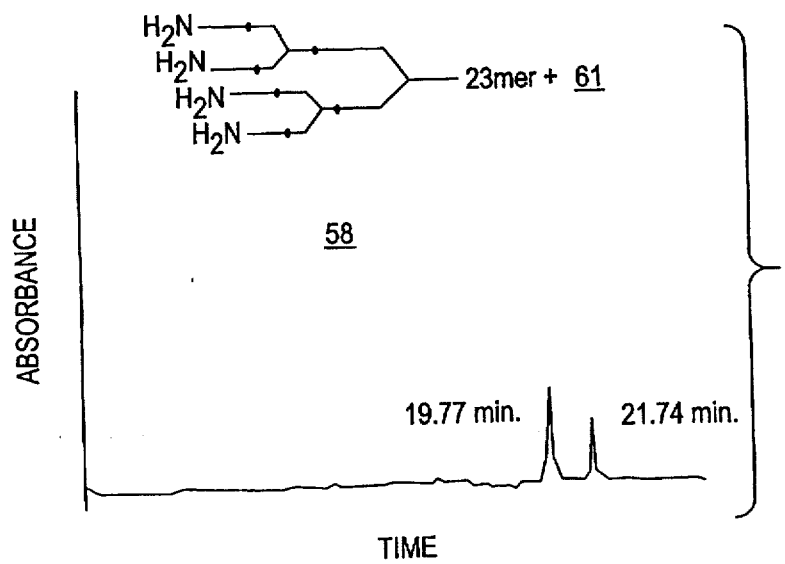
Figure 8E:
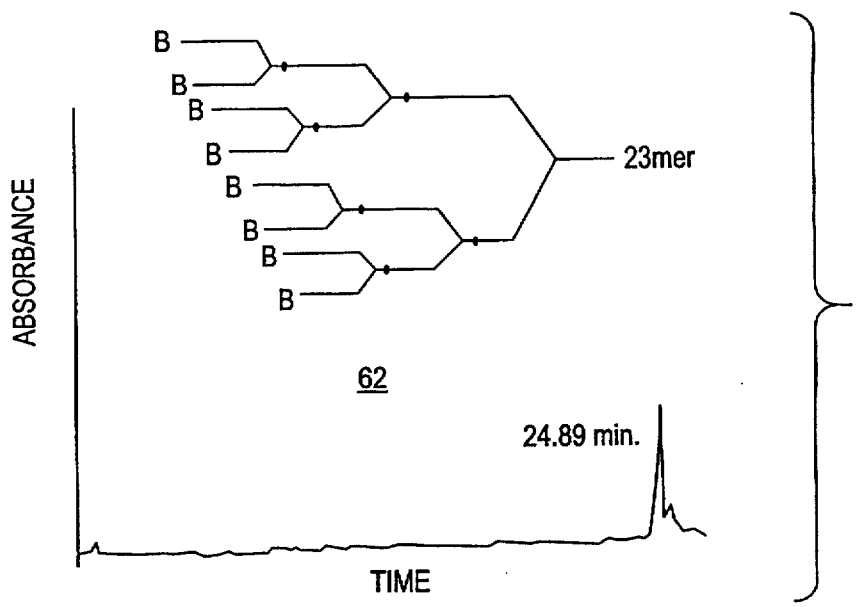
Figure 8F:
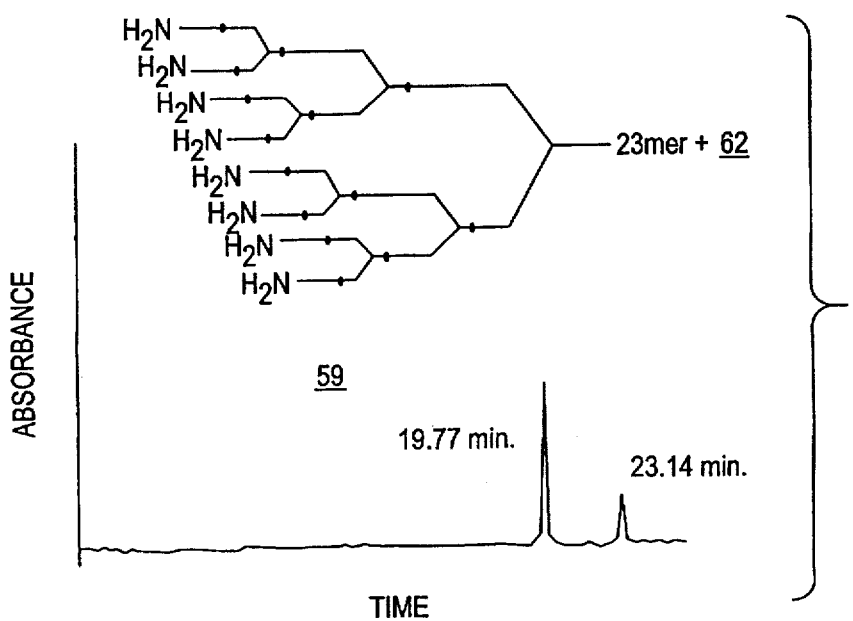

As the capillary electrophoresis analyses show in respect of compound 55 by way of example (FIG. 7), derivative 48 efficiently attaches to the four condensation sites created in polymer 52 since only a trace of 52 is found on the electropherogram for 55.

Given that the number of condensation sites is multiplied by two at each cycle, the solution of 47 which was used to simultaneously prepare compounds 54, 55 and 56 in the automatic oligonucleotide synthesizer is 0.4 M and the solution of 48 is 0.8 N (0.1 M under conventional conditions). Moreover, the splicing time is extended to 10 minutes for the condensations of 47 and 48 (25 seconds under conventional conditions).

Solid Phase Splicing of Derivatives 47 and 48 with a Thymidine-Thymidine Dimer Attaching to a Solid CPG Support Phosphoramidite 47 is solubilized in anhydrous acetonitrile at a concertration of 0.4 M and phosphoramidite 48 is solubilized in the same solvent at a concentration of 0.8 M. They are introduced into the automatic oligonucleotide synthesizer at the locations provided for non-conventional phosphoramidites.

For condensations of 47 and 48, all the condensation conditions are the conditions applying to an oligonucleotide elongation cycle, except for the concentration of phosphoramidite and the splicing time. Cleavage from the solid support is performed under standard conditions (32% $NH_4OH$) and the end product is obtained in a yield comparable to those currently realised in oligonucleotide synthesis.

Polymers 51, 52, 53, 54, 55 and 56 were analysed by capillary electrophoresis with an ABI 270A, Micro-Gel$_{100}$ capillary column, internal diameter 50 μm, length 50 cm, voltage 15 kV, buffer 75 mM Tris-phosphate 10% methanol pH 7.6.

EXAMPLE XII

Preparation of Oligodeoxyribonucleotide Mixed Molecules Bearing at 5'(OH) a Branching Tangle of Alkly Chains Terminating in Aminated Chains Useful in the Detection of DNA Sequences by Non-Radioactive Methods The synthesis and use of mixed molecules composed of an oligodeoxyribonucleotide part and of a part possessing characteristic chemical properties allow easy and rapid detection of target deoxyribonucleic acids by non-radioactive methods. The oligodeoxyribonucleotide part of defined sequence homologous with a target DNA fragment provides the stabilization energy and ensures its hybridization with the DNA molecule that is to be detected. The part that provides the reactivity allowing direct or indirect detection of the hybrid can be introduced at the 5'(OH) and (or) 3'(OH) end of the nucleic acid sequence. In this specific example, the part responsible for the detection will essentially be introduced at the 5'(OH) position of the nucleic acid sequence.

The strategy employed means that the part responsible for detection can only be introduced at the 5'(OH) position. This will be done by preceding to a series of condensations of phosphoramidite 47 on the oligonucleotide chain still attaching to the solid support and protected on its bases and phosphates. After the series of condensations of 47, a final condensation of phosphoramidite 48 will enable n primary amine groups to be introduced by condensation of 48 at the n condensation sites (primary alcohol sites) created by the successive condensations of 47.

The condensations of 47 and 48 will be performed using the same reaction cycles in the automatic oligonucleotide synthesizer as those employed to synthesize the nucleic acid sequence. However, bearing in mind that the successive condensations of 47 have the effect of doubling the number of condensation sites with each cycle, the concentration of 47 used is 0.4 M and that of 48 is 0.8 M (conventional concentration 0.1 M). In respect of the two phosphoramidites 47 and 48 the splicing time is extended to 10 minutes instead of the 25 seconds used in the conventional cycle. After cleavage of the modified 5' oligonucleotide chain from its solid support and deprotection of the bases and phosphates, the part which provides the reactivity responsible for detection is introduced by means of a covalent chemical bond. Out of the various molecules possessing the requisite properties for detection, those preferably used are biotin, digoxigenin, fluorescein, peroxydase and alkaline phosphatase. These molecules, judiciously activated, attach to the oligonucleotide chain at the primary amines introduced for that purpose on account of their nucleophilic nature.

If

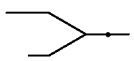

represents the group originating from condensation of a unit 47 where:

• represents a phosphate, and

represents the group resulting from condensation of a unit 48 where:

• represents a phosphate, the modified 5'(OH) oligomers which have been synthesized are as follows:

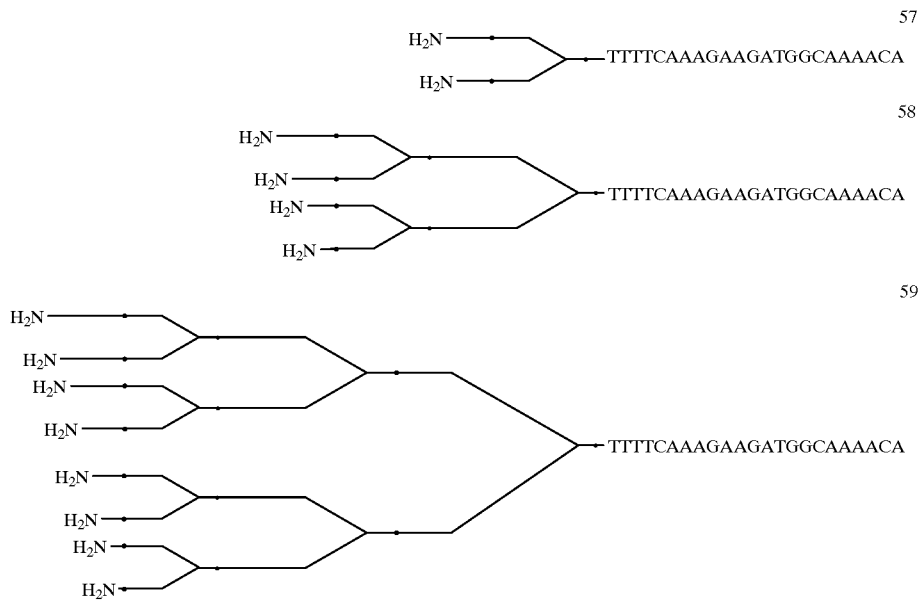

After cleavage of the accordingly modified oligonucleotide chain from its solid support and deprotection of the bases and phosphates, probes 57, 58 and 59 are biotinylated to result in the corresponding biotinylated probes 60, 61 and 62 (FIG. 8).

If the biotin unit originating from condensation of the biotin N hydroxysuccinimide on the primary amine groups is designated B, the following polybiotinylated probes are obtained at 5'(OH) position:

A DNA probe was synthesized with an oligodeoxynucleotide sequence complementary to a target sequence. In solid phase, in an automatic ABI 394 DNA synthesizer, three identical probes are simultaneously prepared (in three reactors) having the sequence:

5' TTTTCAAAGAAGATGGCAAAACA 3'.

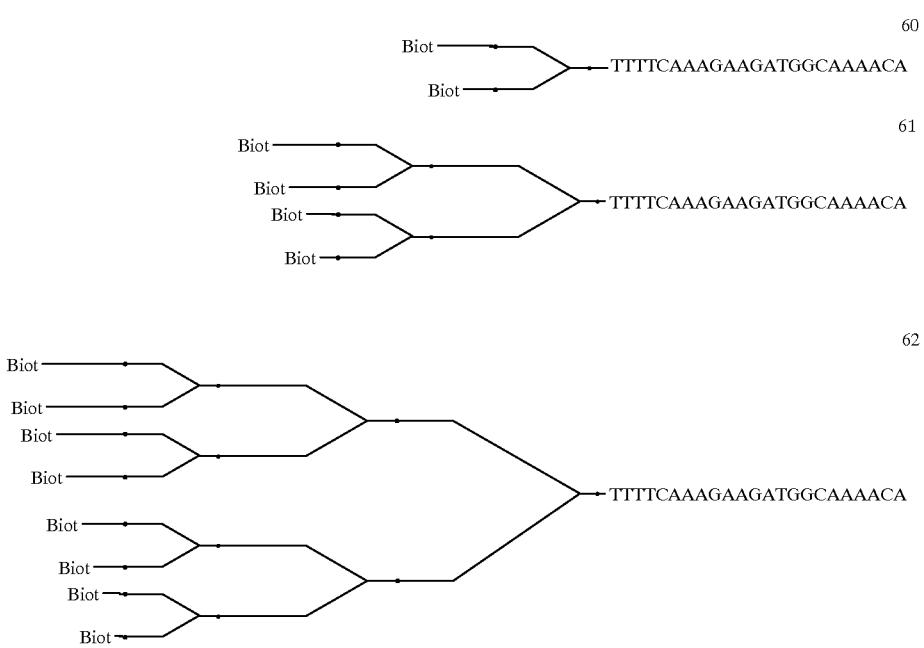

Method for Preparing Oligodeoxyribonucleotide Mixed Molecules Bearing at 5'(OH) a Branched Tangle of Alkyl Chains Terminating in Aminated Chains The synthesizer is programmed to continue attachment cycles at 5' of units 47 and then at the end of synthesis of a unit 48 in order to result respectively in probes 57, 58 and 59.

This involved the use of 6 mg of CPG support functionalized with dimethoxytrityl benzoyl adenosine at 34 μmoles/g, corresponding to 0.2 μmole. Derivatives 47 and 48 were solubilized in anhydrous acetonitrile at a concentration of 0.4 M for 47 and 0.8 M for 48. They are introduced into the synthesizer at the locations provided for non-conventional phosphorarnidites. Following automatic synthesis of biopolymers 57, 58 and 59, the oligonucleotide chains accordingly modified are cleaved from the CPG supports by four successive 15-minute treatments with 500 μl of 32% $NH_4OH$. The ammonia solutions obtained are maintained at 55° C. for 5 hours. The object of this second treatment is to deprotect the bases and phosphates of the oligonucleotide chains. The ammonia solutions are lyophilized, the four residues are subjected to molecular filtration chromatography (G50 Sephadex gel), and then to electrophoresis on 20% polyacrylamide gel.

Method for Biotinylation of Oligodeoxyribonucleotide Mixed Molecules Bearing at 5'(OH) a Branching Tangle of Alkyl Chains Terminating in Aminated Chains 20 DO of aminated probe 57, 58 or 59 is dissolved in an Eppendorf tube in 120 μl of phosphate buffer, 0.01 M, pH 7.5. A solution of 20 mg of sulfosuccinimidyl 6-biotinamidocaproate in 240 μl of dimethylformamide is added. This is incubated for 16 hrs at room temperature. Each solution is subjected to molecular filtration chromatography (G50 Sephadex gel), and then to electrophoresis on 20% polyacrylamide gel.

Probes 57, 58, 59, 60, 61 and 62 were analyzed by capillary electrphoresis on an ABI 270A, Micro-Gel$_{100}$ column, internal diameter 50 μm, length 50 cm, voltage 15 kV, buffer 75 mM Tris-phosphate—10% methanol pH 7.6.

EXAMPLE XIII

Use of the Biotinylated Probes Described in Example XII in Hybridization on a Solid Support—Limits of Detection In order to reveal the advantages of the present invention, the probes polybiotinylated at 5'(OH) 60, 61, and 62 were tested in hybridization in order to investigate their potential for diagnostic use.

Generally speaking, hybridization takes place between an oligonucleotide (30 mer) attaching to a plastics solid support by its 5'(OH) extremity and complementary to the probes to be tested (23 mer) by its 3'(OH) extremity. Each solid support (tube) is coated with of the order of 10 ng of oligonucleotide (30 mer) complementary to the probes to be tested, representing approximately $10^{12}$ copies.

Each biotinylated oligonucleotide mentioned above is subjected to 8 different hybridizations, starting off with 1 pg labelled oligonucleotide (~$10^8$ copies) and going as far as 300 atg ($3 \times 10^4$ copies) in 1/3 dilutions, from one bowl to the next. After hybridization, chemiluminescence (CSPD—Tropix) is used for disclosure; the reading is taken on a luminometer.

Scheme IX summarizes the results of the hybridization of probes 60, 61, and 62.

| | | Scheme IX | | |
|---|---|---|---|---|
| | | | Limit of detection | |
| OLIGO | Number of biotins | | fg | no. of copies |
| 60 | 2 | 5'(OH) | 10 | $10^6$ |
| 61 | 4 | 5'(OH) | 10 | $10^6$ |
| 62 | 8 | 5'(OH) | 3 | $3 \times 10^5$ |

Method for Hybridization of a Monobiotinylated or Polybiotinylated Probe (23 mer) with a Complementary Oligomer (30 mer) Attaching to a Plastics Tube The tubes, covered with complementary oligonucleotide (30 mer) are first saturated for one hour at 37° C. with 200 μl of a 5% solution of skimmed milk lyophilized in TBS 1× containing a trace of azide. The tubes are then prehybridized for 2 hours at 50° C. with the hybridization buffer (100 μl): 5× Denhardt's, 6×SSC, 0.1% SDS, 100 μg/ml of salmon sperm DNA.

For each oligonucleotide to be tested, 8 trials are undertaken with the following quantities (in 100 μl of hybridization buffer): 1 pg ($10^8$ copies), 300 fg, 100 fg ($10^7$ copies), 30 fg, 10 fg, ($10^6$ copies), 3 fg, 1 fg ($10^5$ copies), 0.3 fg. A series of eight tubes is also produced with an unbiotinylated, non-complementary oligomer, and eight tubes without oligonucleotide. All the tubes are hybridized for 2 hrs at 50° C., then each tube is washed three times for ten minutes at 50° C. with an SSC 6× solution. They are then washed once for five minutes with buffer I.

Buffer I: 0.1 M Tris, 2 mM $MgCl_2$, 0.05% triton, 1 M NaCl.

A solution of alkaline streptavidin-phosphatase is now prepared (supplied with the Tropix kit): 1 μl of the solution from the kit in 5,500 μl of buffer I. 100 μl of this solution are put into each tube, left to incubate for thirty minutes at room temperature, and then each tube is washed six times with buffer I. The solution of chemiluminescent agent CSPD is prepared: (3-(4-methoxyspiro[1,2-dioxetane-3,2'-tricyclo [3.3.1.1.]chlorodecane]-4-yl) phenyl phosphate. The solution is prepared as follows: 80 μl of CSPD (Tropix), 500 μl of "emerald" (Tropix) and 4,420 μl of disclosing buffer.

Disclosing buffer: 0.1 M diethanolamine, 1 mM $MgCl_2$, 0.02% sodium azide. 100 μl of this solution is placed in each tube, left to incubate for 45 min and then read on the luminometer.

We claim:

1. A nucleic acid probe represented by formula (Ia)

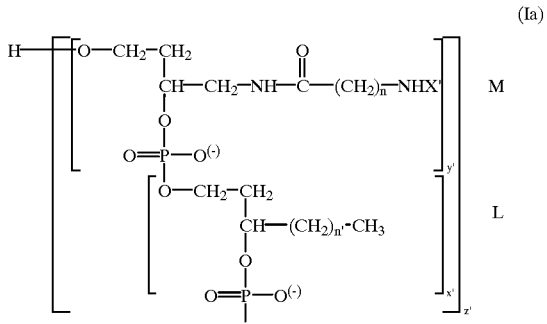

(Ia)

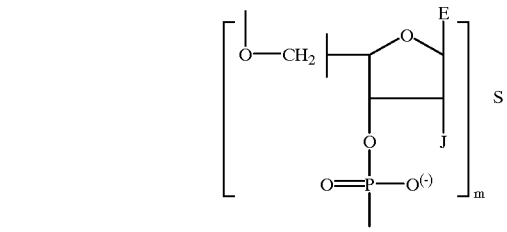

-continued

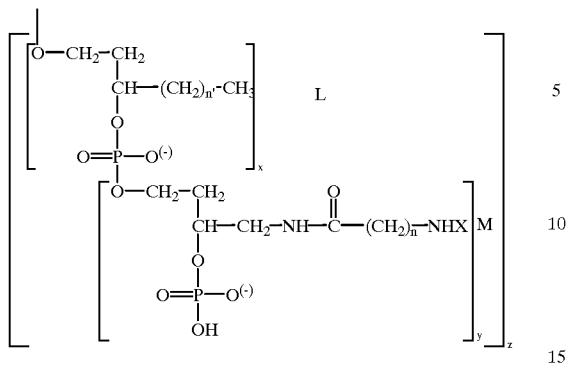

wherein,

M is an alkyl group substituted with a primary amine group which allows an attachment of a marker X, which is detectable in a non-isotopic manner by production of color or light, L is an alkyl group, S is an oligonucleotide, J is H or OH;

B is a purine or pyriraidine, and m is an integer of from 1 to 1000;

x and x' are each 0 or an integer of from 1 to 100, and n' is 0 or an integer of from 1 to 20;

y and y' are each an integer of from 1 to 100, and n is an integer of from 2 to 20;

wherein said X is selected from the group consisting of fluorescein, any enzyme capable of producing a color or a light in the presence of a substrate, a hapten, and a protecting group of the primary amine group and said LM is introduced at the 5'(OH) where z'≠0 and z=0, at the 3'(OH) where z'=0 and z≠0, simultaneously at the 5'(OH) and at the 3'(OH) where z'≠0 and z≠0, z and z' are individually each 0 or an integer of from 1 to 100, with the proviso that z and z' are not simultaneously 0.

2. The nucleic acid probe according to claim 1, wherein said enzyme is alkaline phosphatase, or peroxidase, and said hapten is selected from the group consisting of biotin and digoxigenin.

3. A nucleic acid probe represented by formula (XX):

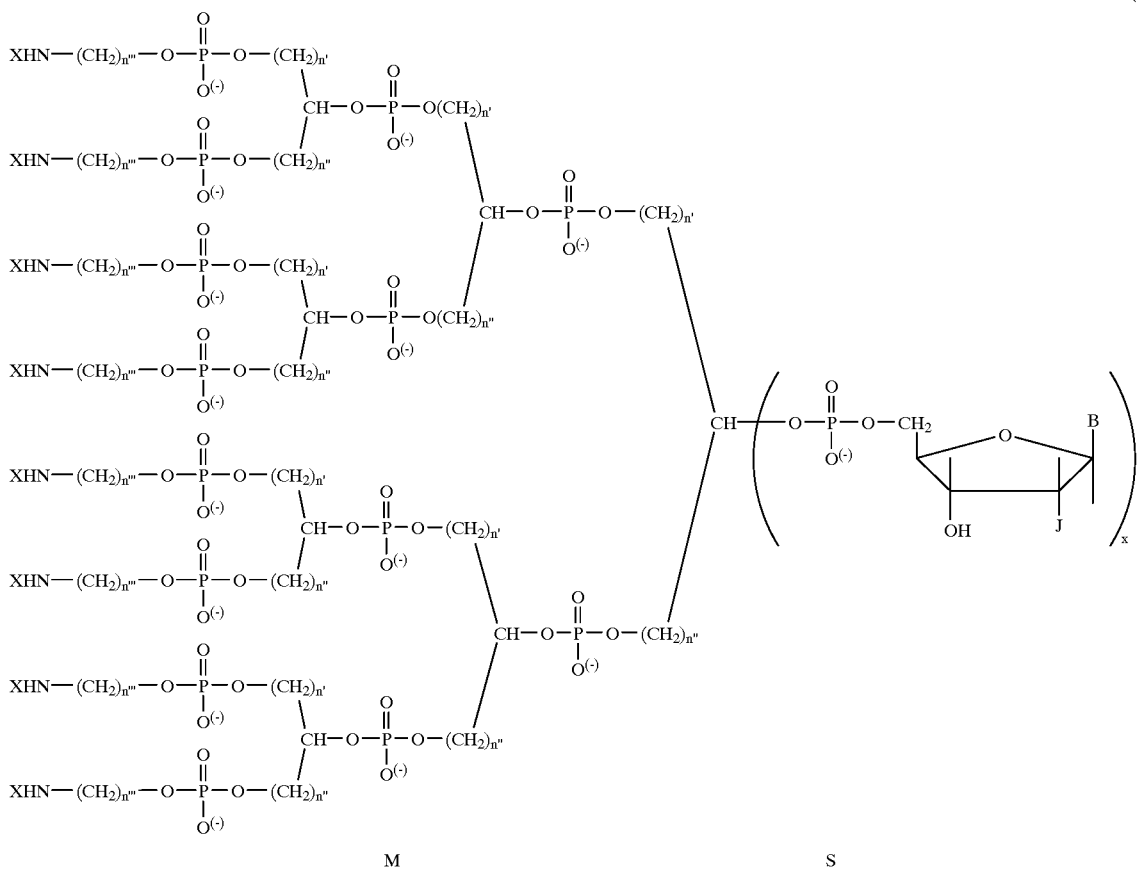

wherein,

J is H or OH,

B is a purine or pyrimidine, x is an integer of from 1 to 1000, and n, n', n" and n'" are an integer of from 1 to 20;

S is an oligonucleotide, wherein the branching arrangement, M, may terminate in 2 to 128 aminated arms.

4. The nucleic acid probe according to claim 1, wherein said M is prepared from an intermediate compound represented by formula (III):

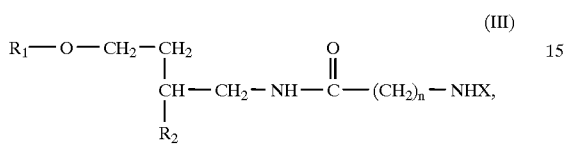

(III)

wherein n is an integer of from 1 to 20;

$R_1$ is a protecting group; and $R_2$ represents a phosphorylated group, protected if necessary, capable of receiving compound (III) at the end of a oligonucleotide or a preexisting nucleic acid probe represented by formula (I) on a solid support.

5. The nucleic acid probe according to claim 4, wherein $R_1$ is a 4,4'-dimethoxytrityl group, and $R_2$ is a cyanoethoxydiisopropylaminophosphoramidite group.

6. The nucleic acid probe according to claim 4, wherein X is a trifluoroacetyl group or a benzoyl group.

* * * * *

UNITED STATES PATENT AND TRADEMARK OFFICE
CERTIFICATE OF CORRECTION

PATENT NO.   : 5,969,128
DATED        : October 19, 1999
INVENTOR(S)  : De Vos, Marie-Joelle, Bollen, Alex It is certified that error appears in the above-identified patent and that said Letters Patent is hereby corrected as shown below:

Title page,
OTHER PUBLICATIONS, delete "olgionucleotide systhesis" and insert
-- oligonucleotide synthesis --.

ABSTRACT,
Line 5, delete "atttachment" and insert -- attachment --.

Drawings,
Insert Figs. 2I-8F (17 sheets).
Columns 3-4, delete

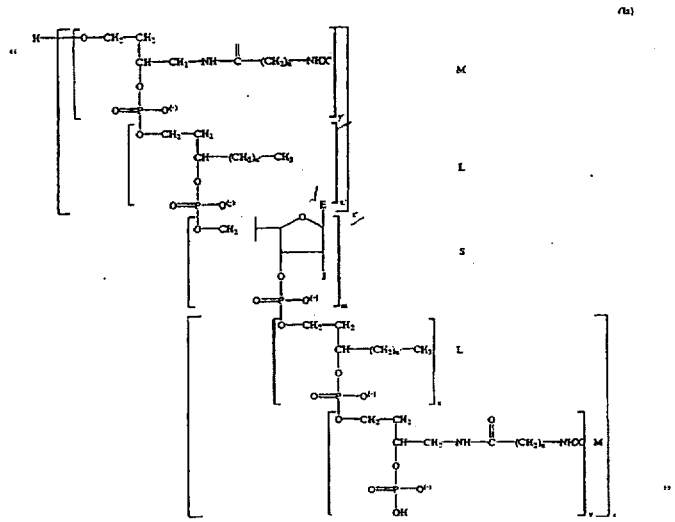

Signed and Sealed this

Fifth Day of February, 2002

Attest:

JAMES E. ROGAN
*Attesting Officer*          *Director of the United States Patent and Trademark Office*

UNITED STATES PATENT AND TRADEMARK OFFICE
CERTIFICATE OF CORRECTION

PATENT NO. : 5,969,128
DATED : October 19, 1999
INVENTOR(S) : De Vos, Marie-Joelle, Bollen, Alex Page 2 of 24

It is certified that error appears in the above-identified patent and that said Letters Patent is hereby corrected as shown below:

and insert

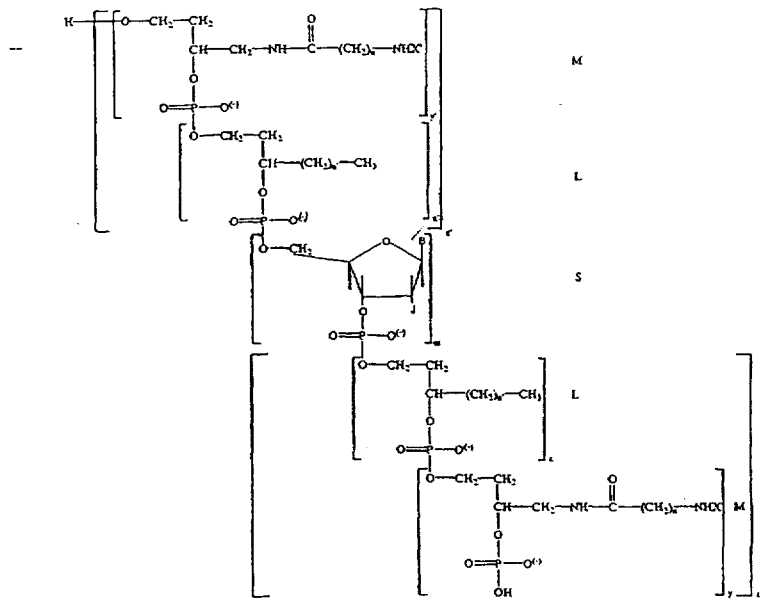

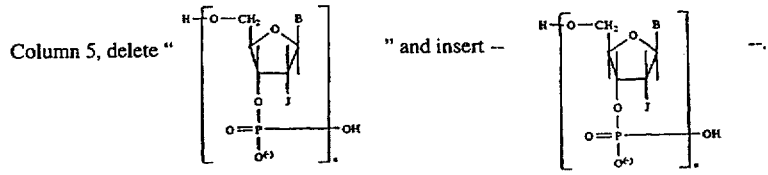

Column 11,
Line 33, delete "M" and insert -- X1 --.

Column 13,
Line 56, insert -- five -- before carbon.

Column 18,
Line 12, delete "pylarinocyanoethoxychlorophosphine" and insert
-- pylaminocyanoethoxychlorophosphine --.

UNITED STATES PATENT AND TRADEMARK OFFICE
CERTIFICATE OF CORRECTION

PATENT NO. : 5,969,128
DATED : October 19, 1999
INVENTOR(S) : De Vos, Marie-Joelle, Bollen, Alex It is certified that error appears in the above-identified patent and that said Letters Patent is hereby corrected as shown below:

Column 20,
Line 2, delete "tetrahydroftirane" and insert -- tetrahydrofurane -- and
Line 42, delete "2-cyanothoxydiisopropylmino" and insert -- 2-cyanoethoxydiisopropylamino --

Column 23,
Line 40, delete "4,4'-dimethoxytnityl" and insert -- 4,4'dimethoxytrityl --; and
Line 50, delete "NaHCO3" and insert -- $NaHCO_3$ --.

Column 24,
Line 64, delete "ammona" and insert -- ammonia --.

Column 25,
Line 7, delete "6-4trifluoroacetymidocaproic" and insert -- 6-trifluoroacetamidocaproic --;
Line 9, delete "dimethylformarnde" and insert -- dimethylformamide --; and
Line 44, delete "4,4'-dimethoxotrityl" and insert -- 4,4'-dimethoxytrityl --.

Columns 29-30,
For the figure delete "Scheme 3" and insert -- Scheme III --.

Column 30,
Line 32, delete "temprature" and insert -- temperature --.

Column 31,
Line 16, delete "sulfonic" and after "toluene" insert -- sulfonic --.

Column 33,
Line 44, delete "amnines" and insert -- amines --.

Column 35,
Line 15, delete "digongenin," and "fluoroescein" and insert -- digoxigenin -- and -- fluorescein --.

UNITED STATES PATENT AND TRADEMARK OFFICE
CERTIFICATE OF CORRECTION

PATENT NO.   : 5,969,128
DATED        : October 19, 1999
INVENTOR(S)  : De Vos, Marie-Joelle, Bollen, Alex It is certified that error appears in the above-identified patent and that said Letters Patent is hereby corrected as shown below:

Column 41,
Lines 40-57, delete

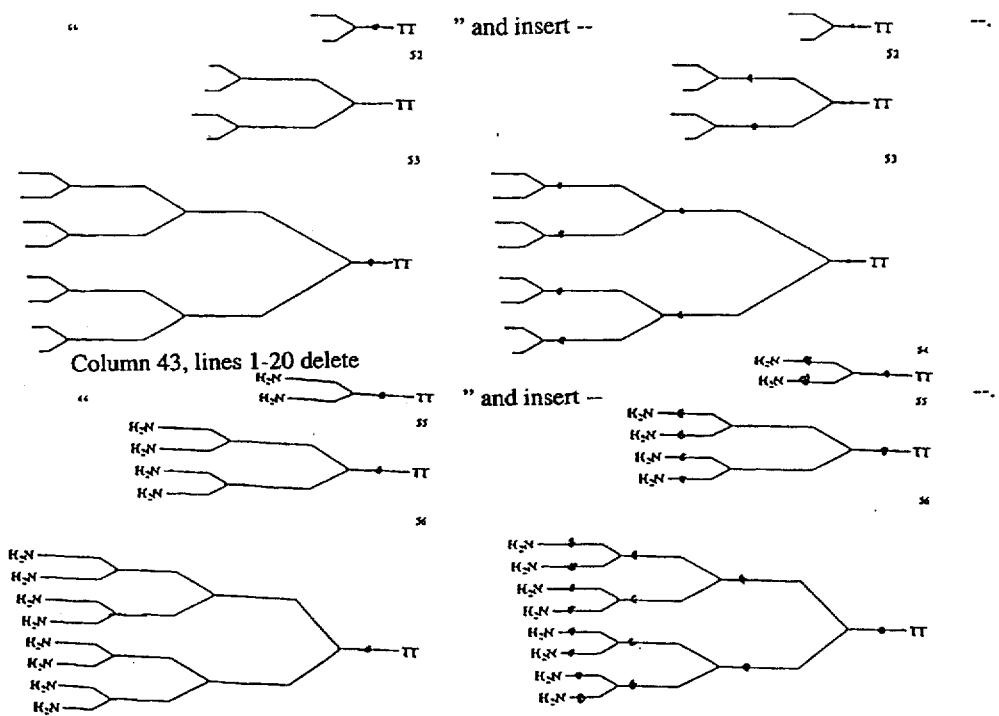

Column 43,
Line 60, delete "alkly" and insert -- alkyl --.

Column 44,
Lines 50 and 58, delete

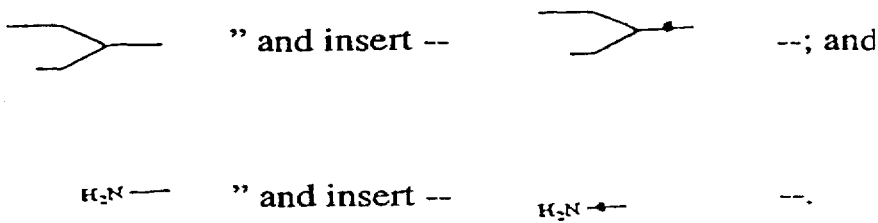

UNITED STATES PATENT AND TRADEMARK OFFICE
CERTIFICATE OF CORRECTION

PATENT NO. : 5,969,128
DATED : October 19, 1999
INVENTOR(S) : De Vos, Marie-Joelle, Bollen, Alex It is certified that error appears in the above-identified patent and that said Letters Patent is hereby corrected as shown below:

Column 47,
Line 38, delete "plastics" and insert -- plastic --.

Claim 1, line 2, delete " 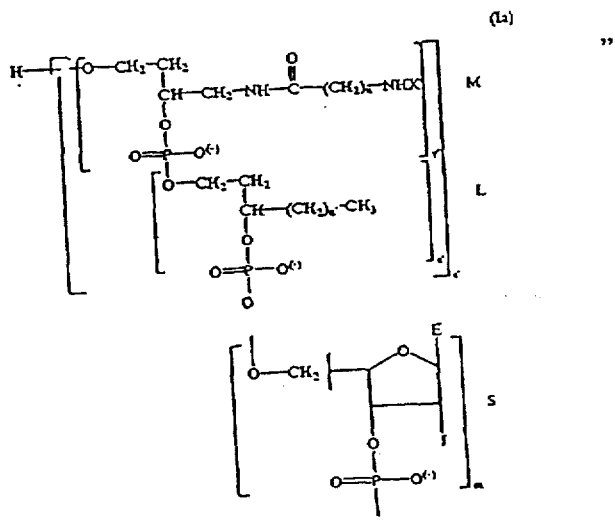 "

and insert -- 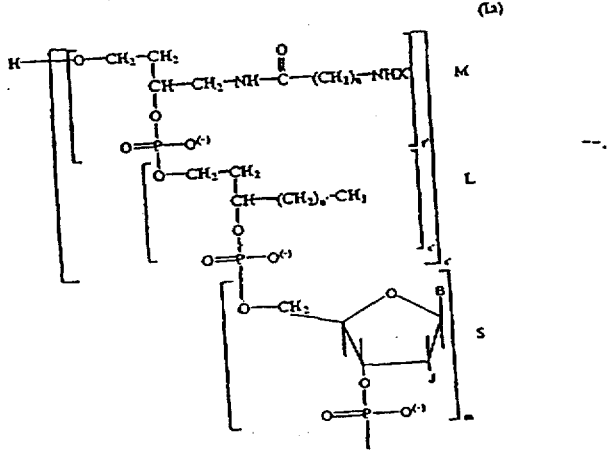 --.

Column 49, claim 1,
Line 23, delete ""ofigonucleotide" and insert -- oligonucleotide --.

UNITED STATES PATENT AND TRADEMARK OFFICE
CERTIFICATE OF CORRECTION

PATENT NO. : 5,969,128
DATED : October 19, 1999
INVENTOR(S) : De Vos, Marie-Joelle, Bollen, Alex It is certified that error appears in the above-identified patent and that said Letters Patent is hereby corrected as shown below:

Column 50, claim 1,
Line 1, delete "pyriraidine" and insert - pyrimidine -.

Columns 49 and 50, claim 3,
Line 2, delete
"

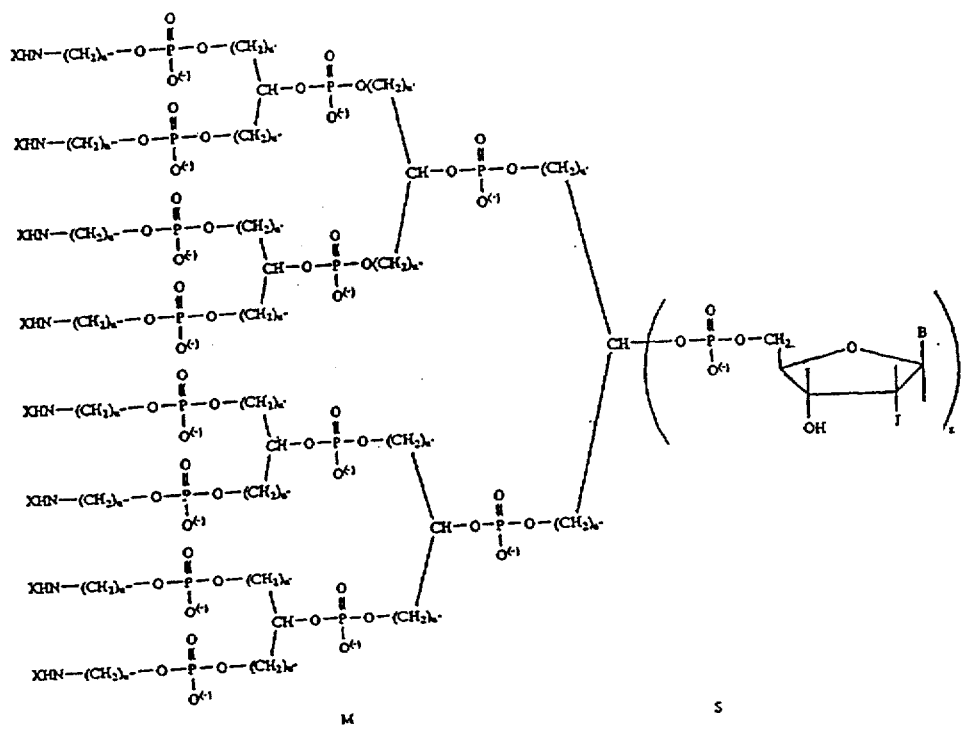

"

UNITED STATES PATENT AND TRADEMARK OFFICE
CERTIFICATE OF CORRECTION

PATENT NO. : 5,969,128
DATED : October 19, 1999
INVENTOR(S) : De Vos, Marie-Joelle, Bollen, Alex It is certified that error appears in the above-identified patent and that said Letters Patent is hereby corrected as shown below:

and insert --

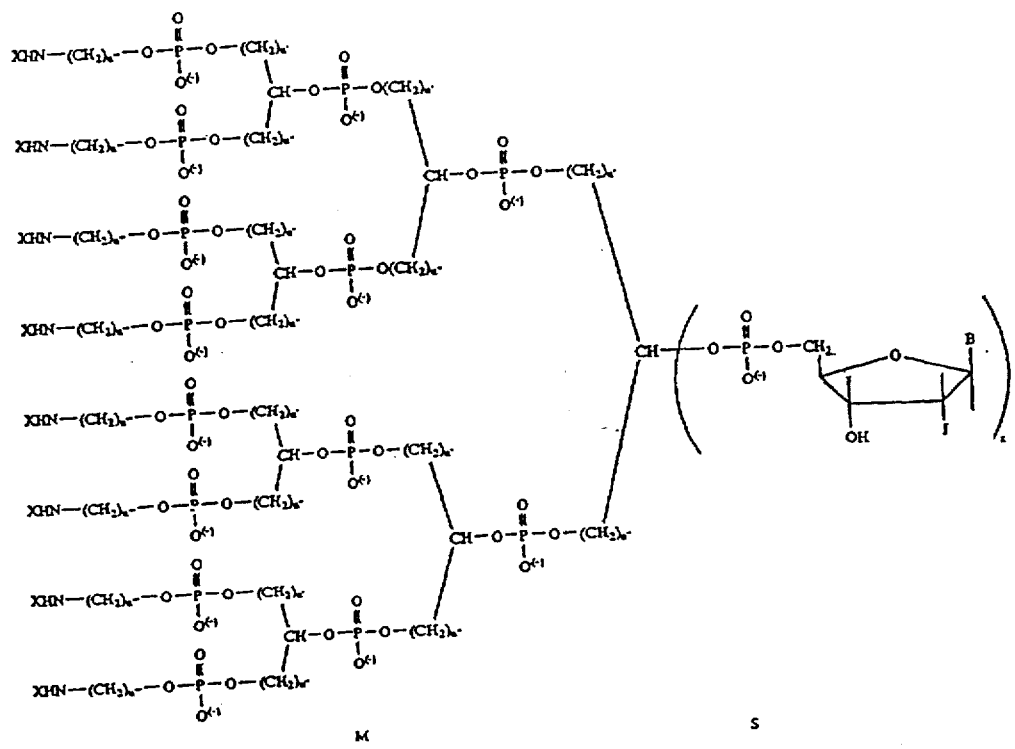

--

TT-S-S
10.41 min.

S-S-TT
10.23 min.

Figure 5A:
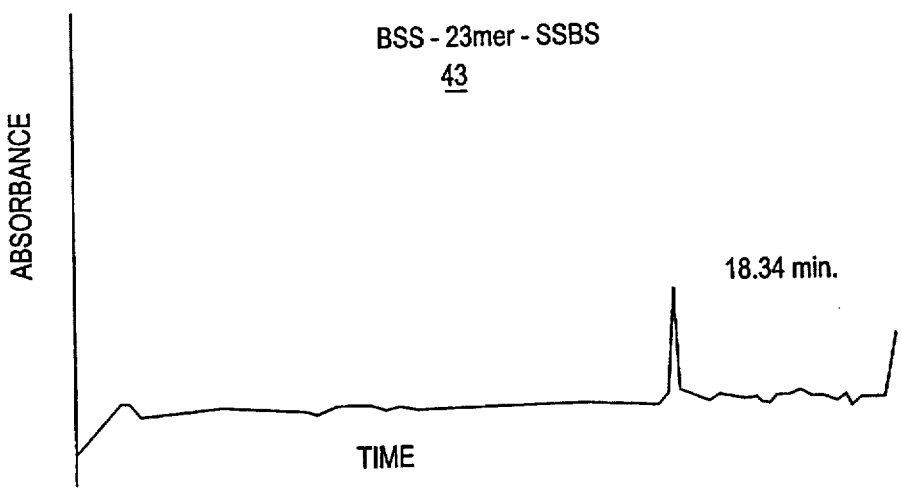
Figure 5B:
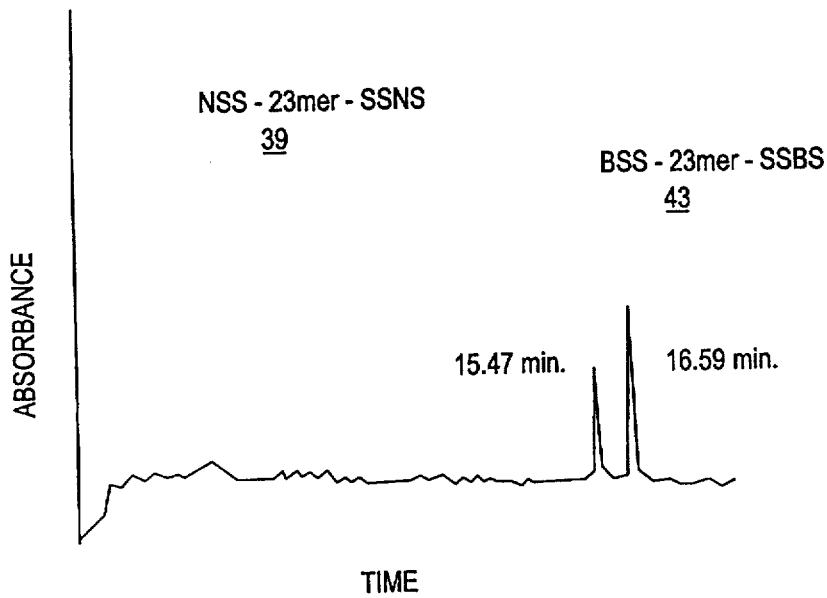
Figure 5C:
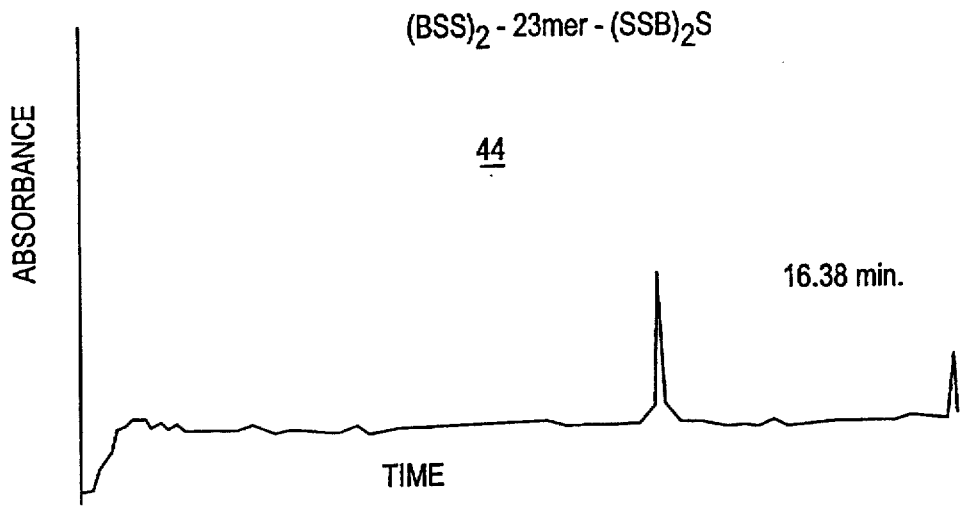
Figure 5D:
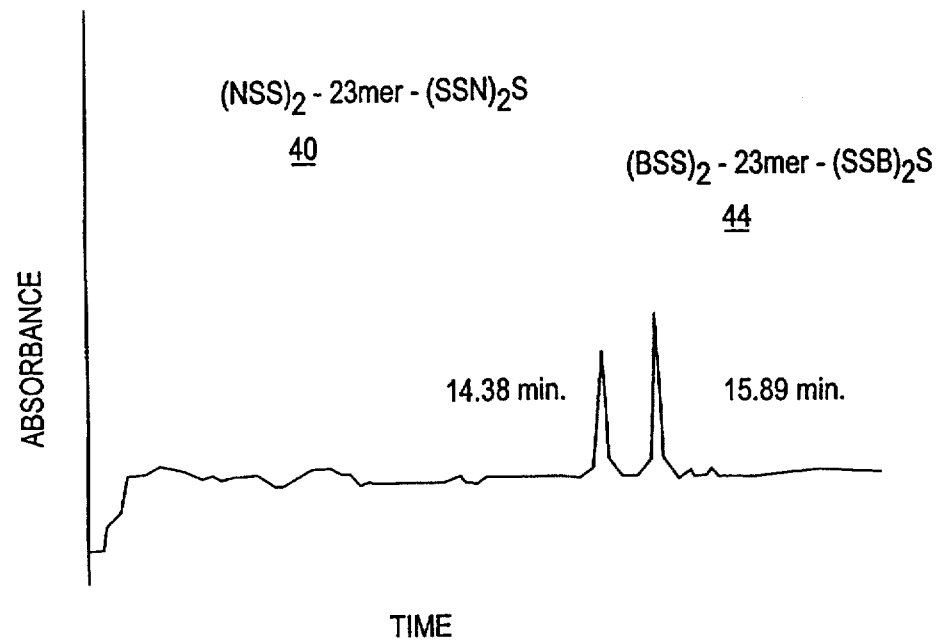
Figure 5G:
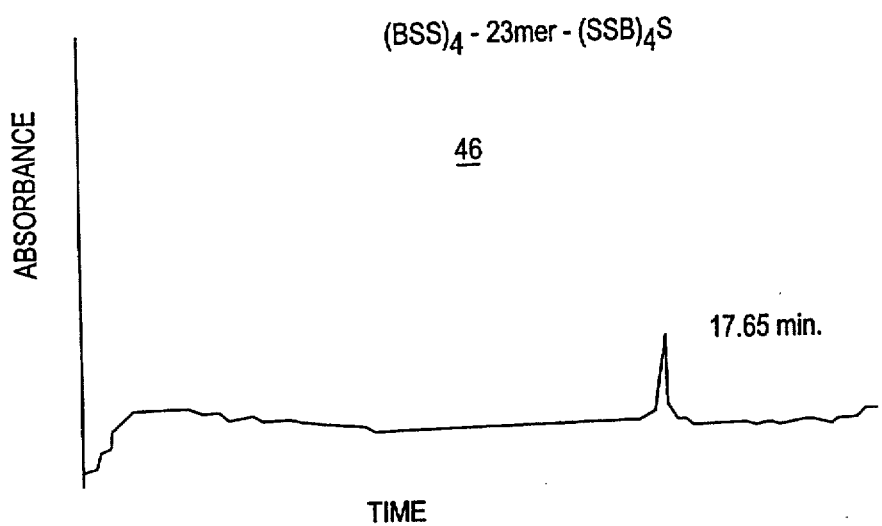
Figure 5H:
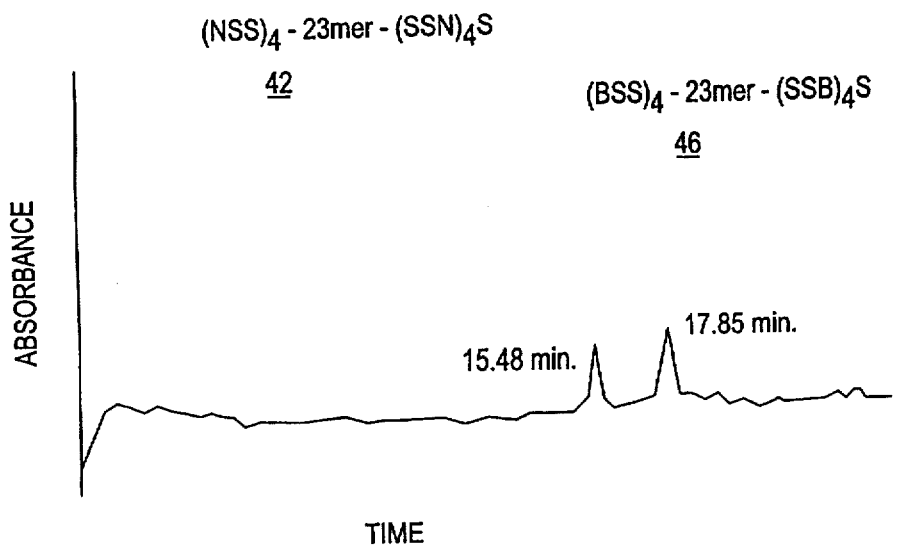

FIG. 5E (BSS)$_3$ - 23mer - (SSB)$_3$S

45

ABSORBANCE 16.93 min.

TIME

FIG. 5F (NSS)$_3$ - 23mer - (SSN)$_3$S

41

(BSS)$_3$ - 23mer - (SSB)$_3$S

45

ABSORBANCE 13.92 min.

15.78 min.

TIME 17.54 min.

51.

TIME 13.99 min.

15.13 min.

52.

TIME

UNITED STATES PATENT AND TRADEMARK OFFICE
CERTIFICATE OF CORRECTION

PATENT NO.  : 5,969,128  
DATED       : October 19, 1999  
INVENTOR(S) : Marie-Joëlle De Vos and Alex Bollen Page 1 of 1

It is certified that error appears in the above-identified patent and that said Letters Patent is hereby corrected as shown below:

<u>Title page,</u>
Item [73], Assignee, delete "Wallone" and insert -- Wallonne --.

Signed and Sealed this

Twenty-third Day of April, 2002

Attest:

JAMES E. ROGAN  
*Director of the United States Patent and Trademark Office*

*Attesting Officer*